United States Patent
Hagiwara

[11] Patent Number: 5,838,433
[45] Date of Patent: Nov. 17, 1998

[54] APPARATUS FOR DETECTING DEFECTS ON A MASK

[75] Inventor: Tsuneyuki Hagiwara, Tokyo, Japan

[73] Assignee: Nikon Corporation, Tokyo, Japan

[21] Appl. No.: 636,511

[22] Filed: Apr. 19, 1996

[30] Foreign Application Priority Data

Apr. 19, 1995 [JP] Japan .................................. 7-094031
Sep. 19, 1995 [JP] Japan .................................. 7-240156

[51] Int. Cl.$^6$ .................................................. G01N 21/00
[52] U.S. Cl. ...................... 356/237; 356/339; 356/364; 356/367
[58] Field of Search .................................. 356/237, 339, 356/364, 367

[56] References Cited

U.S. PATENT DOCUMENTS

| | | | |
|---|---|---|---|
| 3,790,287 | 2/1974 | Cuthbert et al. | 352/237 |
| 4,468,120 | 8/1984 | Tanimoto et al. | 356/237 |
| 4,610,541 | 9/1986 | Tanimoto et al. | 356/237 |
| 4,681,442 | 7/1987 | Wagner | 356/237 |

FOREIGN PATENT DOCUMENTS

| | | |
|---|---|---|
| 2-56626 | 11/1990 | Japan . |
| 4-122042 | 4/1992 | Japan . |
| 5-165196 | 6/1993 | Japan . |
| 6-43111 | 2/1994 | Japan . |
| 6-94633 | 4/1994 | Japan . |
| 7-117496 | 12/1995 | Japan . |

*Primary Examiner*—David C. Nelms
*Assistant Examiner*—Reginald A. Ratiff
*Attorney, Agent, or Firm*—Foley & Lardner

[57] ABSTRACT

The present invention discloses a mask defect inspection apparatus for optically detecting a defect on a mask having a circuit pattern, which comprises an illumination system for illuminating the mask with inspection light; a first light receiving optical system for receiving the inspection light reflected by the mask; a second light receiving optical system for receiving the inspection light transmitted by the mask; a first spatial filter for shielding the inspection light passing through a central region including the optical axis of the first light receiving optical system in an optical Fourier transform plane for the circuit pattern in the first light receiving optical system; a second spatial filter for shielding the inspection light passing through a central region including the optical axis of the second light receiving optical system in an optical Fourier transform plane for the circuit pattern in the second light receiving optical system; a first detector for photoelectrically converting the inspection light having passed through the first spatial filter; a second detector for photoelectrically converting the inspection light having passed through the second spatial filter; and a gain adjusting circuit for adjusting a gain of a first output signal from the first detector to output a third output signal and adjusting a gain of a second output signal from the second detector to output a fourth output signal, wherein the defect is detected based on either a relative intensity difference or intensity ratio between the third output signal and the fourth output signal gain-adjusted by the gain adjusting circuit.

34 Claims, 39 Drawing Sheets

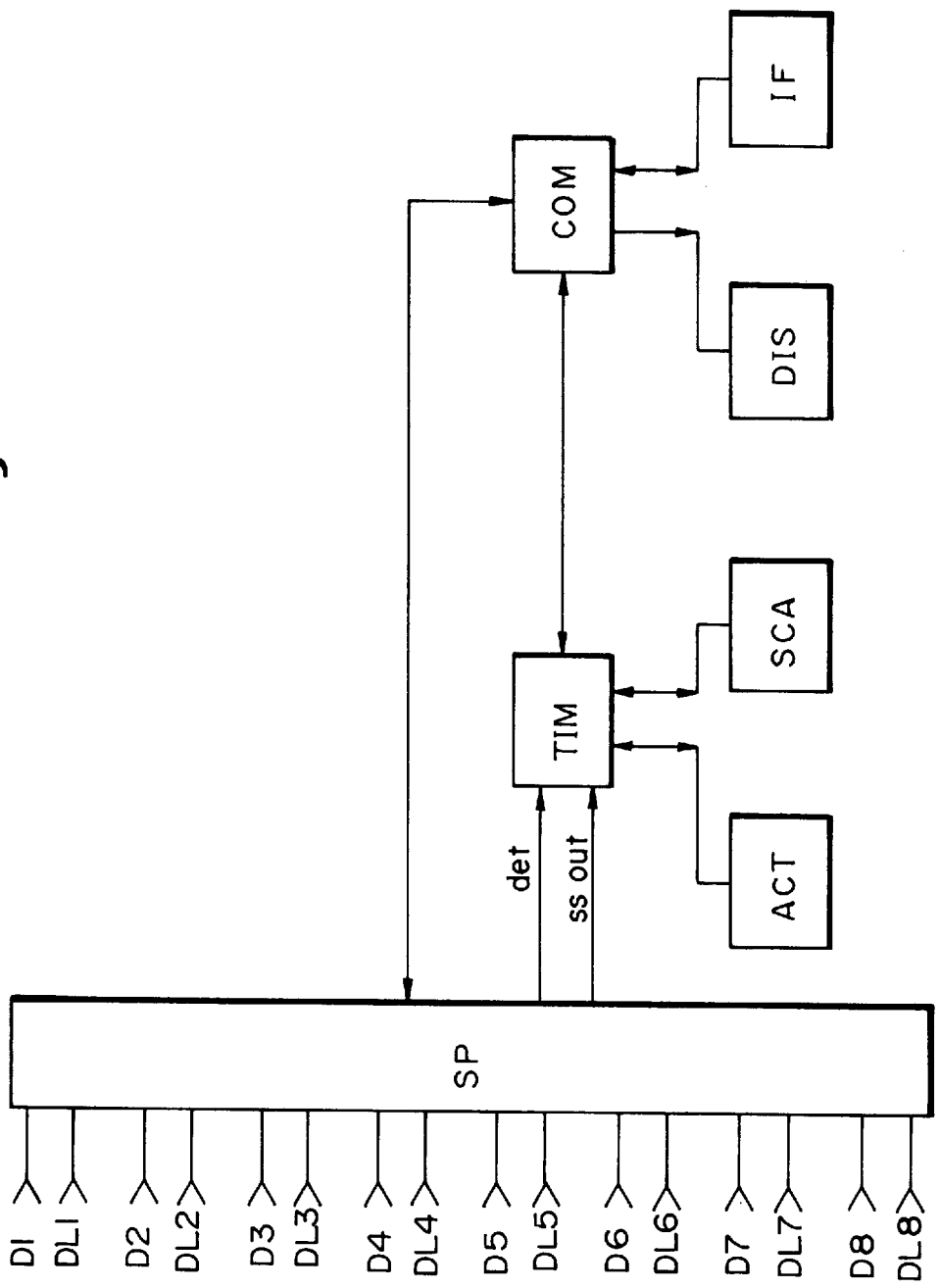

APPARATUS FOR DETECTING DEFECTS ON A MASK

BACKGROUND OF THE INVENTION

1. Field of the Invention

The present invention relates to a mask defect inspection apparatus, and more particularly, to an apparatus for optically detecting defects (including defects such as foreign matter attached to a mask) of a mask on which circuits such as IC are patterned.

2. Related Background Art

Examples of the mask defect inspection apparatus or foreign matter inspection apparatus conventionally known include those described in U.S. Pat. Nos. 4,610,541, 4,468,120, and 4,681,422.

With these apparatus there were, however, some cases that such apparatus failed to adequately detect a microscopic mask defect, foreign matter, or the like.

SUMMARY OF THE INVENTION

The present invention has been accomplished taking the above conventional problem into consideration. An object of the present invention is to provide a mask defect inspection apparatus that can detect a microscopic mask defect (for example, a flat mask defect etc.) or a semitransparent mask defect existing on the mask.

A further object of the present invention is to provide a mask defect inspection apparatus for optically detecting a defect on a mask having a circuit pattern, comprising:

- an illumination system for illuminating the mask with inspection light;
- a first light receiving optical system for receiving the inspection light reflected by the mask;
- a second light receiving optical system for receiving the inspection light transmitted by the mask;
- a first spatial filter for shielding the inspection light in a central area including an optical axis of the first light receiving optical system in an optical Fourier transform plane for the circuit pattern in the first light receiving optical system;
- a second spatial filter for shielding the inspection light in a central area including an optical axis of the second light receiving optical system in an optical Fourier transform plane for the circuit pattern in the second light receiving optical system;
- a first detector for photoelectrically converting the inspection light having passed through the first spatial filter;
- a second detector for photoelectrically converting the inspection light having passed through the second spatial filter; and
- a gain adjusting circuit for adjusting a gain of a first output signal from the first detector to output a third output signal and adjusting a gain of a second output signal from the second detector to output a fourth output signal,
- wherein the defect is detected based on either a relative intensity difference or intensity ratio between the third output signal and the fourth output signal gain-adjusted by the gain adjusting circuit.

A still further object of the present invention is to provide a mask inspection apparatus for inspecting a defect of a mask having a circuit pattern on a first surface of an optically transparent substrate of a flat plate shape, but having no circuit pattern on a second surface opposite to the first surface, comprising:

- illuminating means for illuminating an inside area of an inspection region being a region inside the first surface as an inspection object of the mask;
- two light receiving means disposed separately from each other in two spaces obtained when a space including the mask is divided into two by a plane including the first surface, said two light receiving means being second light receiving means located in a second space including the second surface and first light receiving means located in a first space not including the second surface;
- first photoelectric conversion means for photoelectrically converting rays occurring from the inside area of the inspection region of the mask and entering the first light receiving means;
- second photoelectric conversion means for photoelectrically converting rays occurring from the inside area of the inspection region of the mask and entering the second light receiving means; and
- a gain adjusting circuit for adjusting a gain of a first output signal output from the first photoelectric conversion means to output a third output signal and adjusting a gain of a second output signal output from the second photoelectric conversion means to output a fourth output signal,
- wherein the defect is detected based on either a relative intensity difference or intensity ratio between the third output signal and the fourth output signal gain-adjusted by the gain adjusting circuit.

A still further object of the present invention is to provide a mask defect inspection apparatus for inspecting a defect of a mask, comprising:

- first illuminating means for vertically illuminating an inside area of a first region of an inspected surface of the mask;
- second illuminating means for transmission-illuminating the inside area of the first region of the inspected surface from a surface of the mask different from the inspected surface;
- ray selecting means for condensing only scattered light occurring from inside a second region at a first position in the first region into a first ray;
- ray splitting means for splitting the first ray into a second ray and a third ray;
- first photoelectric conversion means for photoelectrically converting the second ray;
- second photoelectric conversion means for photoelectrically converting the third ray; and
- a gain adjusting circuit for adjusting a gain of a first output signal output from the first photoelectric conversion means to output a third output signal and adjusting a gain of a second output signal output from the second photoelectric conversion means to output a fourth output signal,
- wherein the defect is detected based on either a relative intensity difference or intensity ratio between the third output signal and the fourth output signal gain-adjusted by the gain adjusting circuit.

A still further object of the present invention is to provide a mask defect inspection apparatus for inspecting a defect of an optically transparent substrate of a plate shape having a first surface and a second surface opposed to each other, in which a pattern is scribed on the first surface but no pattern is scribed on the second surface, comprising:

- a laser light source for emitting a laser beam;

light scanning means for condensing the laser beam in a first region of the first surface of the substrate and irradiating the first region with the laser beam, said light scanning means continuously moving the first region in a one-dimensional direction in the pattern-scribed surface of the substrate;

first light receiving means having a photoelectric conversion element and disposed in a first space region not including the second surface, said first space region being one of two space regions divided by a first plane including the first surface of the substrate;

second light receiving means having a photoelectric conversion element and disposed in a second space region including the second surface, said second space region being one of the two space regions divided by the first plane including the first surface of the substrate; and a gain adjusting circuit for adjusting a gain of a first output signal from the first light receiving means to output a third output signal and adjusting a gain of a second output signal from the second light receiving means to output a fourth output signal, wherein the defect is detected based on either a relative intensity difference or intensity ratio between the third output signal and the fourth output signal gain-adjusted by the gain adjusting circuit.

BRIEF DESCRIPTION OF THE DRAWINGS

FIG. 32 is a drawing to show the signal processing system in the apparatus of FIG. 31A;

DESCRIPTION OF THE PREFERRED EMBODIMENTS

Figure 1:
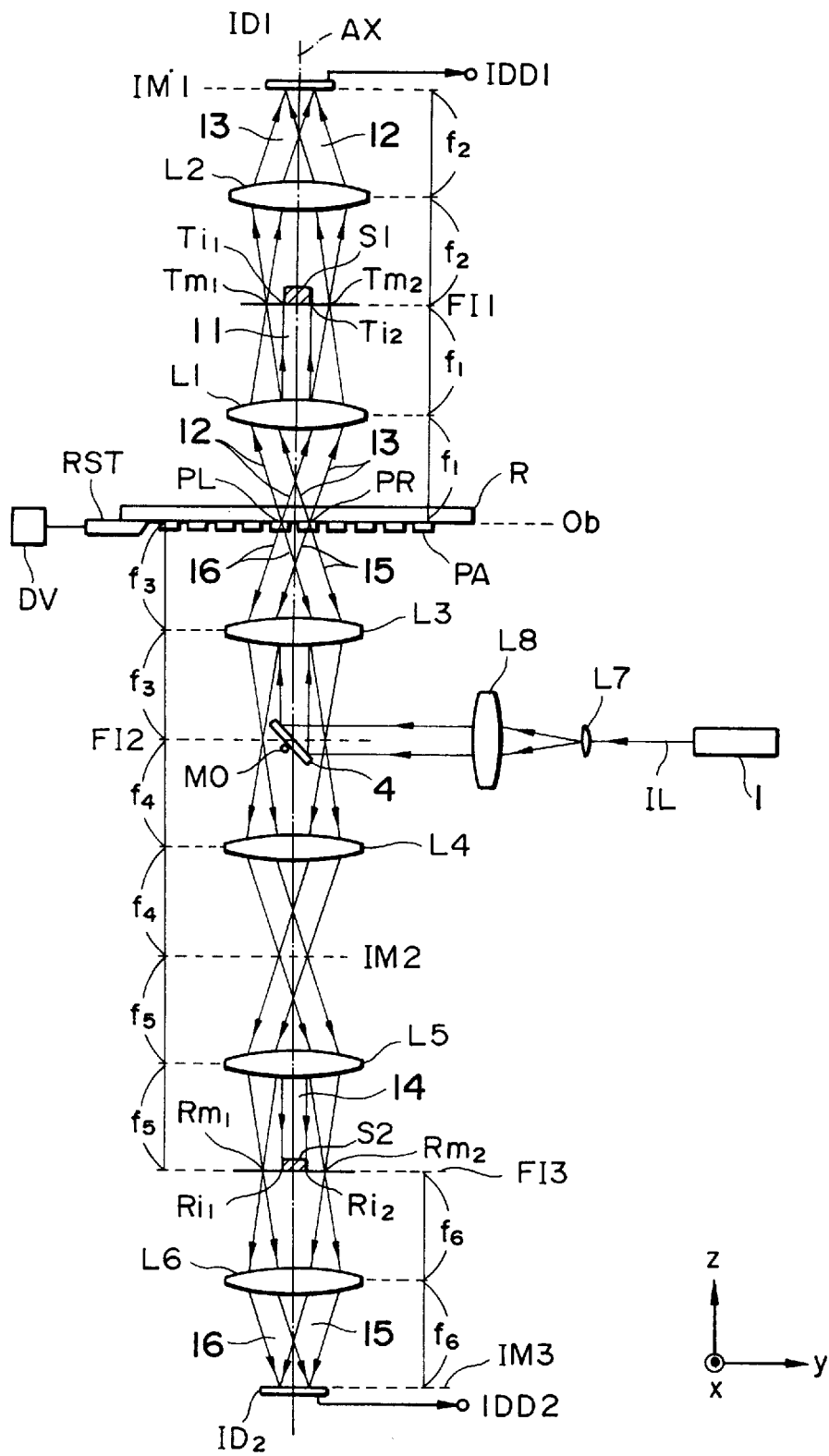
FIG. 1 is a drawing to show the schematic structure of a mask defect inspection apparatus suitable for the first embodiment of the present invention.

The first embodiment of the present invention will be explained with reference to the drawings. FIG. 1 is a drawing to show the schematic structure of the mask defect inspection apparatus of the present embodiment. This apparatus is an apparatus having both a reflection detection system and a transmission detection system.

A beam expander (lens L7 and lens L8) expands the beam diameter of illumination light IL emitted from a light source 1 (Ar laser or the like) and the illumination light IL thus expanded enters an oscillating mirror (half mirror) 4 located on the rear focal plane FI2 of an objective lens L3. The illumination light IL reflected by the oscillating mirror 4 is incident to the objective lens L3.

The position of mask R is adjusted so that the front focal plane of the objective lens L3 may be coincident with a patterned surface with pattern PA of the mask. Thus, the objective lens L3 focuses the illumination light IL on the mask R to form an illumination region in the form of a spot on the mask. (It is noted that FIG. 1 does not illustrate optical paths of the illumination light IL from the objective lens L3 to the mask R, optical paths of regularly transmitted light by the mask R from the mask R to a lens L1, and optical paths of the illumination light regularly reflected by the mask R to a lens L5.)

The oscillating mirror 4 has a rotational axis parallel to the x-axis (which is an axis normal to the plane of the drawing), and a driving system MO composed of a motor etc. rotates the oscillating mirror 4 with respect to the optical axis AX about the rotational axis. The driving system MO rotates the oscillating mirror 4 to effect scanning in the y-direction with the illumination light IL. The objective lens L3 is of a telecentric system. Therefore, the illumination light IL is incident to the mask almost in parallel with the optical axis AX even if the oscillating mirror 4 causes a change of the position of illumination with the illumination light IL on the mask R. FIG. 1 shows an example in which the mask is scanned in the y-direction from a scanning point PL to a scanning point PR with the illumination light IL.

Meanwhile, the apparatus of FIG. 1 is provided with a light receiving optical system (L3, L4, L5, L6) for receiving the reflected light from the mask R. These lenses L3, L4, L5, L6 are arranged along the optical axis AX.

The objective lens L3 (a lens of focal length $f_3$) and the lens L4 (a lens of focal length $f_4$) are positioned so that the rear focal plane of the objective lens may coincide with the front focal plane of the lens L4. Thus, the objective lens L3 and lens L4 compose a double diffraction optical system. On a Fourier transform plane FI2 there appears a Fourier transform of amplitude distribution of light waves on the object plane ob accordingly. This means that a Fourier transform of amplitude distribution of diffracted light (reflected light) from the pattern PA of the mask disposed on the object plane ob is obtained on the Fourier transform plane FI2.

Further, an image plane IM2 conjugate with the object is formed on the rear focal plane of the lens L4. On the Fourier transform plane FI2 there appears a Fourier transform of amplitude distribution of light waves on the image plane IM2. The lens L5 and lens L6 also compose a double diffraction optical system, so that a spectrum (Fourier diffraction image) conjugate with that on the Fourier transform plane FI2 is obtained on a Fourier transform plane FI3 while an image conjugate with the image formed on the image plane IM2 is obtained on an image plane IM3. A spatial filter S2 is located on the Fourier transform plane FI3 (as detailed hereinafter).

The reason why such two sets of double diffraction optical systems are connected in series is that it is difficult to locate the spatial filter on the Fourier transform plane FI2 because the oscillating mirror MO is positioned thereon in order to optically scan the object plane ob with the beam spot in the present embodiment.

Figure 2A:
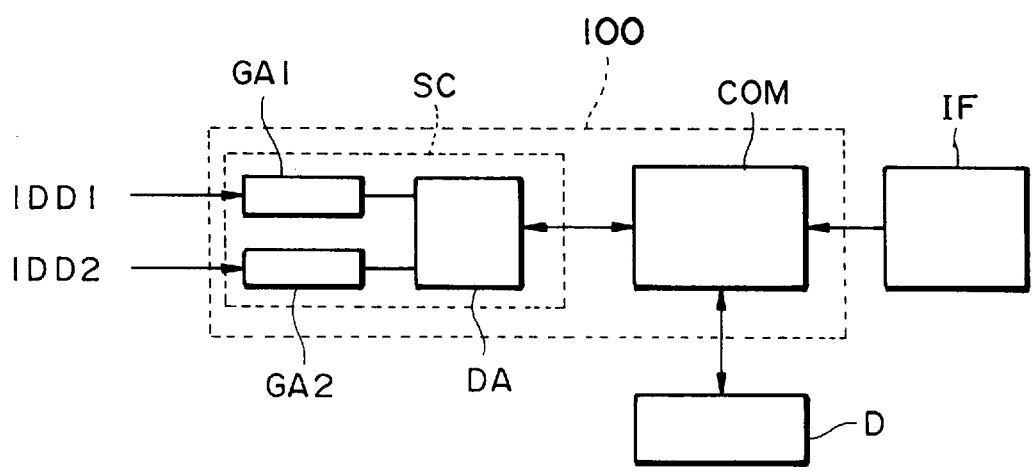
FIG. 2A and FIG. 2B are drawings to show examples of a signal processing system in the apparatus of FIG. 1.
Figure 2B:
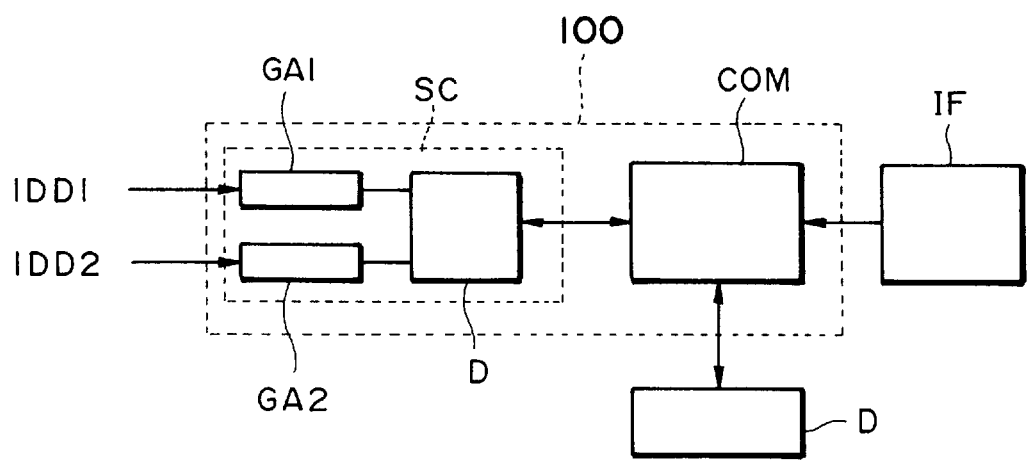

A light receiving surface of a one-dimensional photoelectric conversion element ID2 is positioned on the image plane IM3, and a signal IDD2 from the photoelectric conversion element ID2 is sent to a main control system 100 (FIGS. 2A and 2B).

As described above, the light receiving optical system (L3, L4, L5, L6) and photoelectric conversion element ID2 compose the reflection detection system.

Next explained is the transmission detection system.

On the opposite side to the reflection detection system with respect to the mask R, the lens L1 (a lens of focal length $f_1$) and the lens L2 (a lens of focal length $f_2$) are arranged along the optical axis AX. The illumination light IL having passed through the mask R is incident to a photoelectric conversion element ID1 through the lenses L1, L2. The lens L1 is positioned so that the front focal plane of the lens L1 may nearly coincide with the pattern surface PA of mask. The image plane IM1 is formed on the rear focal plane of lens L2, and the photoelectric conversion element ID1 is positioned so that this image plane IM1 may coincide with the light receiving plane of the photoelectric conversion element ID1.

Accordingly, these lenses L1, L2 also constitute a double diffraction optical system, so that a Fourier transform of amplitude distribution of light waves on the object plane ob is obtained on a Fourier transform plane FI1 and an image conjugate with that on the object plane ob is obtained on the image plane IM1. A spatial filter S1 is provided on the Fourier transform plane FI1 (as detailed hereinafter). As described above, the light receiving optical system (L1, L2) and photoelectric conversion element IDI compose the transmission detection system.

The objective lenses L1, L3 form a telecentric optical system, so that the illumination light IL is always incident at angle $\theta_0$ relative to the normal line to the objective plane ob (which is a line parallel to the optical axis AX) to the mask R during spot scan.

FIG. 1 illustrates the regularly transmitted light (the zeroth-order diffracted light) 11 having passed through the scanning region PR-PL of mask R along the optical axis AX, rays 12 occurring as transmitted by the mask R and rays 16 occurring as reflected by the mask R when the illumination light IL illuminates the scanning point PL, and rays 13 occurring as transmitted by the mask R and rays 15 occurring as reflected by the mask R when the illumination light IL illuminates the scanning point PR. These rays 12, 13, 15, 16 are rays each making an angle θm relative to the normal line to the object plane ob (the line parallel to the optical axis AX).

The mask R is held by a mask stage RST, and a moving mechanism DV moves the mask stage RST in the y-direction in parallel with the xy plane across the optical axis AX (along a light scanning line in the y-direction) as always positioning the pattern-scribed surface PA in the object plane ob of the objective lenses L3, L1. Inspection of a predetermined inspection area (two-dimensional region) of the mask R becomes possible by optical scanning with movement of the oscillating mirror 4 and by movement of the mask R by the moving mechanism DV. The main control system 100 totally controls the entire apparatus, including control of movement of the oscillating mirror 4, control of movement of the mask R by the driving mechanism DV, processing of signals from the photoelectric conversion elements ID1, ID2, and so on.

The main control system 100 of FIG. 1 is next explained with reference to FIGS. 2A and 2B.

In FIGS. 2A and 2B, the main control system 100 has a signal processing circuit SC including amplifiers for amplifying respective signals IDD1 and IDD2 as receiving the signal IDD1 output from the photoelectric conversion element ID1 and the signal IDD2 output from the photoelectric conversion element ID2, and adjusting circuits GA1, GA2 for adjusting gains of the respective amplifiers; a main computer COM; an input device IF through which information such as the inspection area is input; and a display Dp for displaying an inspection result of mask defect or the like. Here, FIG. 2A shows an example in which a differential amplifier DA obtains a difference between the signals gain-adjusted and inspection of mask defect is carried out based thereon. In contrast, FIG. 2B shows an example in which a divider D obtains a ratio of the signals gain-adjusted and inspection of mask defect is carried out based thereon.

The input device IF is a keyboard, a mouse, a light pen, a floppy disk driver, a bar code reader, or the like. For example, an operator inputs information such as setting values of amplification gains for the signals IDD1 and IDD2 based on information about transmittance of mask and reflectivity of pattern on the mask, inspection sensitivity, inspection area, and so on, through the keyboard (input device IF) into the computer COM. The computer COM outputs the setting values of amplification gains (gains) for the signals IDD1 and IDD2, based on these information thus input, to the signal processing circuit SC.

The transmission image signal IDD1 and reflection image signal IDD2 output from the two photoelectric conversion elements ID1, ID2 are input into the signal processing circuit SC. The signal processing circuit SC adjusts signal intensity of the two signals with the respective gains set based on the information from the computer COM. Adjustment amounts of the gains are so determined as to make zero a difference signal between the photoelectric signal of the reflected light and the photoelectric signal of the transmitted light from the circuit pattern, according to the principle as will be explained hereinafter referring to FIG. 26 to FIG. 28. Next, the signal processing circuit SC performs subtraction or takes a ratio between the two signals after gain-adjusted, thereby obtaining a signal IDD3. The signal processing circuit SC binarizes this signal IDD3 by a window comparator circuit in the signal processing circuit SC, using at least one of two threshold values THH, THL, as will be explained in the section of the principle. In more detail, the signal processing circuit outputs "1" to the computer COM when the signal IDD3 is greater than the threshold value THH; it outputs "0" to the computer COM when the signal IDD3 is smaller than the threshold value THL. The computer COM determines that a mask defect was detected if the signal processing circuit SC outputs the logic "1" (or when it outputs a binarized result with at least one of the threshold values THH, THL); the computer determines that no mask defect was detected (or that the signal obtained is only a signal from the circuit pattern or a signal from the glass surface of the mask R) when the signal processing circuit outputs the logic "0."

The computer COM maps the detection result of mask defect, based on the information on the detection result of mask defect and the information on the X-directional position of the detection light IL and the Y-directional position of mask R, and displays it on the display D.

The signal processing circuit SC can also correct the gain setting values by obtaining a difference between reflectivity and transmittance of a mask defect from the signal intensity of two signals.

The spatial filters S1, S2 are next explained with reference to FIGS. 3A and 3B.

Figure 3A:
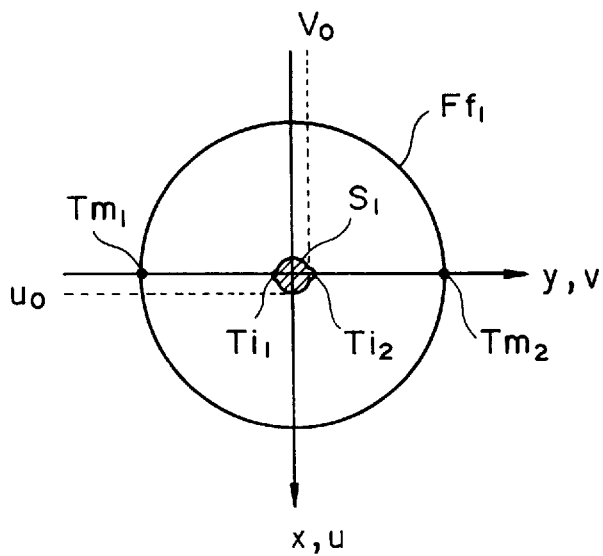
FIGS. 3A and 3B are drawings to show the spatial filters S1, S2 used in the apparatus of FIG. 1.
Figure 3B:
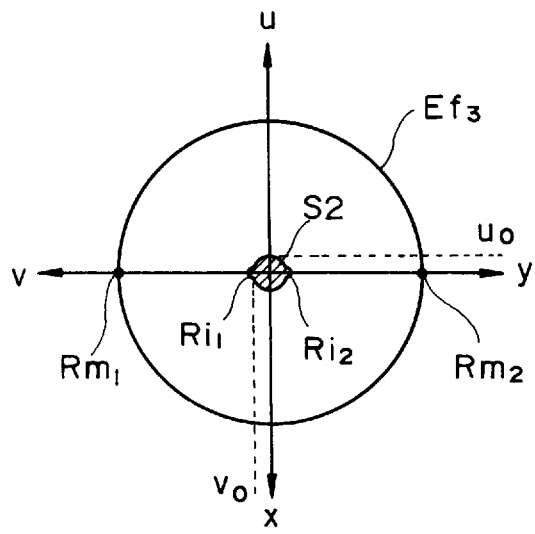

FIGS. 3A and 3B are drawings to show the Fourier transform planes formed in the respective light receiving systems and the spatial filters provided thereon. Region Ff1 in FIG. 3A is a circular region Ff1 on the Fourier transform plane FI1, defined by the lenses L1, L2. Region Ff2 in FIG. 3B is a circular region Ff2 on the Fourier transform plane FI3 (as well as FI2), defined by the lenses L3, L4, L5, L6. The region Ff1 represents a region where the light from the mask R, which can reach the photoelectric conversion element ID1, passes, while the region Ff2 represents a region where the light from the mask, which can reach the photoelectric conversion element ID2, passes. It is noted that the xy coordinate system of FIGS. 3A and 3B corresponds to the xy coordinate system of FIG. 1.

In the present embodiment a Fourier spectrum (Fourier diffraction image) through the region Ff1 on the Fourier transform plane FI1 in FIG. 3A is made coincident with that through the region Ff2 on the Fourier transform plane FI2 in FIG. 3B.

For this purpose, the numerical aperture and magnification of the lenses L3, L4, L5, L6 and the numerical aperture and magnification of the lenses L1, L2 are so determined that the transmitted light and the reflected light may have the same maximum angle θm relative to the optical axis AX, of rays emerging from the object plane ob, which corresponds to the maximum spatial frequency that can pass through the Fourier transform planes FI1, FI3.

As shown in FIG. 3A, the spatial filter S1 for shielding the zeroth-order diffracted light (transmitted light 11) of the illumination light IL in the region Ff1 is provided in the region Ff1 on the Fourier transform plane. As shown in FIG. 3B, the spatial filter S2 for shielding the zeroth-order diffracted light (reflected light 14) of the illumination light IL in the region Ff2 is provided in the region Ff2 on the Fourier transform plane. In FIGS. 3A and 3B, "uv" represents the coordinate system on the Fourier transform plane.

The diffracted light 12, 13 occurring from the mask R (or occurring at the circuit pattern or at a mask defect on the mask) travels through regions indicated by Tm1, Tm2 on the Fourier transform plane FI1 (on the region Ff1) while the diffracted light 15, 16 occurring as reflected by the mask R (occurring as reflected by the circuit pattern or a mask defect on the mask) travels through regions indicated by Rm1, Rm2 on the Fourier transform plane FI3 (on the region Ff2). The points Rm1, Rm2, Tm1, Tm2 are located at the limits (outermost regions) of the regions Ff1, Ff2.

Accordingly, transmitted ray components from the mask R making the angle θm relative to the optical axis AX (where the angle between the principal rays of transmitted light beam and the optical axis AX is θm) are limit rays that can pass through the region Ff1 on the Fourier transform plane FI1.

This means that the angle θm represents the size of the region Ff1. Similarly, reflected ray components from the mask R making the angle θm relative to the optical axis AX (where the angle between the principal rays of reflected light beam and the optical axis AX is θm) are limit rays that can pass through the region Ff2 on the Fourier transform plane FL2, and the angle θm represents the size of the region Ff2.

Although FIG. 1 shows that intersections between the Fourier transform planes FI1 and FI3 and the zeroth-order diffracted light (transmitted and reflected) are points, the intersections on the Fourier transform planes have some size corresponding to an angle $(\theta_0)$ in fact because the illumination light IL is incident to the mask R at the predetermined angle $(\theta_0)$ or with NA of beam.

The foregoing described that the spatial filters S1, S2 shielded the zeroth-order diffracted light. This means that when the zeroth-order diffracted light has a spread of ± the angle $\theta_0$ relative to the optical axis AX (which correspond to the size of the zeroth-order diffracted light on the Fourier transform plane), the spatial filter S1 shields rays of angles smaller than the angle $\theta_0$ with respect to the normal line to the object plane ob out of rays occurring from the object plane ob and traveling in the transmission direction, but transmits rays having angles between the angles $\theta_0$ and $\theta_m$. Similarly, the spatial filter S2 shields rays of angles smaller than the angle $\theta_0$ relative to the normal line to the object plane ob out of rays occurring from the object plane ob and traveling in the reflection direction, but transmits rays having angles between the angles $\theta_0$ and $\theta_m$.

In FIGS. 3A and 3B, the diameter of the circular spatial filters S1, S2 on the Fourier transform planes is expressed by $2u_0$, $(=2v_0)$ in the uv coordinate system, and angle $2\theta_0$ corresponds to this diameter $2u_0$ $(=2v_0)$.

Points Ti1, Ti2 represent points where the zeroth-order diffracted light 11 (transmitted light) impinges on the Fourier transform plane FI1 of FIG. 1. Further, points Ri1, Ri2 represent points where the zeroth-order diffracted light 14 (reflected light: rays having the same angle components as the rays 11) impinges on the Fourier transform plane FI3 after emerging from the object plane ob.

Next explained in detail are the difference between the two signals ID1, ID2 and the adjustment of gains shown in FIG. 1.

Letting α be an amplitude reflectance at the circuit pattern portion on the mask R to cause reflected and scattered light on the object plane ob and $f_1(x, y)$ be a function of amplitude distribution of reflected light, a distribution of reflectance is indicated by $\alpha f_1(x, y)$. Letting β be an amplitude transmittance at a portion without circuit pattern to cause transmitted and scattered light and $f_2(x, y)$ be a function of amplitude distribution of transmitted light, a distribution of transmittance is expressed by $\beta f_2(x, y)$. There is the following relation of Eq. (22) between them.

$$1 - f_1(x,y) = f_2(x,y) \quad (22)$$

Further, letting $f_0(x, y)$ be an amplitude distribution of light waves of an incident beam spot, a Fourier spectrum (Fourier diffraction image) is expressed by Eq. (23) or (24).

A spectrum on the Fourier transform plane FI3 is given as follows.

$$FT^-[\alpha f_1(x,y) \times f_0(x,y)] = FT^-[\alpha f_1(x,y)] \quad (23)$$
$$= \alpha F_1(u,v) * F_0(u,v)$$
$$= \alpha F_1(u,v)$$

$$FT^-[\alpha f_1 ac(x,y) \times f_0(x,y)] = \alpha F_1 ac(u,v) * F_0(u,v) \quad (24)$$
$$= \alpha F_1 ac(u,v)$$

A spectrum on the Fourier transform plane FI1 is given as follows.

$$FT^-[\beta f_2(x,y) \times f_0(x,y)] = FT^-[\beta f_2(x,y)] \quad (25)$$
$$= \beta F_2(u,v) * F_0(u,v)$$
$$= \beta F_2(u,v)$$

$$FT^-[\beta f_2 ac(x,y) \times f_0(x,y)] = \beta F_1 ac(u,v) * F_0(u,v) \quad (26)$$
$$= \beta F_1 ac(u,v)$$

Here, there are the relations of Eqs. (27), (28), and (29) for $F_0(u, v)$, $F_1(u, v)$, and $F_2(u, v)$.

$$FT^-[f_0(x,y)] = F_0(u,v) = \begin{cases} A & \sqrt{u^2+v^2} \leq \sqrt{u_0^2+v_0^2} \\ 0 & \sqrt{u^2+v^2} > \sqrt{u_0^2+v_0^2} \end{cases} \quad (27)$$

$$FT^-[f_1(x,y)] = F_1(u,v) \quad (28)$$

$$FT^-[f_2(x,y)] = F_2(u,v) \quad (29)$$

Eq. (30) holds from the Babinet's principle.

$$F'_1(u,v) + F'_2(u,v) = F_0(u,v) \quad (30)$$

Here, the functions $F_1'ac(u, v)$, $F_2'ac(u, v)$ are newly expressed by Eqs. (31), (32).

$$F'_1 ac(u,v) = \begin{cases} F'_1(u,v) & (\sqrt{u^2+v^2} > \sqrt{u_0^2+v_0^2}) \\ 0 & \sqrt{u^2+v^2} \leq \sqrt{u_0^2+v_0^2} \end{cases} \quad (31)$$

$$F'_2 ac(u,v) = \begin{cases} F'_2(u,v) & (\sqrt{u^2+v^2} > \sqrt{u_0^2+v_0^2}) \\ 0 & \sqrt{u^2+v^2} \leq \sqrt{u_0^2+v_0^2} \end{cases} \quad (32)$$

From Eqs. (27) and (30), Eq. (33) results.

$$F'_1 ac(u,v) + F'_2 ac(u,v) = 0 \quad (33)$$

Therefore, the Fourier spectra passing in the present embodiment are expressed by Eqs. (34) and (35).

$$\text{Spectrum passing through FI1} = \beta F_2'ac(u, v) \quad (34)$$

$$\text{Spectrum passing through FI3} = \alpha F_1'ac(u, v) \quad (35)$$

From Eq. (33), they are equal to each other except for their coefficients. FIGS. 29A–29E shows states of $f_1(x)$, $f_2(x)$, $F_1'(u)$, $F_2'(u)$ in the one-dimensional case. FIGS. 29A–29E show an example in which line: pattern is 1:1.

Further, images appearing on the image planes $IM_3$, $IM_1$ are expressed by Eqs. (36), (37).

$$\text{Image on the image plane } IM_1 = FT^-[\beta F_2'ac(u,v)] \quad (36)$$
$$= \beta f_2 ac(x,y)$$
$$= -\beta f_1'ac(x,y)$$

$$\text{Image on the image plane } IM_3 = FT^-[\alpha F_1'ac(u,v)] \quad (37)$$
$$= \alpha f_1'ac(x,y)$$

These are also equal to each other except for their coefficients.

Since an image is output by light intensity, electric outputs IDD1, IDD2 are expressed as follows.

$$k \cdot IDD1 = k[\beta f''_2(x,y)]^2 = k\beta^2[(f'_1(x,y)]^2 \quad (38)$$

$$l \cdot IDD2 = l[\alpha f''_1(x,y)]^2 = l\alpha^2[(f'_1(x,y)]^2 \quad (39)$$

Here, k, l are gains of the amplifiers. From Eqs. (38) and (39), same outputs can be obtained if adjustment is made so as to satisfy Eq. (40).

$$k\beta^2 = l\alpha^2 \quad (40)$$

The output signals IDD1, IDD2 are input into the signal processing circuit SC in FIGS. 2A and 2B, and a mask defect can be readily detected if the gains k, l of the sensors are set so as to satisfy Eq. (40). Eq. (40) indicates that Eq. (41) will hold if optimization is made for the reflectance $\alpha$ of the circuit pattern and the transmittance $\beta$ of the glass portion of mask R.

$$k \cdot IDD1 - l \cdot IDD2 = 0 \quad (41)$$

Namely, Eq. (41) becomes not to hold if either one of reflectance and transmittance of a mask defect is different from $\alpha$ or $\beta$. Therefore, a necessary arrangement is such that a signal IDD3 like (42) is made and it is binarized by an appropriate threshold value (THH, THL defined by the window comparator).

$$IDD3 = k \cdot IDD1 - l \cdot IDD2 \quad (42)$$

As apparent from Eq. (42), the present invention is arranged to effect subtraction between a transmitted dark field image and a reflected dark field image so as to erase an image of the defectless circuit pattern, thereby enabling to extract only a mask defect if either the amplitude reflectance or the amplitude transmittance thereof on the photomask is different from that of the defectless circuit pattern.

Next explained is the second embodiment of the present invention. The apparatus of the present embodiment is constructed substantially in the same structure as the inspection apparatus of FIG. 1 in the first embodiment except that spatial filters S11, S22 are added (so as to be overlaid on the spatial filters S1, S2) on the Fourier transform planes FI1, FI3, as shown in FIGS. 4A and 4B, in addition to the spatial filters S1, S2.

Figure 4A:
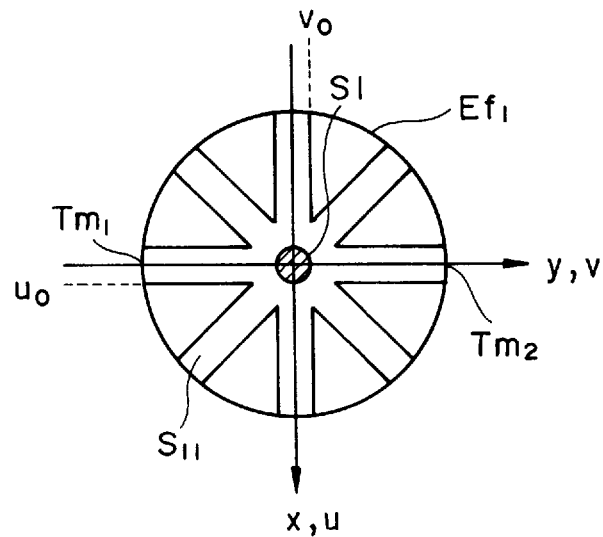
FIGS. 4A and 4B are drawings to show the spatial filters in the second embodiment of the present invention.
Figure 4B:
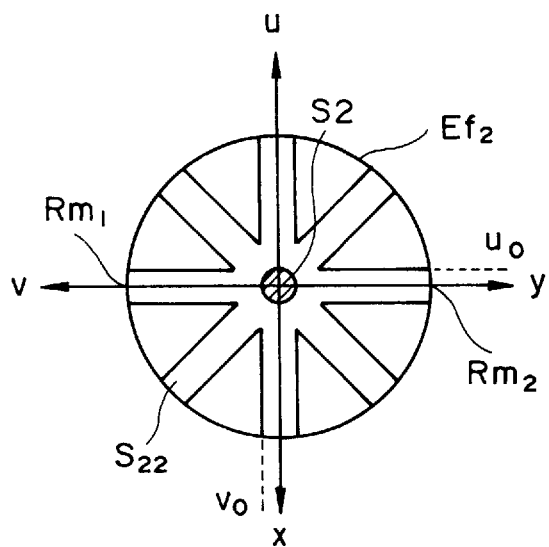

In FIGS. 4A and 4B, the spatial filters S11, S22 interrupt (or shield) Fourier transform patterns occurring when the illumination light IL is incident to straight line portions of pattern making angles of 0°, 45°, 95°, and 135° relative to the x-axis, which are main constituents of the circuit pattern on the object plane ob. Each of the spatial filters S11, S22 is composed of three strips intersecting at angles of 45° about the optical axis AX. The width of the three strips is made coincident with the diameter ($=2u_0=2v_0$) of the spatial filter S1 corresponding to the size of the Fourier transform spectrum of the illumination light occurring when no circuit pattern is present on the object plane ob (which is the size of the passing region in the Fourier transform plane FI1, of the zeroth-order diffracted light (transmitted light) of the illumination light IL having passed through the mask R) or the diameter ($=2u_0=2v_0$) of the spatial filter S2 corresponding to the size of the Fourier transform spectrum of the illumination light occurring when the entire surface of the object plane ob is covered with a uniform and reflective circuit-pattern-scribing material (the size of the passing region in the Fourier transform plane FI3, of the zeroth-order diffracted light (reflected light) of the illumination light IL reflected by the mask R), which can stop the Fourier transform pattern (diffraction image) of the diffracted light occurring from the straight line portions.

The spatial filters S11, S22 stop the Fourier transform patterns occurring from the straight line portions of the circuit pattern, but transmit Fourier transform spectra (diffraction images) of the other spatial frequencies. Examples of the Fourier transform spectra passing are a Fourier transform spectrum of a mask defect composed of random curves rather than straight line portions, and a part of a Fourier spectrum of cell circuit patterns having two-dimensional periodic structure.

The inspection apparatus provided with the spatial filters of FIGS. 4A and 4B as in the second embodiment can interrupt the most of the scattered light occurring from the circuit pattern, so that it can decrease a quantity of light of image of the circuit pattern incident to the photoelectric conversion elements. Therefore, as compared with the inspection apparatus of FIG. 1 provided with only the spatial filters S1, S2 shown in FIGS. 3A and 3B, the apparatus can improve the contrast of an image of mask defect relative to an image of the circuit pattern, thereby enabling to detect a microscopic and low-level-difference mask defect more easily.

Figure 5A:
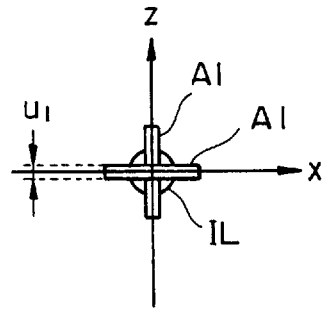
FIGS. 5A, 5B, and 5C are drawings to illustrate the third embodiment of the present invention.
Figure 5B:
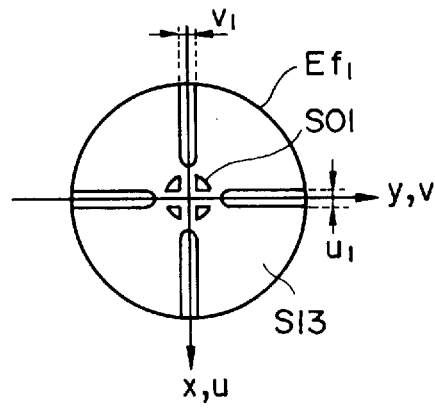
Figure 5C:
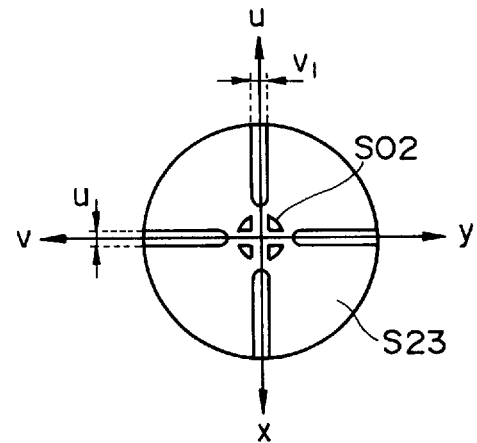

Next explained is the third embodiment of the present invention. FIGS. 5A, 5B, and 5C are drawings to show a light shielding member and spatial filters used in the inspection apparatus of the third embodiment of the present invention. The inspection apparatus in the present embodiment is different from the apparatus of FIG. 1 in the spatial filters S13, S23, and the light shielding strip $A_1$ provided in the optical path of the illumination light IL. Since the other portions are the same as in the apparatus of FIG. 1, the detailed description of the apparatus structure is omitted. The light shielding strip $A_1$ is located in the optical path of the illumination light IL incident to the mask R in the vicinity of the Fourier transform plane FI2. FIG. 5A is a drawing to show the light shielding member $A_1$. As illustrated, the light shielding member $A_1$ is composed of two light shielding elements intersecting in a cross pattern in a plane nearly perpendicular to the illumination light IL. The illumination light IL passing through the light shielding member $A_1$ is split into four beams and then is condensed on the object plane ob to illuminate a point. In FIG. 5B, S01 indicates a Fourier transform spectrum of transmitted illumination light beam occurring when no circuit pattern of mask R exists, while S02 in FIG. 5C indicates a Fourier transform spectrum of reflected illumination occurring when the circuit-pattern-scribed surface of the photomask 1 is covered with a uniform and reflective circuit-pattern-scribing material.

The spatial filters S13, S23 transmit light beams of spatial frequencies in cross pattern slits of width $v_1$ along the u-axis and the v-axis, which are regions where no Fourier spectrum S01, S02 of illumination light beam (diffraction images on the Fourier transform planes) is present, but interrupt light beams of the other spatial frequencies.

The spatial filters S13, S23 interrupt the most of the Fourier transform pattern occurring due to the circuit pattern, but transmit a part of the Fourier transform pattern occurring due to a mask defect. Accordingly, they can lower the intensity of circuit pattern image and improve the contrast of mask defect image. Further, the spatial filters S13, S23 also stop the Fourier transform pattern of cell circuit patterns in the two-dimensional periodic structure, which is transmitted by the spatial filters S11, S22 shown in FIGS. 4A and 4B, and thus, improve the contrast of a mask defect in such circuits.

Next explained is the fourth embodiment of the present invention. The apparatus of the present embodiment is different from the apparatus of FIG. 1 in that the apparatus of the present embodiment excludes the lens L2 and lens L6 and in that the detectors ID1, ID2 are located on the Fourier transform planes FI1, FI3 and the detectors ID1, ID2 are sensors of a unit pixel. The other arrangement is the same as that of the apparatus of FIG. 1, and the detailed description of the apparatus structure using the drawings is omitted herein.

The present embodiment is also provided with the spatial filters S1, S2 for shielding the Fourier transform patterns of the illumination light on the Fourier transform planes FI1, FI3, similarly as in FIG. 1. Therefore, the Fourier spectra on the Fourier transform planes FL1, FL3 are equal to each other except for their coefficients from Eqs. (34) and (35).

Thus, the photoelectric conversion element ID1, ID2 provided on the Fourier transform plane FL1, FL3 photoelectrically converts a light quantity obtained by integration of an overall spectrum of light passing through the region except for the region where the spatial filter S1, S2 is provided in the spatial frequency region Ff1, Ff2, shown in FIG. 3A, 3B, and then outputs an output IDD1, IDD2. These are expressed by Eqs. (43), (44).

$$k \cdot IDD1 = K|\beta F''_2(u,v)|^2 \qquad (43)$$

$$l \cdot IDD2 = l|\alpha F''_1(u,v)|^2 \qquad (44)$$

Supposing k, l expressing the gains of amplifiers are those satisfying the relation $k\beta^2=l\alpha^2$ as in Eq. (40), same outputs are obtained with a circuit pattern having no mask defect. Here, a mask defect can be detected by forming the signal IDD3 in the same manner as in Eq. (42) and binarizing it by an appropriate threshold value (THH, THL). In this manner the present embodiment generates the signal IDD3, which becomes zero in the case of no mask defect, by subtraction between the transmitted light quantity and the reflected light quantity on the Fourier transform planes, thereby enabling to detect a mask defect easily.

In the present embodiment ID1, ID2 output the outputs IDD1, IDD2, each expressing a light quantity determined to be a single value depending upon the illumination position of the illumination light beam IL. The signal processing unit SC performs the above-described subtraction and binarization processing of signal, and the computer COM controls the sequence of inspection operation. The computer COM also controls the translational movement of the photomask R, scanning of the oscillating mirror 4, and so on, and obtains a position of deposition of a mask defect, based on these positional information and detection information of mask defect.

Figure 6:
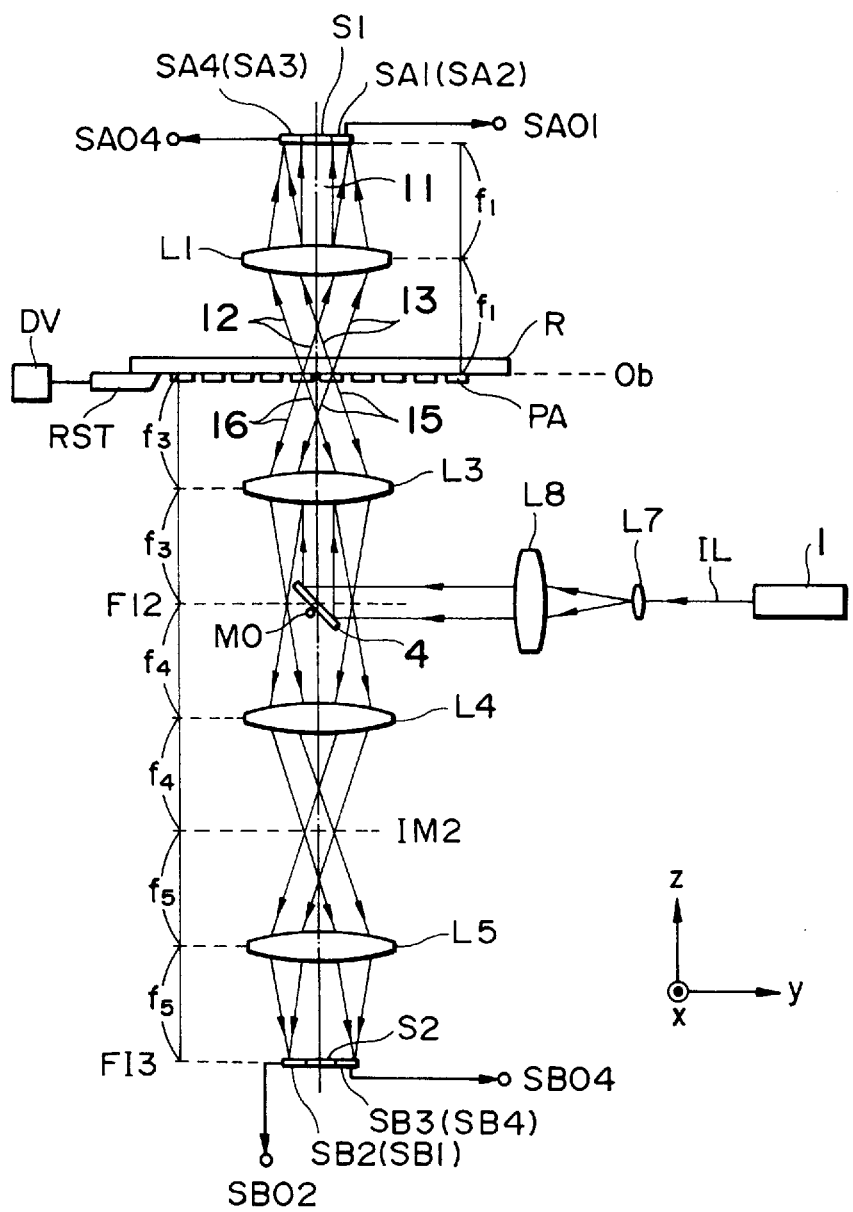
FIG. 6 is a drawing to show the schematic structure of a mask defect inspection apparatus suitable for the fifth embodiment of the present invention.

FIG. 6 shows the inspection apparatus of the fifth embodiment of the present invention. The apparatus of the present embodiment is different from the apparatus of the fourth embodiment in the number of photoelectric conversion elements and the signal processing system resulting therefrom.

The photoelectric conversion elements for transmitted light $S_{A1}$, $S_{A2}$, $S_{A3}$, $SA_{A4}$ and photoelectric conversion elements for reflected light $S_{B1}$, $S_{B2}$, $S_{B3}$, $S_{B4}$ are disposed so that their light detecting surfaces (light receiving surfaces) are positioned on the Fourier transform planes FI1, FI3. These photoelectric conversion elements are paired as $S_{A1}$ and $S_{B1}$, as $S_{A2}$ and $S_{B2}$, as $S_{A3}$ and $S_{B3}$, and as $S_{A4}$ and $S_{B4}$, and are arranged so as to satisfy Eq. (33) in the regions of respective light receiving surfaces.

Figure 7A:
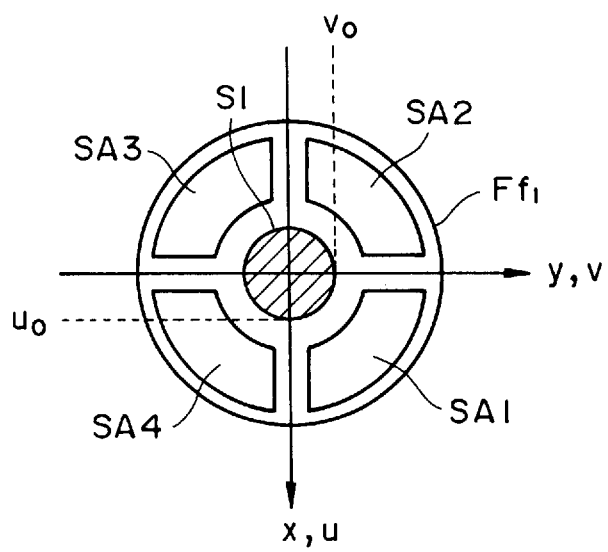
FIGS. 7A and 7B are drawings to show the photoelectric conversion elements used in the apparatus of FIGS. 5A, 5B, and 5C.
Figure 7B:
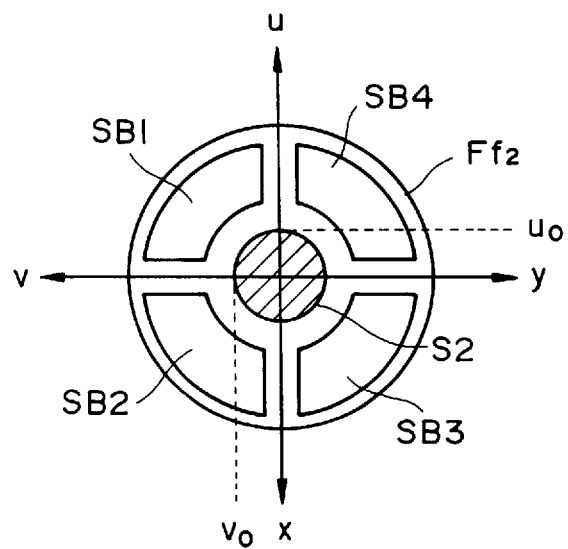

FIG. 7A is a drawing to show the arrangement of photoelectric conversion elements $S_{A1}$, $S_{A2}$, $S_{A3}$, $S_{A4}$ on the Fourier transform plane, and FIG. 7B is a drawing to show the arrangement of photoelectric conversion elements $S_{B1}$, $S_{B2}$, $S_{B3}$, $S_{B4}$ on the Fourier transform plane.

Figure 8:
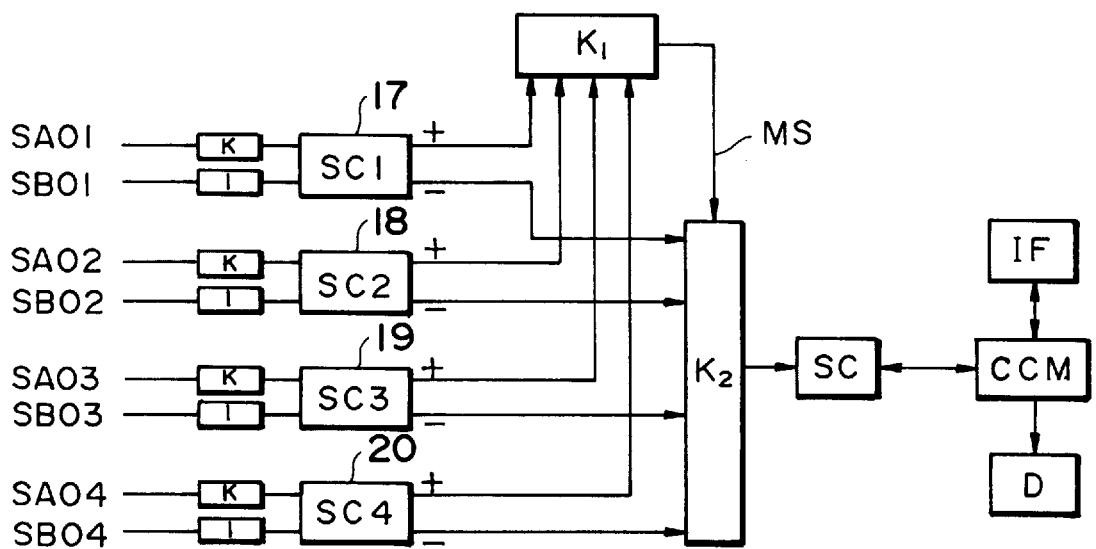
FIG. 8 is a drawing to show the signal processing system used in the apparatus of FIGS. 5A, 5B, and 5C.

Namely, in the uv orthogonal coordinate system in FIGS. 7A and 7B, two regions in a same quadrant are paired with each other. FIG. 8 is a drawing to show the signal processing system in the present embodiment. In FIG. 8 four pairs of photoelectric conversion outputs are input into four signal processing circuits 17, 18, 19, 20 to be subjected to addition and subtraction processing in the respective circuits. In the drawing, a plus signal represents an addition output and a minus signal a subtraction output.

Since the four pairs of photoelectric conversion elements each satisfy Eq. (33), a mask defect can be detected from signals obtained by binarizing four signals with appropriate threshold value (THH, THL), defining $S_{c1}$ to $S_{c4}$ as follows.

$$S_{c1-}=k \cdot S_{A1}-1 \cdot S_{B1} \quad (45)$$

$$S_{c2-}=k \cdot S_{A2}-1 \cdot S_{B2} \quad (46)$$

$$S_{c3-}=k \cdot S_{A3}-1 \cdot S_{B3} \quad (47)$$

$$S_{c4-}=k \cdot S_{A4}-1 \cdot S_{B4} \quad (48)$$

Incidentally, the Fourier transform spectrum of circuit pattern often has deviation on the Fourier transform plane. Utilizing this fact, the present embodiment can detect a finer and lower-level-difference mask defect by selecting a pair of photoelectric conversion elements with a smaller integral light quantity on their light receiving surfaces, of the Fourier transform spectrum of the circuit pattern.

In the fifth embodiment also, in the same manner as in the previous embodiments, a third photoelectric conversion signal is made by subtraction between the first photoelectric conversion signal and the second photoelectric conversion signal which repsectively present light quantities of the transmitted light and reflected light and the third photoelectric conversion signal is binarized with appropriate slice levels (THH, THL) to extract a signal of mask defect.

For performing such a method, the subtraction of signals needs to be carried out within the dynamic range of the photoelectric conversion elements. A photoelectric conversion element outputs a signal proportional to a light quantity, but the output signal has a minimum output value depending upon electrical noise and a maximum output value determined by the rated maximum. Normally, the dynamic range is defined as maximum output/minimum output, which is a specific value to each photoelectric conversion element. (Although the dynamic range thus defined represents a ratio, it is a usual practice to use it as an expression to represent a region.) A requirement to increase the light quantity of scattered light from a microscopic mask defect over the minimum output value is just to increase luminance of the illumination light IL. In this case, the light quantity of the scattered light from the circuit pattern also increases. If the quantity of the scattered light from the circuit pattern increases over the maximum output value, the third photoelectric conversion signal based on Eq. (42) becomes different from an ideal value, which impedes normal mask defect inspection.

In order to avoid the above phenomenon, the present embodiment is arranged to select a region with a small quantity of scattered light from the circuit pattern out of the four regions on the Fourier transform plane.

As described previously, the four pairs of photoelectric conversion outputs are input into the four signal processing circuits $S_{c1}$, $S_{c2}$, $S_{c3}$, $S_{c4}$ in FIG. 8 to be subjected to the addition and subtraction processing therein. In the same drawing, a plus sign represents an addition output $S_{c1+}$, $S_{c2+}$, $S_{c3+}$, $S_{C4+}$.

A minus sign represents a subtraction output $S_{c1-}$, $S_{c2-}$, $S_{c3-}$, $S_{c4-}$.

$$S_{c1+}=kS_{A1}+1S_{B1} \quad (49)$$

$$S_{c2+}=kS_{A2}+1S_{B2} \quad (50)$$

$$S_{c3+}=kS_{A3}+1S_{B3} \quad (51)$$

$$S_{c4+}=kS_{A4}+1S_{B4} \quad (52)$$

$S_{c1+}$, $S_{c2+}$, $S_{c3+}$, $S_{c4+}$ are expressed by Eqs. (49) to (52). The four addition outputs are input into a minimum value selecting unit $k_1$, which outputs an output selection signal $M_s$. A selector $k_2$ selects a subtraction output being the minimum on the basis of the addition output designated by the output selection signal $M_s$, and supplies it to the signal processing circuit SC. The signal processing circuit SC binarizes it with appropriate threshold values (THH, THL) and supplies a mask defect detection signal to the computer COM. It is also noted in this case that the arrangement may be modified to take a ratio of the signals gain-adjusted instead of taking a difference between the gain-adjusted signals, as explained with FIG. 2B.

The above operation can improve the dynamic range and permits a finer mask defect to be detected.

In the present embodiment the computer COM also controls the inspection operation, similarly as in the previous embodiments. The computer COM also controls the translational movement of mask R, scanning of the oscillating mirror 4, and so on. The computer COM maps the inspection result to display it on the display D. The input apparatus IF receives an input of contents of inspection from the operator, for example an inspection area, inspection sensitivity, or the like, and then transfers it to the computer COM.

The inspection apparatus of this embodiment has four photoelectric conversion elements in each of the Fourier transform planes FI1, FI3. It is noted that the regions to be occupied by the photoelectric conversion elements are not limited to those in this example. Further, the number of photoelectric conversion elements is not limited to four, either.

The sixth embodiment of the present invention is next explained.

Figure 9:
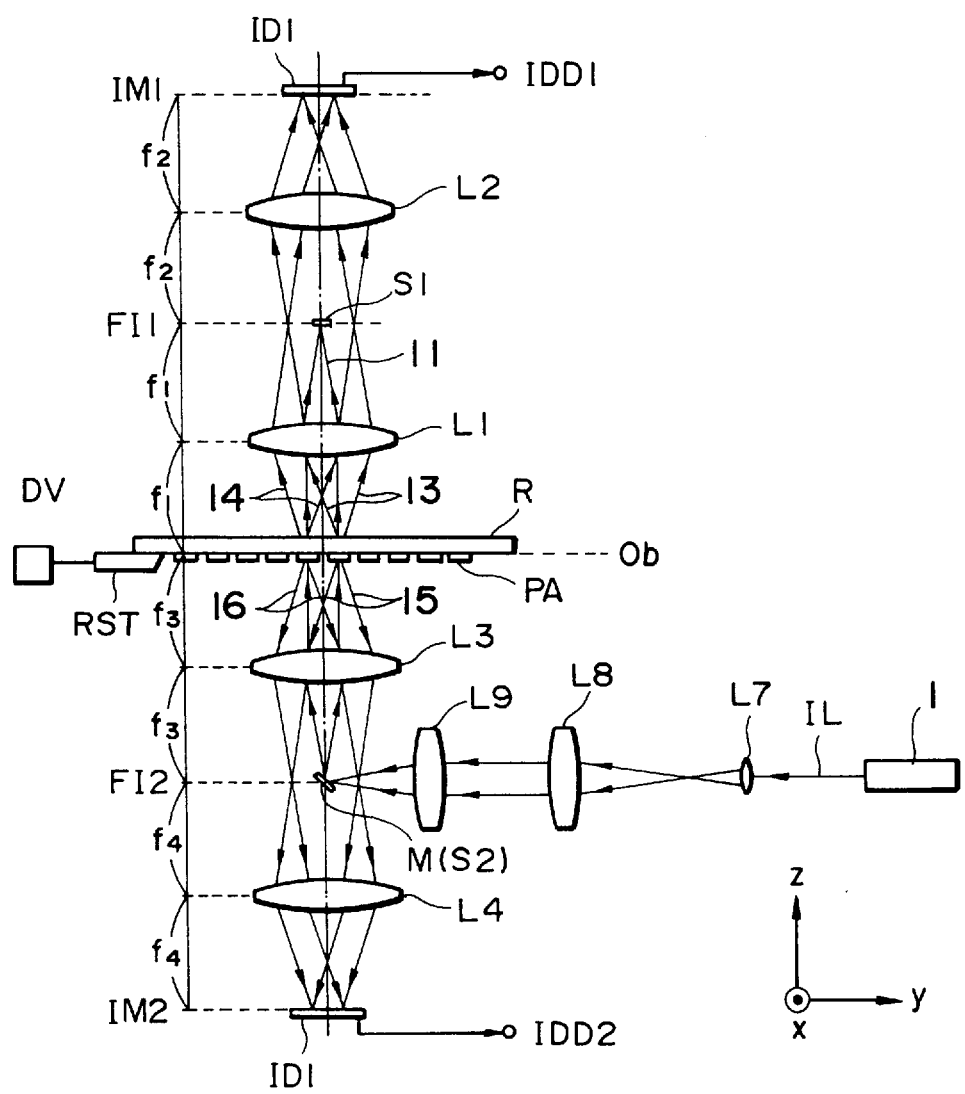
FIG. 9 is a drawing to illustrate the sixth embodiment of the present invention.

FIG. 9 is a drawing to show the inspection apparatus of the sixth embodiment of the present invention.

The illumination light IL emitted from the light source 1 passes through a group of lenses L7, L8, L9 to form a light spot focused on the mirror M disposed in the vicinity of the rear focal plane FI$_2$ of objective lens L3. The illumination light IL is reflected toward the objective lens L3 to be refracted by the objective lens L3 into parallel rays to illuminate the mask R. The lenses L3, L4, L1, L2 are arranged along the optical axis AX. The lenses L3, L4 compose a double diffraction optical system and the objective lens L3 is located at a position nearly equal to the focal length f3 from the object plane ob. The Fourier transform plane $FI_2$ is formed on the rear focal plane of the objective lens L3. An image plane $IM_2$ conjugate with the object plane ob is formed on the rear focal plane of the lens L4. The lenses L1, L2 also compose a double diffracting optical system and the objective lens L1 is located at a distance nearly equal to the focal length f1 from the object plane ob. The Fourier transform plane $FI_1$ is formed on the rear focal plane of the lens L1. The image plane $IM_1$ conjugate with the object plane ob is also formed on the rear focal plane of the lens L2.

The mask stage RST holds the mask R so that the circuit-pattern-scribed surface PA thereof, which is an inspected surface of mask R, may be located on the object plane ob. The illumination light IL illuminates the inside of the field of the objective lenses L3, L1.

When the pattern-scribed surface PA is totally covered with a uniform and reflective circuit-pattern-scribing material, the illumination light IL is reflected on the object plane ob to go back the light path it had come and then to form a Fourier transform pattern of the illumination light IL on the Fourier transform plane $FI_2$. When the amplitude distribution of light waves of the illumination light IL on the object plane is expressed by $f_0(x, y)$ and the Fourier transform pattern thereof by $F_0(u, v)$, the Fourier transform pattern $F_0(u, v)$ all is reflected by the mirror M toward the lens L3. Namely, the mirror M serves as the spatial filter $S_2$ for shielding the zeroth-order light in the inspection apparatus of FIG. 1. Rays pass through the region $Ff_2$ on the Fourier transform plane to reach the lens L4. If no circuit pattern is present in the pattern-scribed surface PA of mask R and when the amplitude distribution of light waves of the illumination light IL is $f_0(x, y)$, the Fourier transform pattern is formed on $FI_1$ to become $F_0(u, v)$.

Another zeroth-order-light shielding filter S1 is located on the Fourier transform plane $FI_1$. The filter S1 shields $F_0(u, v)$, but transmits rays in the other spatial frequency region $Ff_1$. The spatial frequency regions Ff1 and Ff2 are designed to transmit rays in the same frequency region.

For example, rays 13, 14, 15, 16, which correspond to the maximum spatial frequency in the spatial frequency regions Ff1, Ff2, make a same angle relative to the optical axis AX.

Supposing the reflectance distribution is $\alpha f_1(x, y)$ where $\alpha$ is the reflectance of the circuit part and the transmittance distribution is $\beta f_2(x, y)$ where $\beta$ is the transmittance, Eq. (22), Eq. (23), Eq. (24), Eq. (25), Eq. (26), and Eq. (27) to Eq. (37) hold, and same images of different amplitudes are formed on the image planes $IM_1$, $IM_2$.

Accordingly, the outputs IDD1, IDD2 from the photoelectric conversion elements $ID_1$, $ID_2$ are expressed by Eqs. (38), (39). Thus, a mask defect signal can be detected when the gains k, l of amplifiers are defined, for example, as in Eq. (40), the third output IDD3 is formed by Eq. (42), and it is binarized by an appropriate binarizing circuit (window comparator).

In the sixth embodiment, the photoelectric conversion elements are one-dimensional linear sensors and there is no need to use optical scanning by a scanner mirror or AOD.

The photoelectric conversion elements may be replaced by two-dimensional area sensors. The control of the inspection operation by computer COM is the same as in the other embodiments.

The first to sixth embodiments stated above are arranged to adjust the gains of amplifiers for amplifying two outputs in order to adjust the outputs from the photoelectric conversion elements ID1, ID2, but they may be modified to adjust the two outputs in such an arrangement that a plurality of ND filters or the like with different damping characteristics are disposed before the photoelectric conversion elements ID1, ID2 (on the mask side) so as to be retractable from the optical path.

The present invention is applicable to all mask defect inspection apparatus for photomask of the laser scanning type, and, in the case of the apparatus having an illumination system of oblique incidence, proper arrangement of light receiving element can equivalently attain the same effect as the light shielding effect of scattered light and diffracted light from the edges of the circuit pattern like a spatial filter.

The incident system in the first to sixth embodiments described above may be arranged as an oblique incident system for incidence of the illumination light IL oblique relative to the normal line to the mask R, and the optical axis of light receiving system may be arranged as inclined relative to the normal line to the mask R. Further, the both incidence system and light receiving system may be inclined relative to the mask R. In the apparatus structure shown in FIG. 6, the arrangement of photoelectric conversion elements located on the Fourier transform planes may be modified in such a manner that the spatial angle inside the photoelectric conversion elements located at the both ends (a spacing inside the photoelectric conversion elements on the Fourier transform planes) becomes nearly equal to the angle of the zeroth-order light ($2\theta_0$: corresponding to the size of the zeroth-order light on the Fourier transform plane), as disclosed in Japanese Laid-open Patent Applications No. 4-122042, No. 5-165196, No. 6-43111 and No. 6-94633. This arrangement stops the diffracted light from the circuit pattern from entering at least one of the plural photoelectric conversion elements, thus improving the detection accuracy of mask defect.

Next explained is the principle of the inspection method used in the above first to sixth embodiments.

Figure 10:
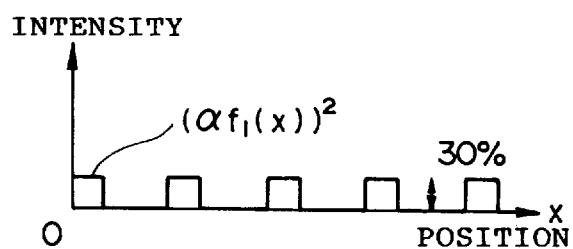
FIG. 10 to FIG. 25, FIG. 26A to FIG. 26C, FIG. 27A to FIG. 27C, FIG. 28A to FIG. 28C, and FIG. 29A to FIG. 29E are drawings to illustrate inspection principles in the embodiments according to the present invention.
Figure 11:
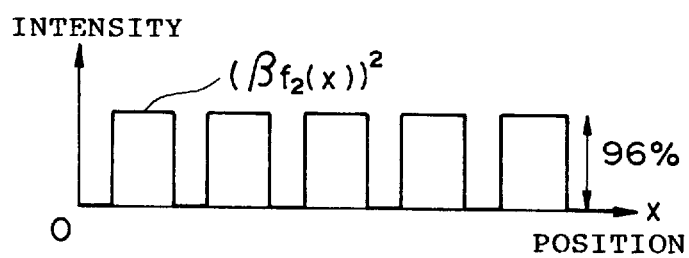
Figure 12:
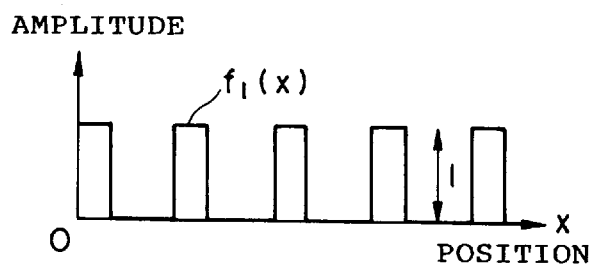
Figure 13:
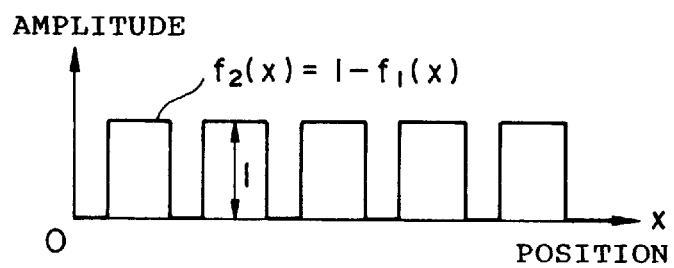

FIG. 10 shows an intensity distribution of light waves when the mask is illuminated from the pattern side. The light intensity is 30% of the intensity of the incident light only at portions where the circuit pattern is present. This results from an example of the circuit pattern composed of two chromium layers. FIG. 11 shows an intensity distribution of light waves transmitted when illuminating the reticle. Such a light intensity distribution results because the intensity transmittance of a reticle without pattern is 96%. In FIG. 10 and FIG. 11 the ordinate indicates the intensity while the abscissa the position. The light intensity distribution of FIG. 12 is expressed by $|\alpha \cdot f_1(x)|^2$, using the amplitude reflectancee $\alpha$ and a function $f_1(x)$ which becomes 1 at portions with pattern as shown in FIG. 12. The light intensity distribution of FIG. 11 is similarly expressed by $|\beta \cdot f_2(x)|^2$, using the amplitude transmittance $\beta$ and a function $f_2(x)=1-f_1(x)$ as shown in FIG. 13. In FIG. 12 and FIG. 13 the ordinate represents the amplitude while the abscissa the position.

Figure 14:
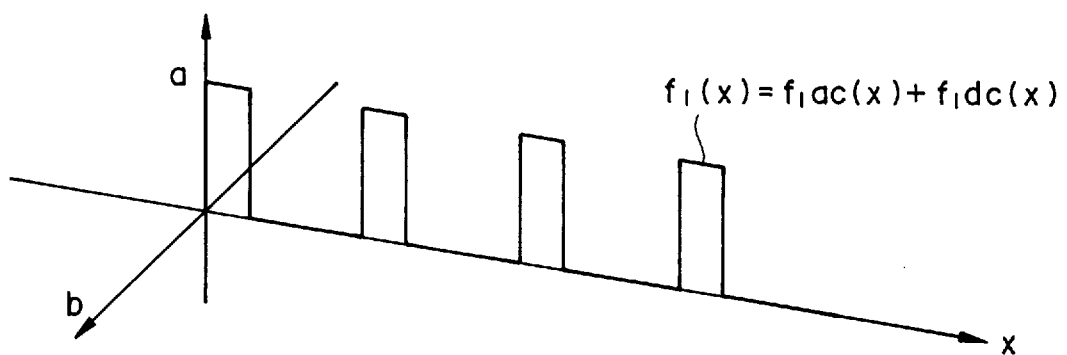
Figure 15:
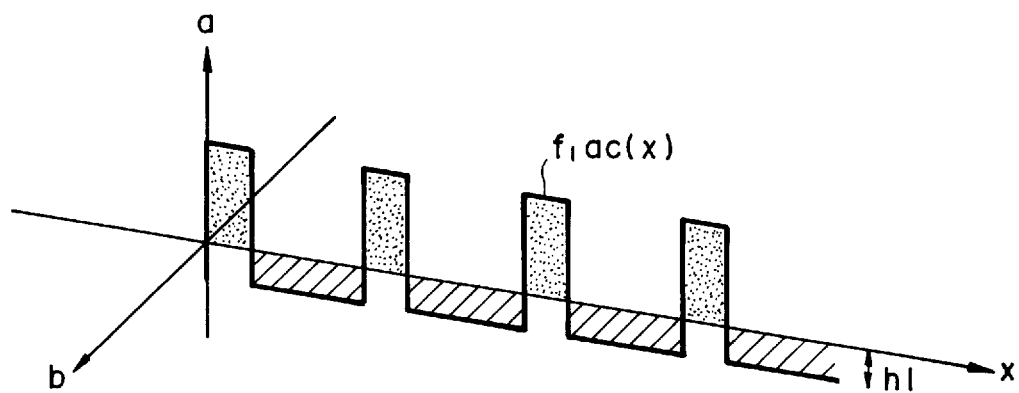
Figure 16:
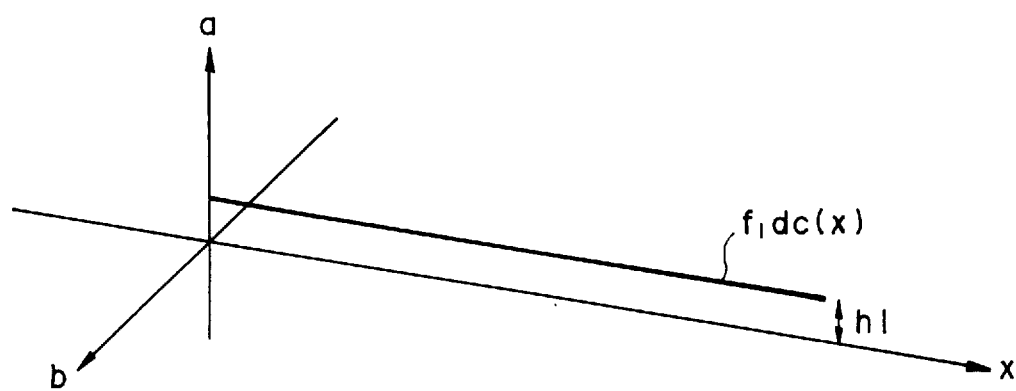

According to vector representation, as shown in FIG. 14, $f_1(x)$ is a sum of ac component $f_1ac(x)$ of $f_1$ shown in FIG. 15 and dc component $f_1dc(x)$ of $f_1(x)$ shown in FIG. 16, where the ac component $f_1ac(x)$ is a function to define two regions with an equal area, a hatched region and a dotted region in the drawing on either side of the x-axis. In this case, $h_1$ is automatically determined.

Figure 17:
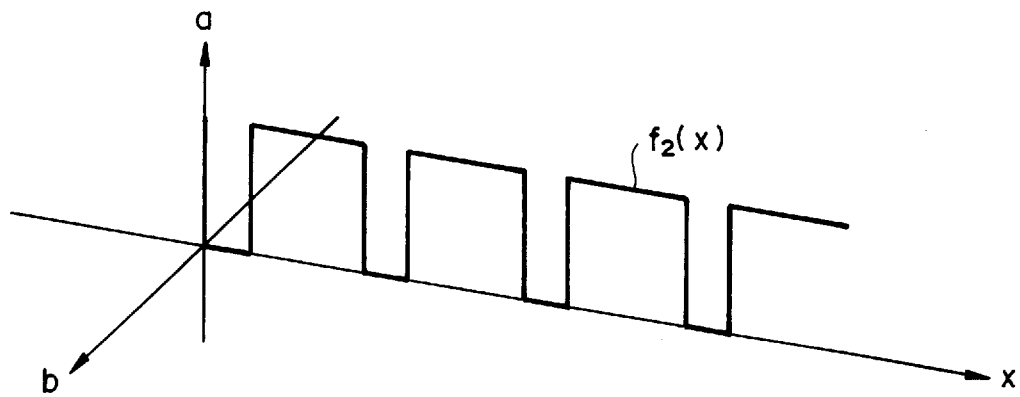
Figure 18:
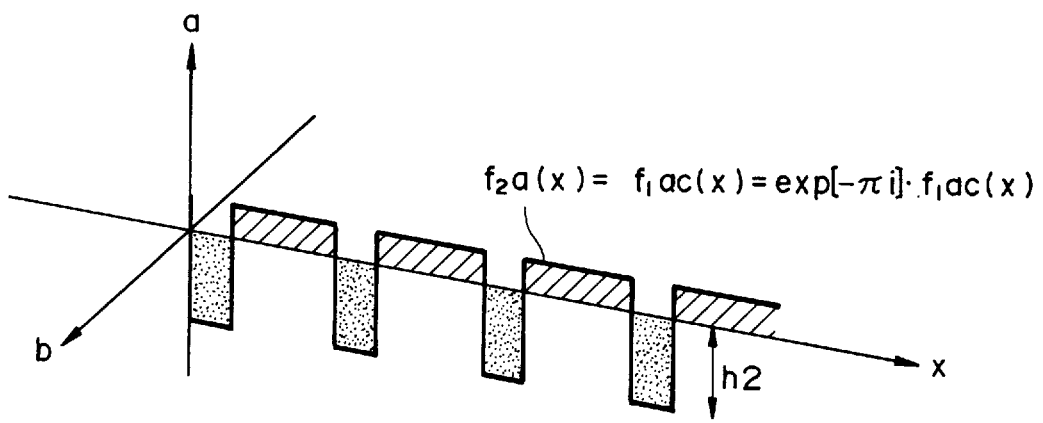
Figure 19:
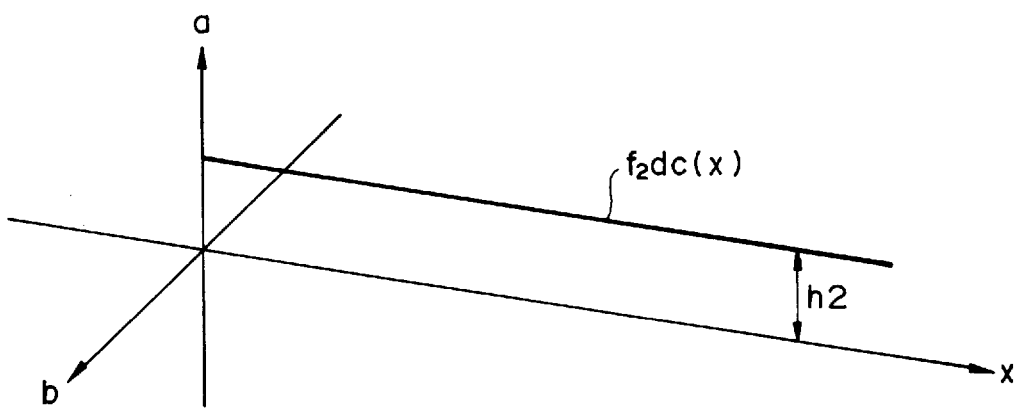

Similarly, according to vector representation of $f_2(x)$, as shown in FIG. 17, $f_2(x)$ is a sum of ac component $f_2ac(x)$ shown in FIG. 18 and dc component $f_2dc(x)$ shown in FIG. 19. The ac component $f_2$ is a function to define two regions with an equal area, which are a hatched region and a dotted region in the drawing on either side of the x-axis. In this case, $h_2$ is automatically determined.

As apparent from FIG. 18, $f_1ac(x)=-f_2ac(x)$. As for the intensities of these, the intensity of the ac component $f_1ac(x)$ is perfectly coincident with the intensity of the ac component $f_2ac(x)$ as follows.

$$|f_1ac(x)|^2=|f_2ac(x)|^2 \qquad (1)$$

As explained, the ac component from the object can be obtained by removing only the zeroth-order diffracted light using the double diffraction optical system and spatial filter, for example as shown in FIG. 9, in the embodiments described above.

Let us consider two image outputs, the transmission image output IDD1 and the reflection image output IDD2, obtained by the optical system of FIG. 9.

Figure 20:
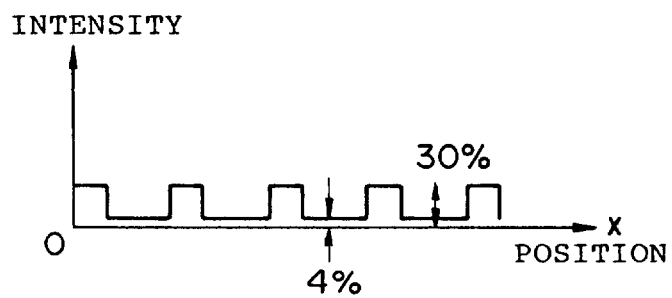

FIG. 20 is a drawing illustrated also taking account of the intensity reflectance 4% of the glass portion of reticle from FIG. 10. The ordinate indicates the intensity while the abscissa the position. The cases showing such a distribution of two intensities (a distribution of intensities of the reflectance 30% and reflectance 4%) include the intensity reflectance distribution of a halftone reticle and the intensity transmittance distribution by transmitted light.

Figure 21:
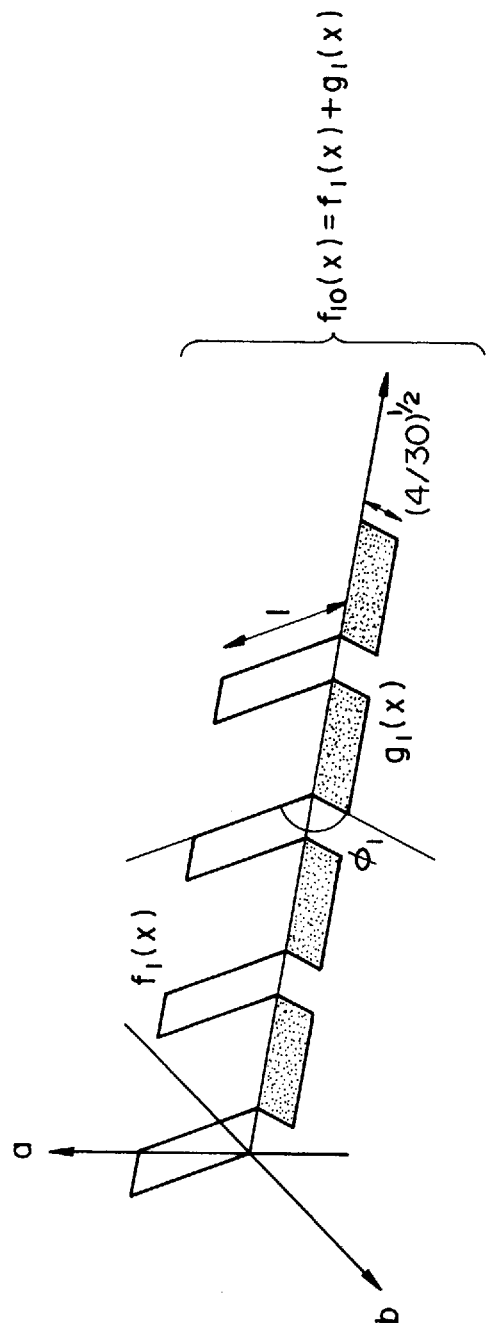

FIG. 21 shows a vector representation with functions $f_1(x)$ and $g_1(x)$ proportional to the amplitude, for an object having the distribution of two intensities as shown in FIG. 20. Here, the function $f_1(x)$ has the intensity 1 at portions having pattern and the function $g_1(x)$ has the intensity of $(4\%/30\%)^{1/2}$ at glass portions. There is a phase difference $\Phi_1$ between the function $f_1(x)$ and the function $g_1(x)$.

A composite function $f_{10}(x)$ of these two functions is given by next Eq. (2).

$$f_{10}(x)=f_1(x)+g_1(x) \qquad (2)$$

Figure 22:
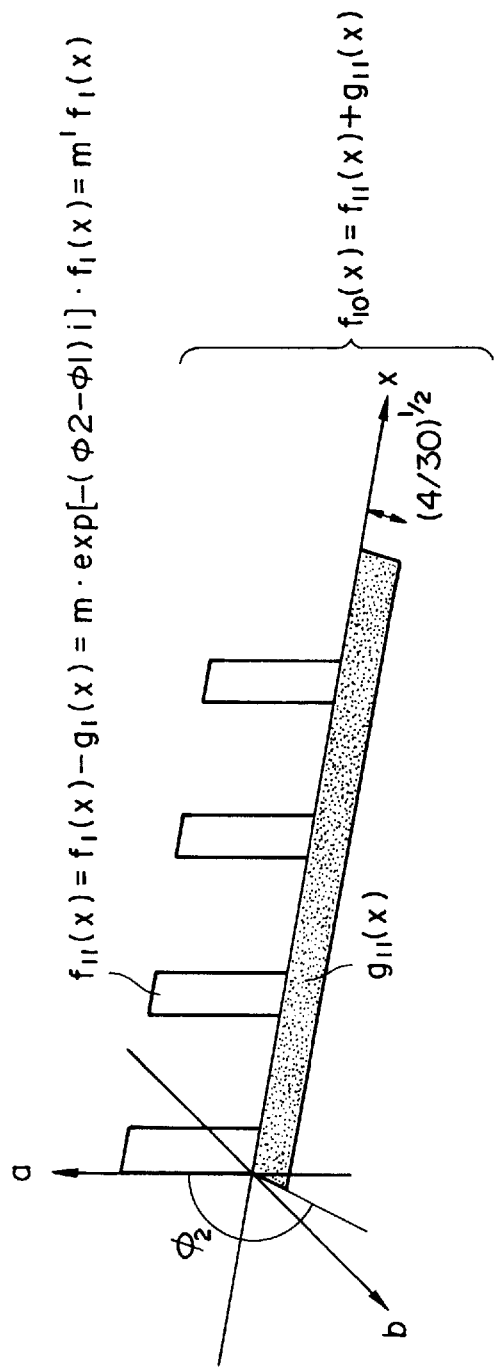

FIG. 22 shows a rewritten form of $f_{10}(x)$, which has the relation of next Eq. (3).

$$\begin{aligned} f_{10}(x) &= f_1(x)+g_1(x) \\ &= f_{11}(x)+g_{11}(x) \\ &= m' \cdot f_1(x)+g_{11}(x) \end{aligned} \qquad (3)$$

From Eq. (3), coefficient m' is a constant independent of the position x, and $f_{10}(x)$ is a sum of $f_1(x)$ multiplied by the coefficient, and the dc component $g_{11}(x)$.

Figure 23:
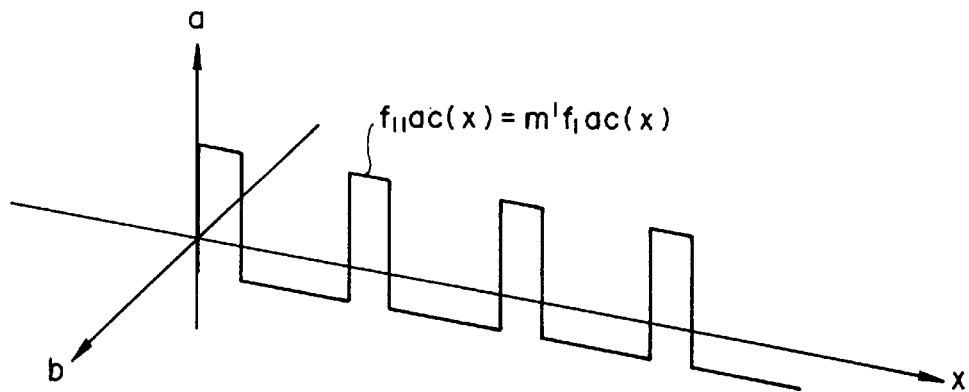

The ac component $f_{11}ac(x)$ of $f_{11}(x)$ is different only in the gain from $f_1(x)$, as shown in FIG. 23, and is coincident with the ac component $f_{10}ac(x)$ of $f_{10}(x)$.

Figure 24:
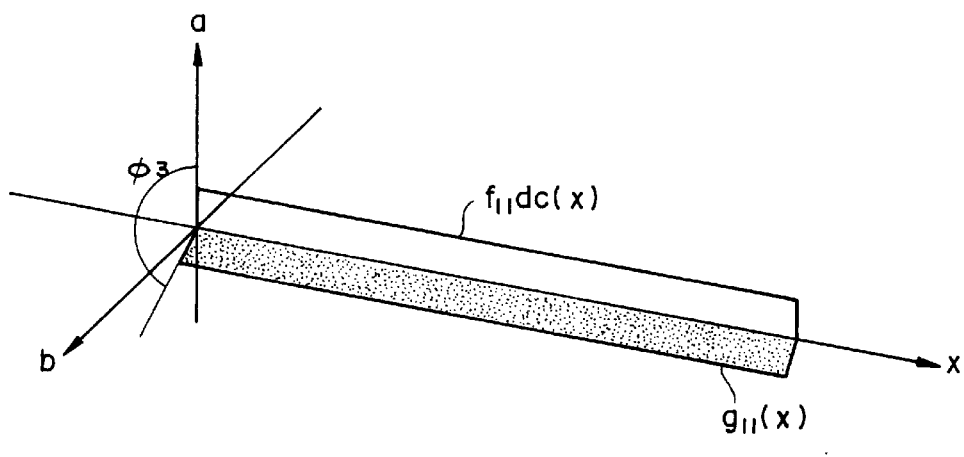
Figure 25:
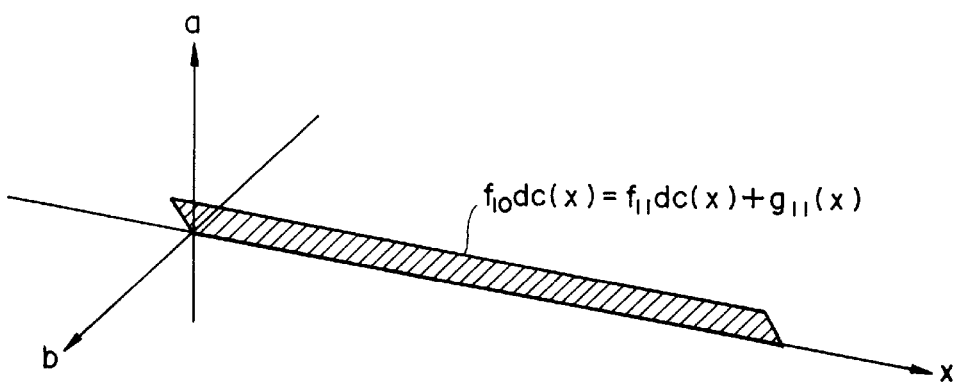

The dc component $f_{10}dc(x)$ of $f_{10}(x)$ is a composite function of two dc components $f_{11}dc(x)$, $g_{11}(x)$ having a phase difference $\Phi_3$, as shown in FIG. 24. The dc component $f_{10}dc(x)$ is shown in FIG. 25. Accordingly, a function with two intensity values or two amplitude values can also be dealt with in the same manner as $f_1(x)$ is as to its ac component.

Figure 26A:
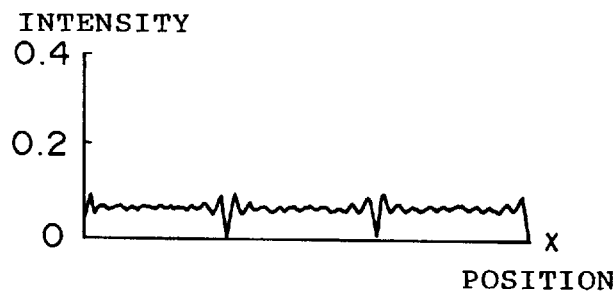
Figure 26B:
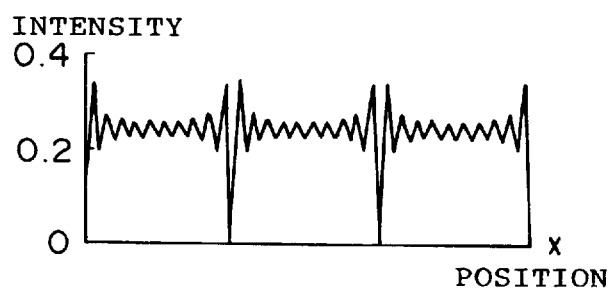

According to the present invention, for example as shown in FIG. 9 in the aforementioned embodiments, the two double diffraction gratings for transmission and for reflection are arranged above and below the reticle and the filters for removing the zeroth-order diffracted light are on the respective Fourier transform planes thereof. Images of the dc component of the transmitted light and the dc component of the reflected light appear on the two image sensors ID1, ID2. These images are so-called dark field images or Schlieren images. Let us consider a case where the circuit pattern is Cr pattern. When the circuit pattern is one-dimensional repetitive patterns of line portions 5 μm and space portions 5 μm and the incident light is of coherent illumination (NA of objective=1) of 488 nm, the signal IDD2 corresponding to the reflection image is as shown in FIG. 26A while the signal IDD1 corresponding to the transmission image is as shown in FIG. 26B. These images are those corresponding to $[\alpha \cdot f_{10}ac(x)]^2, [\beta \cdot f_2ac(x)]^2$, and they appear modified because they are formed from sinusoidal waves of spatial frequencies (0-1/488 Cycles/μm) with finite, depending on limitation of NA of objective and wavelength. Since this example is of the one-dimensional case of calculation, these images are obtained as follows with NA of objective and wavelength λ where * represents convolution.

$$\{\alpha \cdot f_{10}ac(x)*v(x)\}^2 \qquad (4)$$

$$\{\beta \cdot f_1ac(x)*v(x)\}^2 \qquad (5)$$

$$v(x)=\frac{2NA}{\lambda} \cdot \frac{\sin(2\pi NAx/\lambda)}{(2\pi NAx/\lambda)} \qquad (6)$$

Figure 26C:
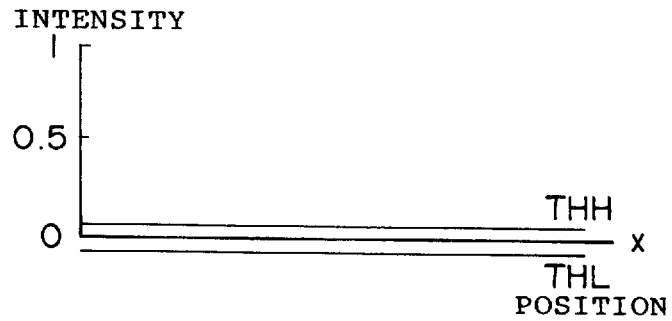

In the two-dimensional case, v(x) is different from Eq. (5), but modulation on the reflection image and the transmission image is the same at any event. Since $f_{10}ac(x)=m' \cdot f_1(x)$, a difference image between the two images, letting $k(\alpha \cdot m')^2=L\beta^2$, becomes perfectly zero as shown in FIG. 26C. In FIG. 26A, FIG. 26B, and FIG. 26C the ordinate represents the intensity while the abscissa the position. For simplicity of description, reflection of glass is not taken into consideration in the embodiments described above under the condition of $f_{10}ac(x)=f_1(x)$.

Figure 27A:
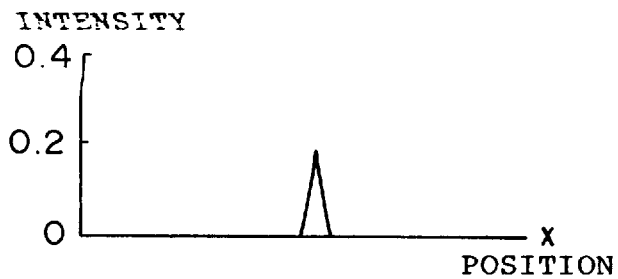
Figure 27B:
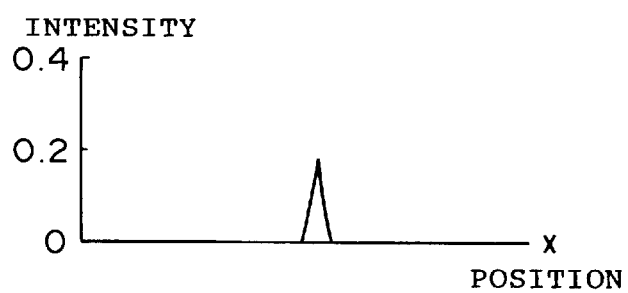
Figure 27C:
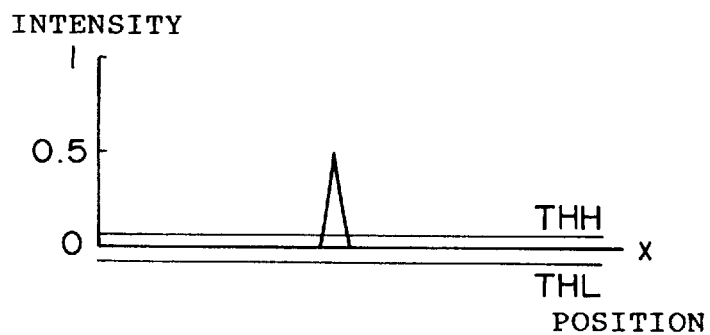

FIG. 27A shows a reflection image of a stain which has the intensity reflectance 20% and the intensity transmittance 80% and the size of 0.6 μm, FIG. 27B a transmission image thereof, and FIG. 27C a difference image obtained by multiplying them by k, l and taking a difference between them. The intensity distributions of the object are of a sharp shape because of the convolution in the point spread function by amplitude in Eq. (5). FIG. 27A and FIG. 27B show the exactly same images. This is because conservation energy holds as intensity transmittance+intensity reflectance=100% when the object (stain) is a dielectric, unlike a metal such as chromium. In the case of chromium, intensity transmittance+intensity reflectance≈30% because of absorption. In FIG. 27A, FIG. 27B, and FIG. 27C, the ordinate represents the intensity while the abscissa the position.

Figure 28A:
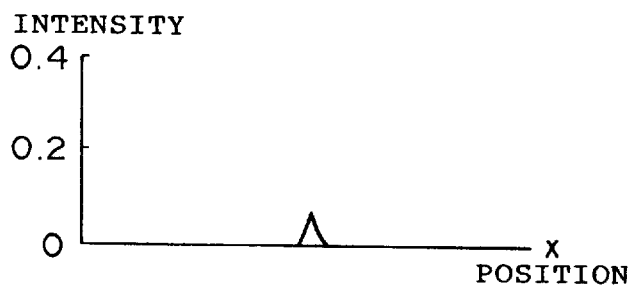
Figure 28B:
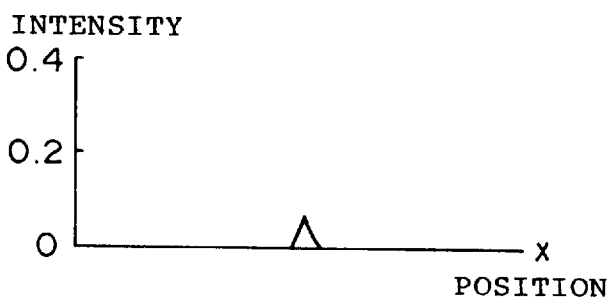
Figure 28C:
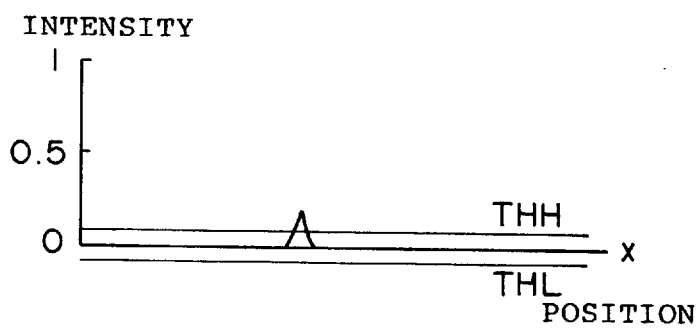

FIGS. 28A, 28B, and 28C show a reflection image and a transmission image in the case of a stain having the size of 0.6 μm, the intensity reflectance of 10%, and the intensity transmittance of 90%. FIG. 28A and FIG. 28B show the reflection image and transmission image, respectively. A difference image after multiplication by k, l as described above is as shown in FIG. 28C. In FIG. 28A, FIG. 28B, and FIG. 28C, the ordinate indicates the intensity while the abscissa the position.

According to the present invention, as explained above, once appropriate gains k, l are determined, the image of circuit pattern can be completely removed out of the difference image between reflection and transmission without being affected by diffraction of lens while leaving only an image of mask defect, and a mask defect can be detected by comparing the image of mask defect with at least one of the threshold value THH and the threshold value THL. In actual detection of mask defect, as shown in FIG. 26C to FIG. 28C, it is possible to set the two window comparators (two threshold values) THH, THL adequately closer to the ground level (zero), thus enabling to detect a finer mask defect.

Even a substance to absorb light, such as a metal, can be fundamentally detected if its intensity ratio of the reflection image and the transmission image is different, even a little, from that of the circuit pattern.

Let us next consider the case where the light receiving surfaces of photoelectric conversion elements are placed on the Fourier transform planes. The Fourier transform is expressed by next Eq. (7).

$$F(2\pi u) = \int_{+\infty}^{-\infty} f(x)e^{-1\times 2xu}dx \quad (7)$$
$$= \text{Fourier transform of } f(x)$$
$$= FT^-\{f(x)\}$$

$$FT^-\{f_1 ac(x)\} = F_1 ac(u) = -F_2 ac(u) \quad (8)$$

$$FT^-\{f_{10} ac(x)\} = F_{10} ac(u) m' F_1 ac(u) \quad (9)$$

$$FT^-\{f_2 ac(x)\} = F_2 ac(u) \quad (10)$$

$$FT[v(x)] = V(u) = \begin{pmatrix} 1 & |u| \geq NA/\lambda \\ 0 & |u| < NA/\lambda \end{pmatrix} \quad (11)$$

From the foregoing, spectra defined as follows are formed on the Fourier transform planes of objective lenses.

$$FT^-\{f_{10} ac(x) * v(x)\} = m' F_1 ac(u) - V(u) \quad (12)$$

$$FT^-\{f_2 ac(x) * v(x)\} = -F_1 ac(u) - V(u) \quad (13)$$

From Eqs. (12) and (13) the same spectra (diffraction images) except for the coefficient m' are observed on the Fourier transform planes of the objective lens receiving the transmitted light and the objective lens receiving the reflected light. Accordingly, photoelectric conversion of the spatial frequency regions (Fourier diffraction images) corresponding to transmission and reflection can also yield a result (effect) equivalent to that when the transmitted light and reflected light is received by the image sensors located on the image planes of the circuit pattern.

The foregoing description explained the so-called coherent illumination, which is illumination of uniform amplitude distribution by plane waves having a sufficiently large illumination area. Next explained is an amplitude distribution of illumination light where the illumination light is incident to the reticle as focused in a beam spot shape having an angular aperture.

Figure 29A:
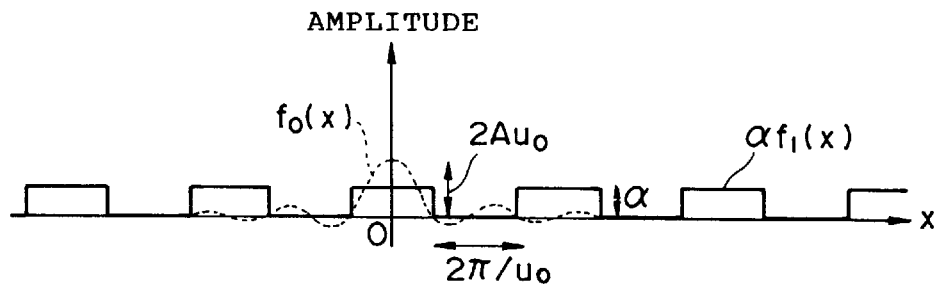
Figure 29B:
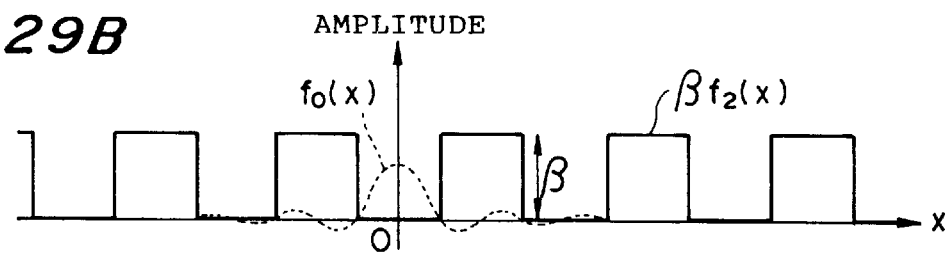
Figure 29C:
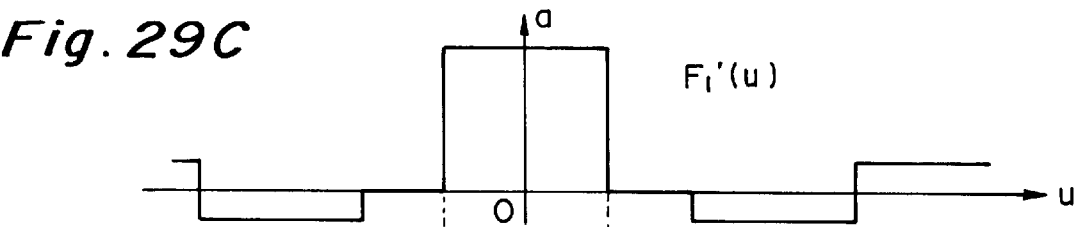
Figure 29D:
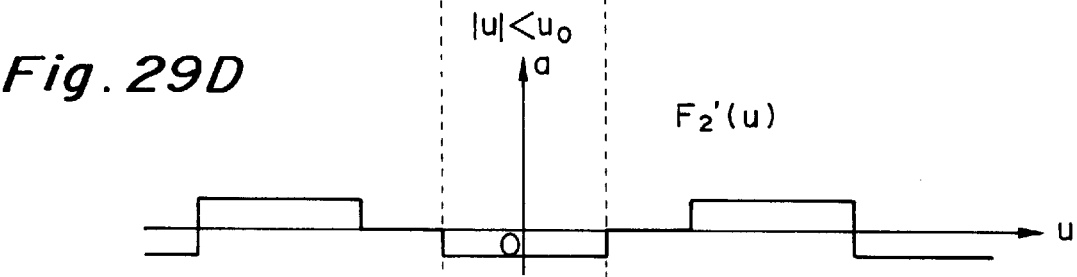
Figure 29E:
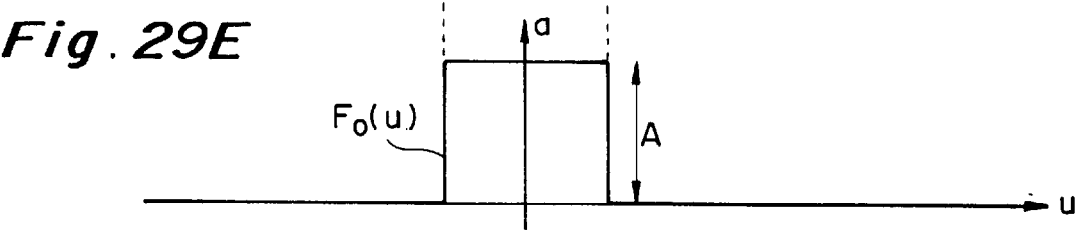

In FIGS. 29A and 29B, FIG. 29A shows an amplitude reflectance distribution $\alpha f_1(x)$ and an amplitude distribution $f_0$ of the illumination light. FIG. 29B shows an amplitude transmittance distribution $\beta f_2(x)$ and an amplitude distribution $f_0(x)$ of the illumination light. The distribution $f_0(x)$ is expressed by Eq. (14), and the following relations hold when the Fourier transform of $f_0(x)$ is $F_0(u)$.

$$f_0(x) = 2Au_0 \frac{\sin 2\pi u_0 x}{2\pi u_0 x} \quad (14)$$

$$FT^-[f_0(X) \times \alpha f_1(x)] = F_0(u) * \alpha F_1(x) = \alpha F'_1(x) \quad (15)$$

$$FT^-[f_0(X) \times \beta f_2(x)] = F_0(u) * \beta F_2(x) = \beta F'_2(x) \quad (16)$$

$$F_0(u) = FT^-[f_0(x)] = \begin{cases} A & |u| \leq u_0 \\ 0 & |u| > u_0 \end{cases} \quad (17)$$

There are the following relations as to the ac components.

$$FT^-[f_0(x) \times \alpha f_1 ac(x)] = F_0(u) * \alpha F_1 ac(u) \quad (18)$$
$$= \alpha F_1 ac(u)$$
$$= \begin{cases} \alpha F(u) & (|u| \leq u_0) \\ 0 & (|u| > u_0) \end{cases}$$

$$FT^-[f_0(x) \times \beta f_2 ac(x)] = -F_0(u) * \beta F_1 ac(u) \quad (19)$$
$$= -\beta F_1 ac(u)$$
$$= \beta F'_2 ac(u)$$

As apparent from Eq. (15), Eq. (16), and FIGS. 29C and 29D, the spectra of the zeroth-order diffracted light are basically the same, though having the width $\pm u_0$, as those in the illumination by plane waves. Namely, the relation of $F'_1 ac(u) = -F'_2 ac(u)$ holds between the two ac components as spatial frequency components (Fourier diffraction image components).

When these two functions $F'_1 ac(u)$ and $-F'_2 ac(u)$ are again subjected to Fourier transformation, same amplitude images are also obtained. These are expressed by Eqs. (20) and (21).

$$FT^-[F'_1 ac(u)] = f'_1 ac(x) = f_0(x) \times f_1 ac(x) \quad (20)$$

$$FT^-[F'_2 ac(u)] = f'_2 ac(x) = f_0(x) \times f_2 ac(x) = f_0(x) \times f_1 ac(x) \quad (21)$$

As explained above, in the present invention the spatial frequency region condensed by the light receiving optical system (the angular region of beam that can pass through the Fourier transform plane) was determined so as to extract only the information of rays occurring from a mask defect having random reflectance and transmittance as eliminating only the information of the components of rays due to the circuit pattern having the existing distribution of reflectance and transmittance in the mask from the rays obtained by the reflection illumination method and the transmission illumination method. The present invention employs the dark field method or Schlieren method while the conventional inspection apparatus employed the bright field method. The present invention applies the Babinet's principle and the technique for cutting the zeroth-order light (for example, the spatial filters), so that the intensity ratio of the light waves traveling in the transmission direction and the light waves traveling in the reflection direction is arranged to be constant for any circuit design if it has no mask defect. Thus, the present invention is fundamentally free from occurrence of pseudo defect and can detect a mask defect easily.

Namely, the optical system for receiving the reflected light has the spatial filter for shielding the zeroth-order diffracted light component of the reflected light from the mask having the circuit pattern while the optical system for receiving the transmitted light has a spatial filter for shielding the zeroth-order diffracted light component of the transmitted light.

Because of this, a difference or ratio between the intensity of the reflected light and the intensity of the transmitted light from the mask having the circuit pattern becomes constant, independent of the configuration, the type, and so on of the circuit pattern. Namely, the difference or ratio is constant between the reflected light reflected by the circuit pattern without deposition of mask defect and transmitted by the aforementioned spatial filter and the transmitted light transmitted by the glass portion of the mask without deposition of mask defect and transmitted by the aforementioned spatial filter. In contrast with it, the difference or ratio is not constant between the reflected light from a mask defect and the transmitted light transmitted by the mask defect and the glass portion of the mask.

In actual inspection of mask defect, detectors receive the reflected light and the transmitted light passing through the respective spatial filters, a signal processing system receiving signals from the detectors calculates the difference or ratio between the intensity of the reflected light and the intensity of the transmitted light, and then the signal processing system compares this difference with predetermined threshold values (two window comparator levels) to discriminate the mask defect from the circuit pattern.

Based on the above constitution and principle, a low-level-difference mask defect or a semitransparent mask defect can be detected. Since the apparatus is arranged to electrically or optically adjust the gains of the intensity of the reflected light and the intensity of the transmitted light, it is possible to nearly equalize the intensity of the reflected light to the intensity of the transmitted light entering the detectors, whereby the difference can be made nearly equal to zero between the intensity of the reflected light and the intensity of the transmitted light. This improves the SN ratio (a ratio of the intensity of the scattered light from the mask defect and the intensity of the scattered light from the circuit pattern).

Figure 30:
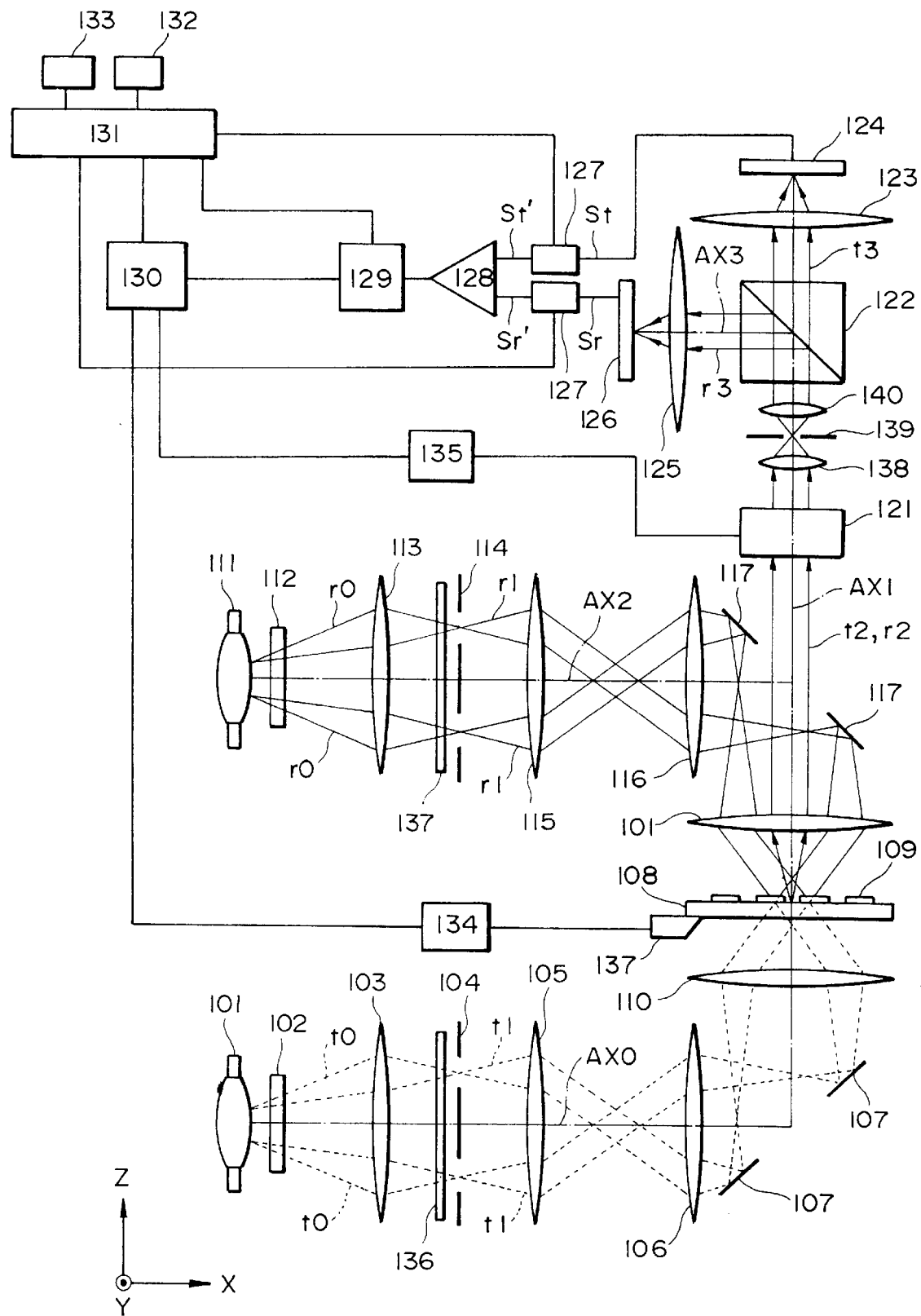
FIG. 30 is a drawing to illustrate the seventh embodiment of the present invention.

The seventh embodiment of the present invention is next explained referring to FIG. 30.

The light source 111 is a mercury lamp and rays emitted therefrom travel through an interference filter 112 to become rays r0. The rays r0 are refracted by a lens 113 to become linearly polarized light r1 with a plane of polarization normal to the plane of the drawing through an analyzer 137, which transmits linearly polarized light with a plane of polarization normal to the plane of the drawing. The rays r1 travel through an annular stop 114 and relay lenses 115, 116 to be reflected toward an objective lens 118 by an annular reflecting mirror 117. The rays r1 are refracted by the objective lens 118 to illuminate a circuit-scribed surface 109 of the reticle 108 in the vertical dark field illumination method.

The light source 101 is a mercury lamp and rays emitted therefrom travel through an interference filter 102 to become rays t0. The rays t0 are refracted by the lens 103 and travel through an analyzer 136, which transmits linearly polarized light with a plane of polarization parallel to the plane of the drawing, to become linearly polarized light t1 with a plane of polarization normal to the plane of the drawing. The rays t1 travel through an annular stop 104 and then through rely lenses 105, 106 to be reflected toward an objective lens 110 by an annular reflecting mirror 107. The rays t1 are refracted by the objective lens 110 to illuminate the circuit-scribed surface 109 of the reticle 108 in the transmission dark field illumination method.

A pinhole 139 provided on the optical axis AX1 of the objective lens 118 is conjugate with the circuit-scribed surface 109 of reticle 108, so that an image of the pinhole 139 can be projected onto the circuit-scribed surface 109 of reticle 108 by a lens 138, a one-dimensional deflecting means 121, and the objective lens 118. The image of the pinhole 139 thus projected can be located at any point on a straight line parallel to the X-direction in the field of the objective lens 118 by the one-dimensional deflecting means 121. Namely, the image of pinhole 139 may be regarded as a point field, and this optical system permits one-dimensional field scanning with the point field.

The one-dimensional scanning means 121 deflects scattered light r2, t2 occurring from an object point in the circuit-scribed surface 109 and in the field of the objective lens 118 illuminated by the rays r1 and rays t1, so that the scattered light r2, t2 travels through the lens 138, pinhole 139, and lens 140 to reach a polarizing beam splitter 122. The one-dimensional scanning means 121 selects a position of a specific object point out of a plurality of object points in the field of the objective lens 118 and deflects the scattered light r2, t2 occurring from this object point to guide it to the polarizing beam splitter 122.

The linearly polarized light r2 with the plane of polarization normal to the plane of the drawing, which is the scattered light occurring from the point field conjugate with the pinhole 139, is reflected by the polarizing beam splitter 122 and is refracted by a lens 125 to enter a photoelectric conversion element 126 to be photoelectrically converted there.

The linearly polarized light t2 with the plane of polarization parallel to the plane of the drawing, which is the scattered light occurring from the point field conjugate with the pinhole 139, is transmitted by the polarizing beam splitter 122 and is refracted by a lens 123 to enter a photoelectric conversion element 124 to be photoelectrically converted there.

An attenuator 127 adjusts a signal intensity ratio of two video signals to be input to a differential amplifier 128 in accordance with a command from a computer 131. The attenuator 127 sets the video signal Sr and the video signal St output from the photoelectric conversion element 126 and the photoelectric conversion element 124 to two signals (Sr', St') having such a signal intensity ratio that an output from the differential amplifier 128 becomes zero with no defect in the circuit-scribed surface 109 of reticle 108, and then supplies them to the differential amplifier 128.

The differential amplifier 128 outputs an error signal proportional to a difference between the input signal Sr' and the input signal St'.

The error signal being the output from the differential amplifier 128 is input into the signal processing circuit 129. The signal processing circuit 129 has a window comparator circuit, which is a binarizing circuit having two slice levels on the plus side and on the minus side. The signal processing circuit 129 outputs a strength value of the error signal, an output from the binarizing circuit indicating presence or absence of a defect, and so on to a synchronizer 130.

The two plus and minus slice levels of the window comparator circuit in the signal processing circuit 129 are set at levels not causing a pseudo defect by optical noise or electrical noise. These slice levels can be set from the outside through an interface 132 and the computer 131.

The synchronizer 130 performs synchronizing control of the one-dimensional scanning means 121 and an X-Y stage 137 during execution of inspection. The one-dimensional scanning means 121 is driven through an actuator 135. The X-Y stage 137 is driven through an actuator 134.

One X-directional field scanning by the one-dimensional scanning means 121 can inspect a linear region or a region on a scanning line having the longitudinal direction along the X-direction, the length of which is limited by the size of the field of the objective lens 118. If the reticle 108 is moved at appropriate constant speed in the Y-direction by the X-Y stage 137 as repeating the X-directional field scanning by the one-dimensional scanning means 121, a rectangular region in the size determined by the length of X-directional scanning lines and the moving distance of the reticle in the Y-direction is covered by a plurality of linear regions (scanning lines) scattered at constant intervals as maintaining suitable overlap on the circuit-scribed surface, thereby enabling to inspect the entire surface in this rectangular region.

The synchronizer 130 adds information indicating an existing position of a defect (XY coordinates) to the information including the intensity value of the error signal, the output from the binarizing circuit indicating presence or absence of a defect, and so on sent from the signal processing circuit 129, and then sends it to the computer 131.

The computer 131 makes a map indicating the position of defect in the reticle and the intensity of the error signal at the defect position and displays it on a display unit 133.

The computer 131 can automatically set up the gains of the attenuators 127. For this setup, a defectless reticle or a defectless portion of a reticle having a defect is used. Optimum values of the gains of the attenuator differ depending upon the type of reticle, for example, depending upon whether a reticle of chromium pattern, a reticle of halftone pattern, or the like. Once the optimum gain values are measured for every type of reticle and are stored in a memory in the computer 131, they can be readily set up in subsequent inspection using the data in the memory.

From the outside the operator inputs through the interface 132 to the computer 131 a type of a reticle to be inspected (for example, a reticle of chromium pattern, a reticle of halftone pattern, or the like), an inspection mode, an inspection sensitivity, an inspection area, execution of initial setting of apparatus, execution of inspection, and so on.

In the present embodiment the zeroth-order spectral components of the illumination light (the regularly reflected light and the transmitted light traveling straight) travel in directions different from the direction of the rays t2, r2, which are to be photoelectrically converted, so that they are not photoelectrically converted. It is thus needless to mention that there is no need to set a spatial filter at the position conjugate with the pupil of objective lens.

Figure 31A:
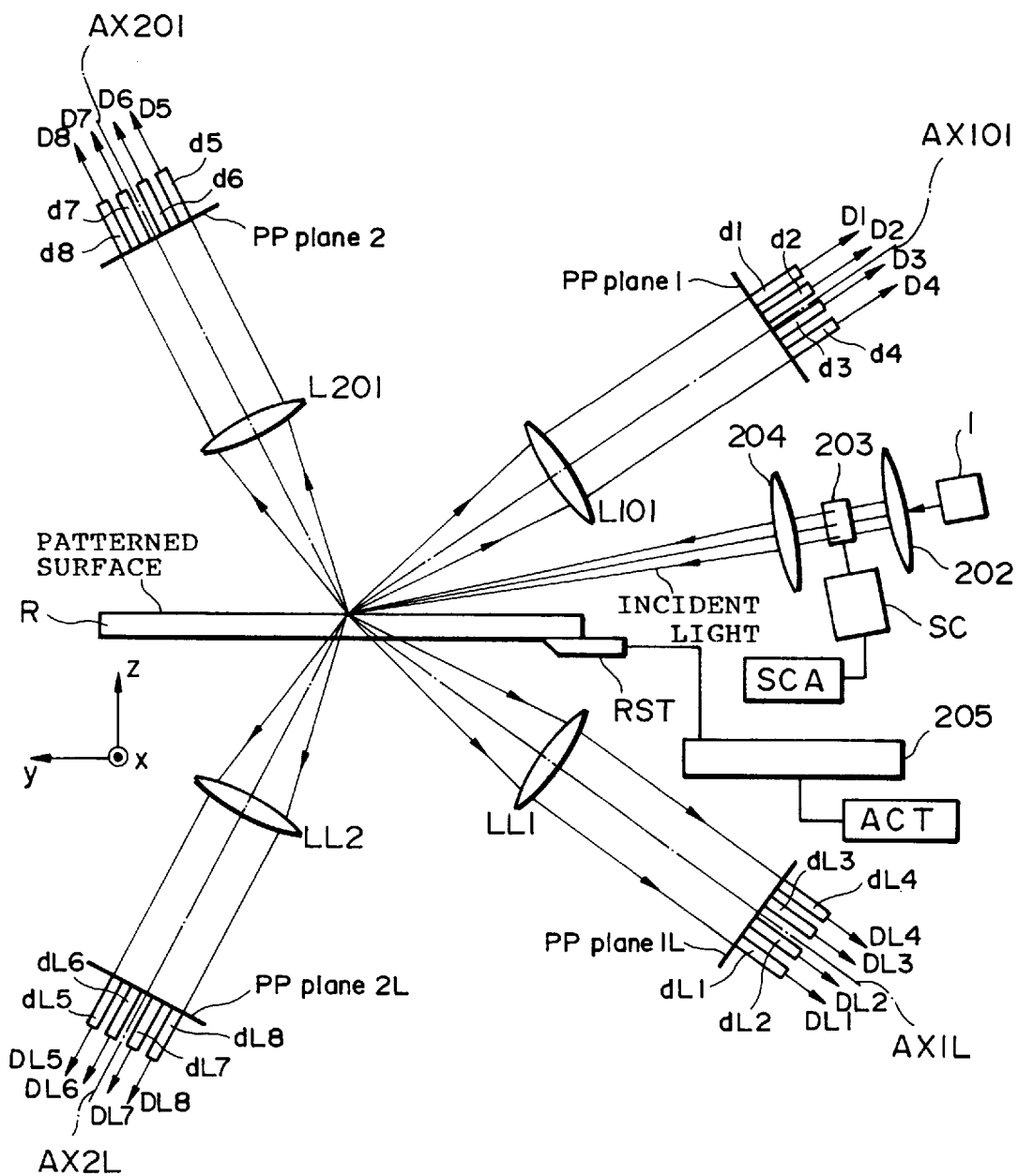
FIG. 31A is a drawing to illustrate the eighth embodiment of the present invention.

FIG. 31A is a drawing to show the inspection apparatus according to the eighth embodiment of the present invention.

The light source 1 is a light source for emitting laser, and rays emitted from the light source 1 are expanded by a beam expander 202 to become parallel rays expanded. The parallel rays are reflected by the oscillating mirror 203 and then are condensed by a scanning lens 204 to illuminate the reticle R in an obliquely incident manner. The oscillating mirror 203 is driven by one-dimensional scanning means SC and driver SCA to deflect the rays, thereby enabling optical scanning on a scanning line LCR parallel to the X-direction on the reticle. Scattered light occurring from each point on the scanning line LCR is condensed by four objective lenses L101, L201, LL1, LL2 to be photoelectrically converted by sixteen photoelectric conversion elements d1, d2, d3, d4, d5, d6, d7, d8, dL1, dL2, dL3, dL4, dL5, dL6, dL7, dL8, light detecting surfaces of which are positioned on pupil-conjugate planes of the objectives (PP plane 1, PP plane 2, PP plane 1L, PP plane 2L). Then sixteen output signals D1, D2, D3, D4, D5, D6, D7, D8, DL1, DL2, DL3, DL4, DL5, DL6, DL7, DL8 are input into the signal processing circuit (see FIG. 32).

The optical axes AX101, AX201, AX1L, AX2L of the four objective lenses L101, L201, LL1, LL2 are so set that regularly reflected rays occurring when the illumination rays are reflected by the reticle R and the transmitted light traveling straight as transmitted without being diffracted or scattered by the reticle R cannot enter either of the four objective lenses.

The reticle R is mounted on the reticle stage RST, and the reticle stage RST is arranged as movable in the Y-direction by a reticle slider 205. The synchronizer TIM (see FIG. 35) performs synchronizing control of the one-dimensional scanning means SC and the Y-stage reticle slider during execution of inspection. The one-dimensional scanning means SC is driven through an actuator SCA. The reticle stage RST is driven through an actuator ACT.

One X-directional field scanning by the one-dimensional scanning means SC can illuminate a linear region or scanning line LCR having the longitudinal direction along the X-direction, the length of which is limited by the magnitude of the field angle of the scanning lens 204, thereby enabling inspection of this region. If the reticle R is moved at appropriate constant speed in the Y-direction by the reticle slider 205 as repeating the X-directional optical scanning by the one-dimensional scanning means SC, a rectangular region in the size determined by the length of the X-directional scanning line LCR and the moving distance of the reticle in the Y-direction can be covered with a plurality of linear regions (scanning lines LCR) scattered at constant intervals as properly overlapping on the circuit-scribed surface or patterned surface, thereby enabling inspection of the entire surface in this rectangular region.

FIG. 32 is a structural drawing of the control system in the present embodiment. The sixteen output signals D1, D2, D3, D4, D5, D6, D7, D8, DL1, DL2, DL3, DL4, DL5, DL6, DL7, DL8 are input into the signal processing circuit SP. The signal processing circuit SP performs a predetermined arithmetic with the input signals and outputs a signal det indicating whether presence of defect is true or false and a defect signal intensity ss out indicating a signal intensity at a defect portion as a result of the arithmetic. These are input into the synchronous circuit TIM.

The synchronous circuit TIM communicates with the actuator SCA of the one-dimensional scanning means and the actuator ACT of the reticle slider 205 to control the operations thereof. Namely, the synchronous circuit TIM performs optical scanning in a predetermined region, based on a command from the computer COM, to inspect a defect in this region.

Based on the signal det indicating whether presence of defect is true or false, sent from the signal processing circuit SP, the synchronous circuit TIM adds the information indicating an existing position of defect (XY coordinates) to the information of the defect signal intensity ss out indicating the signal intensity at the defect portion and sends it to the computer COM.

The computer COM makes a map indicating the position of defect in the reticle and the defect signal intensity ss out at the defect position and displays it on the display unit DIS.

Communicating with the signal processing circuit SP, the computer COM can automatically set up the gains in the signal processing circuit SP. For this setup a defectless reticle or a defectless portion of a reticle having a defect is used. Optimum values of the gains in the signal processing circuit SP differ depending upon the type of reticle, for example, depending upon the reticle of chromium pattern, the reticle of halftone pattern, or the like. Once optimum gain values for every type of reticle are measured and stored in a memory in the computer COM, the setup can be readily performed in subsequent inspection using the data in the memory. From the outside the operator inputs through the interface IF to the computer COM the type of inspected reticle (the reticle of chromium pattern, the reticle of halftone pattern, or the like), the inspection sensitivity, the inspection area, execution of initial setting of apparatus, execution of inspection, and so on.

Figure 33:
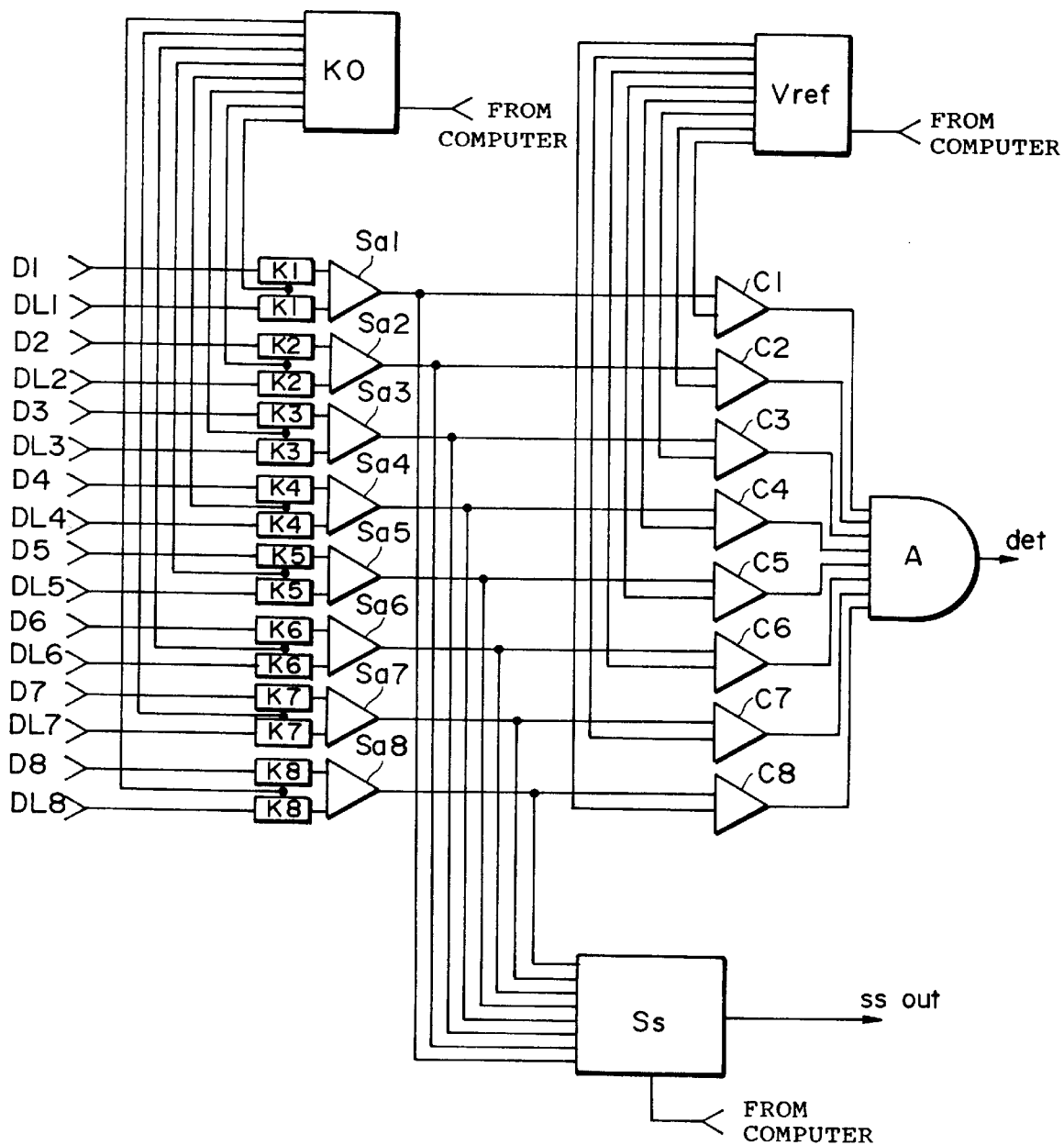
FIG. 33, FIG. 34, FIG. 35, and FIG. 36 are drawings to illustrate embodiments of the signal processing circuit SP of FIG. 31A.

FIG. 33 shows a first example of the signal processing circuit SP in the present embodiment. Eight pairs of photoelectric conversion signals (D1, DL1), (D2, DL2), (D3, DL3), (D4, DL4), (D5, DL5), (D6, DL6), (D7, DL7), (D8, DL8) are input into attenuators K1, K2, K3, K4, K5, K6, K7, K8 and they are adjusted at a predetermined signal intensity ratio in accordance with a command from the computer COM. Attenuation rates of the attenuators K1, K2, K3, K4, K5, K6, K7, K8 can be arbitrarily set by the computer COM through an attenuation rate setter K0. Outputs from the attenuators K1, K2, K3, K4, K5, K6, K7, K8 are input into differential amplifiers Sa1, Sa2, Sa3, Sa4, Sa5, Sa6, Sa7, Sa8 and these differential amplifiers output differential outputs, each being a signal proportional to a difference between input signals.

These differential outputs each are compared with a reference level from a reference level generator Vref in comparators C1, C2, C3, C4, C5, C6, C7, C8, which supply binary signals indicating whether true or false to an AND circuit A.

The eight comparators each output a true value (high level) when a differential output from a differential amplifier exceeds the reference level from the reference level generator Vref or output a false value (low level) otherwise. The AND circuit A outputs a true value only when the all eight inputs are true or outputs a false value otherwise.

The reference level of the reference level generator Vref can be set at an arbitrary level in accordance with a command from the computer COM, and a change of this level can change the detection sensitivity of defect.

On the other hand, the eight differential outputs are also input into a signal selector Ss. The signal selector Ss outputs, as an output signal ss out, a value preliminarily selected through the computer COM by the operator out of the minimum, the maximum, and the average of the signals input thereto. Normally, the output of the minimum is sufficient. This is because the minimum includes the lowest background noise and loyally reflects the intensity of the scattered light from a defect. The signal is updated at a rate sufficient for intensity changes of input signals to output real-time values.

Figure 34:
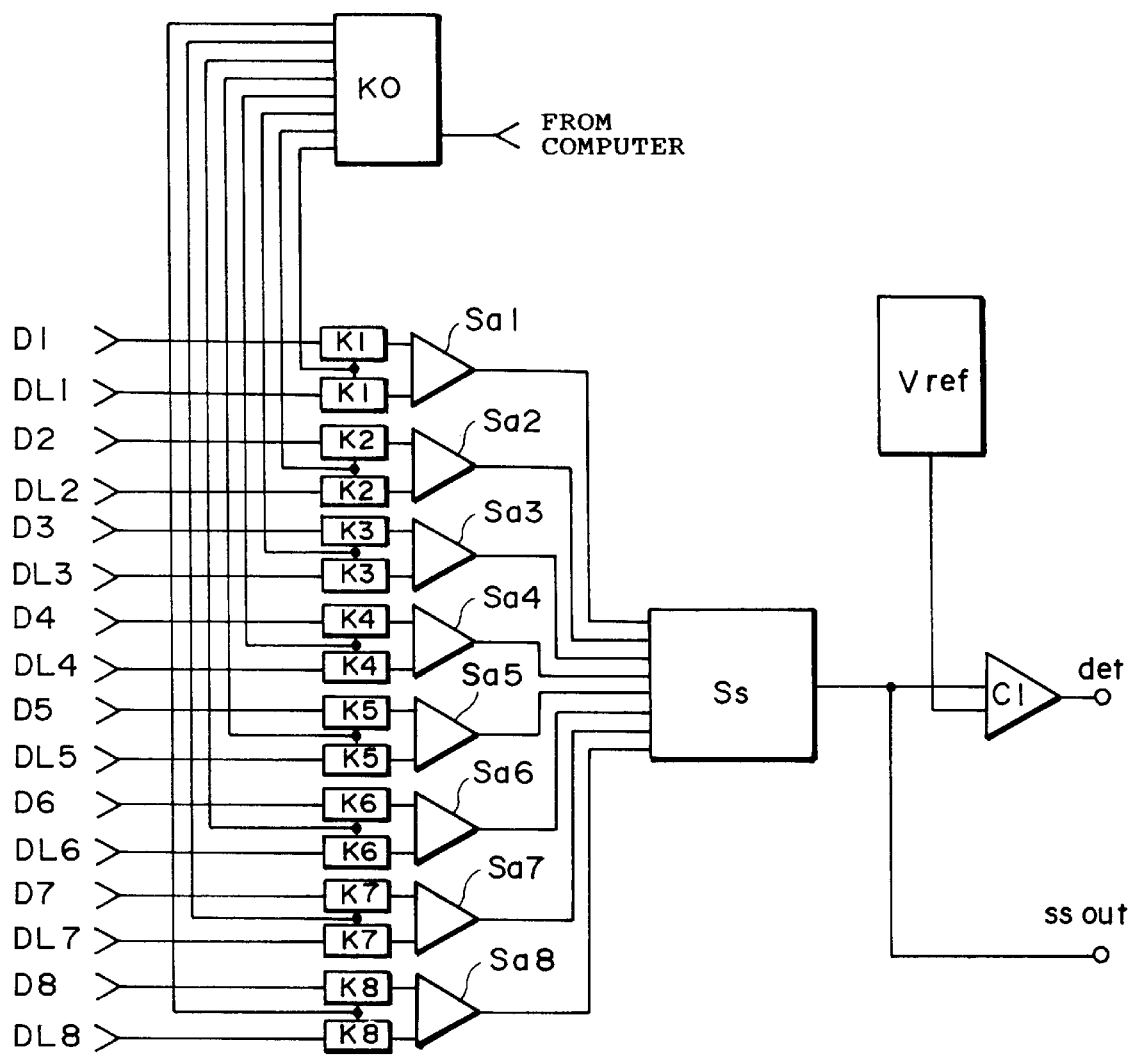

FIG. 34 shows a second example of the signal processing circuit SP in the present embodiment. Eight pairs of photoelectric conversion signals (D1, DL1), (D2, DL2), (D3, DL3), (D4, DL4), (D5, DL5), (D6, DL6), (D7, DL7), (D8, DL8) are input into the attenuators K1, K2, K3, K4, K5, K6, K7, K8 to be adjusted at a predetermined signal intensity ratio in accordance with a command from the computer COM and then to be input into the differential amplifiers.

Outputs from the attenuators K1, K2, K3, K4, K5, K6, K7, K8 are input into the differential amplifiers Sa1, Sa2, Sa3, Sa4, Sa5, Sa6, Sa7, Sa8 and these differential amplifiers output differential outputs, each being a signal proportional to a difference between input signals. The differential outputs are input into the signal selector Ss and the signal selector Ss outputs the minimum as an output signal ss out, out of the input signals. The output signal ss out is updated at a rate sufficient for intensity changes of the input signals to output real-time values.

The output signal ss out is compared with the reference level from the reference level generator Vref in a comparator C1, which outputs a binary signal indicating whether true or false, as a true or false signal det.

The comparator C1 outputs a true value (high level) when the output signal ss out exceeds the reference level of the reference level generator Vref or outputs a false value (low level) otherwise.

The reference level of the reference level generator Vref can be set at an arbitrary level in accordance with a command from the computer COM, and the detection sensitivity of defect can be changed by changing this level.

On the other hand, the output signal ss out is also output to the synchronous circuit TIM.

Figure 35:
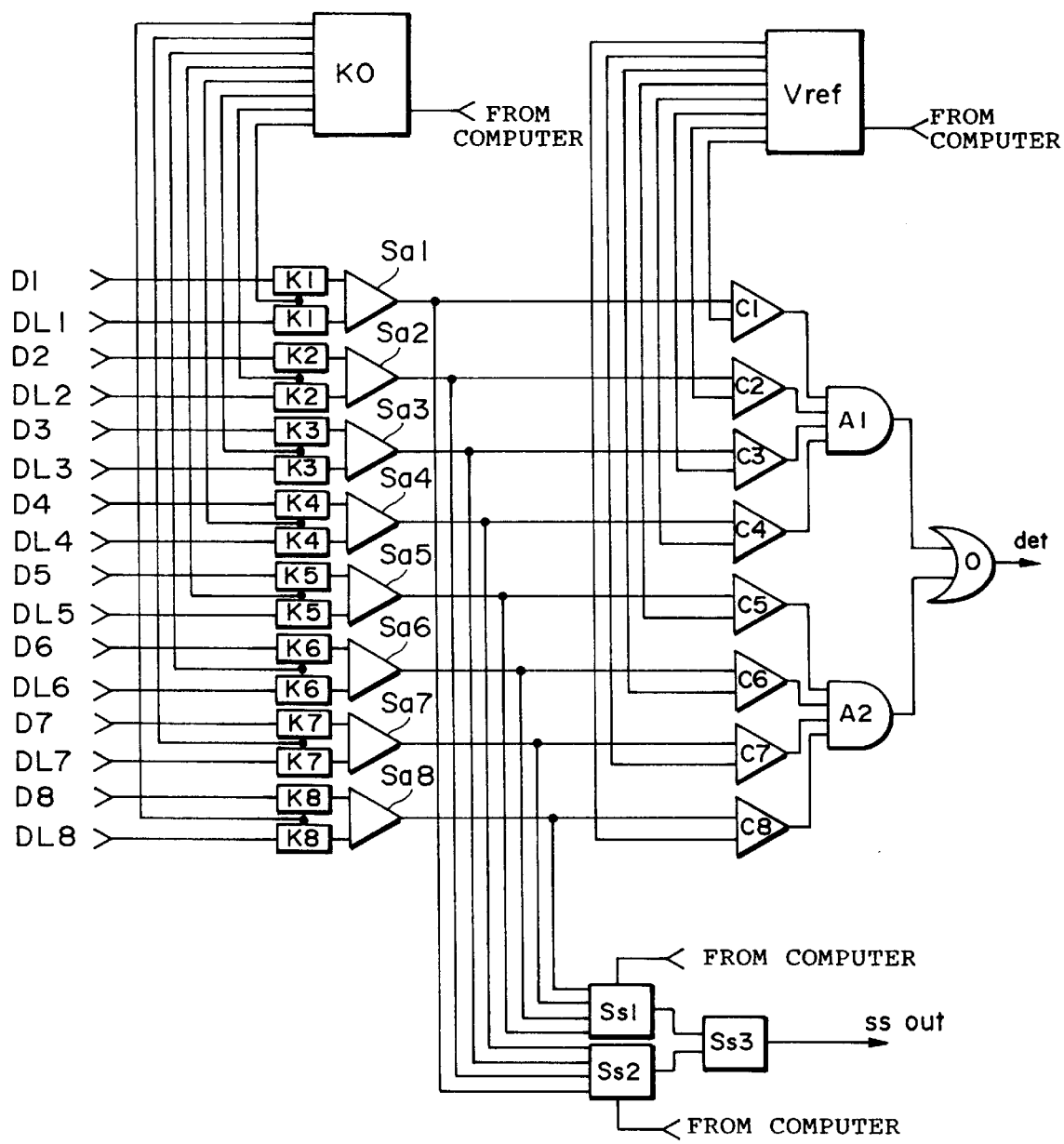

FIG. 35 shows a third example of the signal processing circuit SP in the present embodiment. Eight pairs of photoelectric conversion signals (D1, DL1), (D2, DL2), (D3, DL3), (D4, DL4), (D5, DL5), (D6, DL6), (D7, DL7), (D8, DL8) are input into the attenuators K1, K2, K3, K4, K5, K6, K7, K8 to be adjusted at a predetermined signal intensity ratio in accordance with a command from the computer COM.

Outputs from the attenuators K1, K2, K3, K4, K5, K6, K7, K8 are input into the differential amplifiers Sa1, Sa2, Sa3, Sa4, Sa5, Sa6, Sa7, Sa8, and these differential amplifiers output differential outputs, each being a signal proportional to a difference between input signals.

These differential outputs are compared with the reference level of the reference level generator Vref to generate binary signals indicating whether true or false, and outputs from the comparators C1, C2, C3, C4 are input into an AND circuit A1. Outputs from the comparators C5, C6, C7, C8 are input into an AND circuit A2. Outputs from the AND circuit A1 and AND circuit A2 are input into an OR circuit O. The OR circuit O outputs an output signal det indicating presence or absence of defect.

The eight comparators each output a true value (high level) when a differential output from the differential amplifier exceeds the reference level of the reference level generator Vref or outputs a false value (low level) otherwise.

The AND circuit A1, A2 outputs a true value only when the all four inputs are true or outputs a false value otherwise. The OR circuit O outputs a true value if either one of the two inputs is true. A purpose of this logic is to make it possible to detect a defect of any configuration even in the cases having extreme deviation of scattering directivity depending upon a configuration of a defect by such an arrangement that a defect is presumed to exist even if only one light receiving means has a large receiving light intensity of scattered light out of a plurality of light receiving means including objective lenses disposed in multiple directions.

The reference level of the reference level generator Vref can be set at an arbitrary level in accordance with a command from the computer COM, and the detection sensitivity of defect can be changed by changing this level.

On the other hand, the differential outputs from the four differential amplifiers Sa1, Sa2, Sa3, Sa4 are also input into a signal selector Ss1. The differential outputs from the four differential amplifiers Sa5, Sa6, Sa7, Sa8 are also input into another signal selector Ss2. These signal selectors Ss1, Ss2 output respective values preliminarily selected through the computer COM by the operator out of the values such as the minimum, the maximum, and the average of the input signals.

The signals output from these signal selectors Ss1, Ss2 may be normally outputs of minimum values. This is because the minimum values include the lowest background noise and loyally reflect the intensity of the scattered light from a defect. These signals are updated at a rate sufficient for intensity changes of the input signals to output real-time values.

A signal selector Ss3 outputs, as an output signal ss out, a value preliminarily selected through the computer COM by the operator out of the values such as the minimum, the maximum, and the average of the signals input thereto.

Normally, an output of the maximum is sufficient for the signal output from the signal selector Ss3. This is because extreme deviation of scattering directivity appears depending upon a configuration of a defect detected and the intensity of the scattered light from the defect is faithfully reflected when a light receiving means supplying a signal of greater receiving light intensity of the scattered light is given priority to out of those including the objective lenses located in multiple directions. These signals are updated at a rate sufficient for intensity changes of input signals to output real-time values as the output signal ss out.

Figure 36:
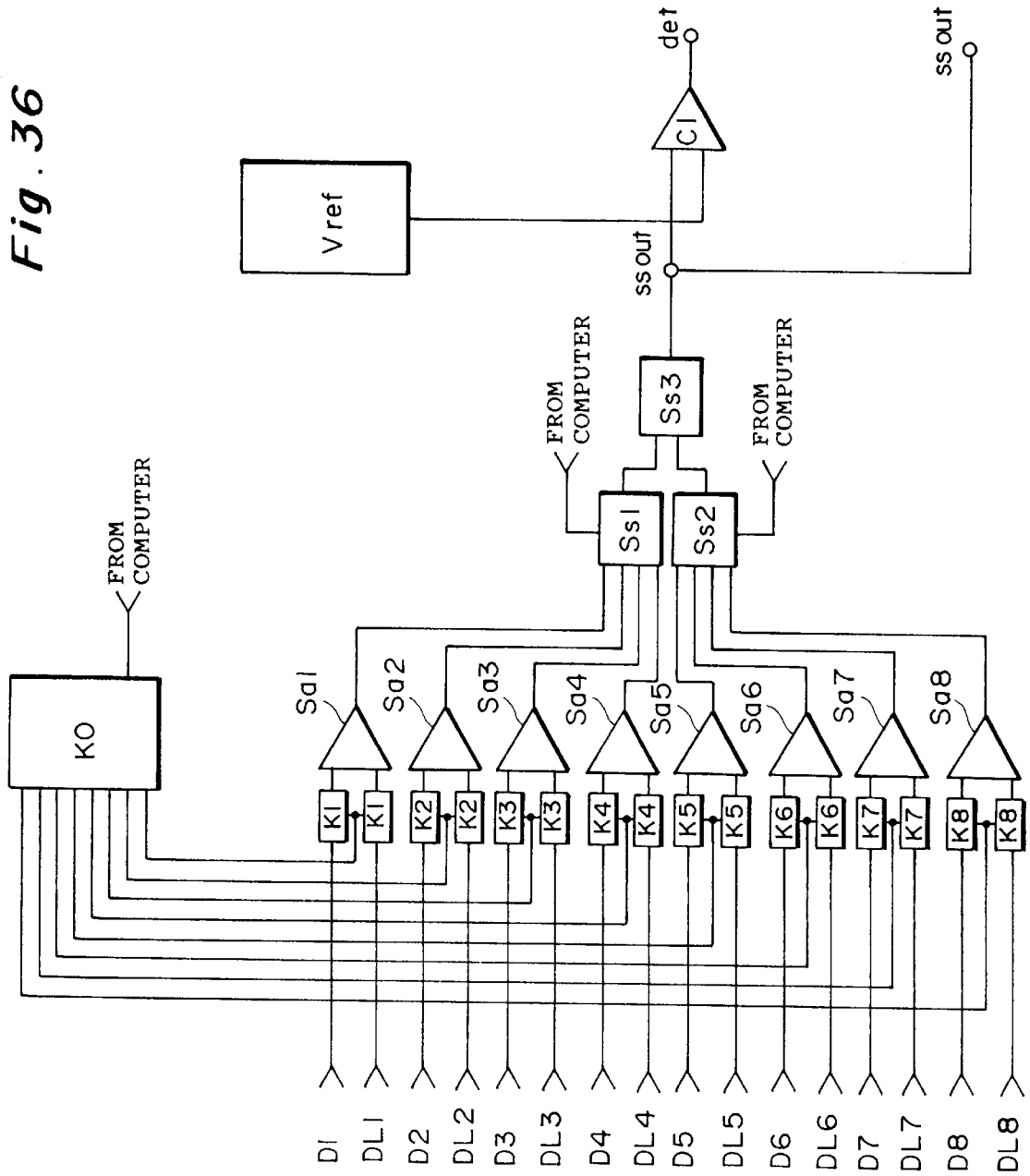

FIG. 36 shows a fourth example of the signal processing circuit SP in the present embodiment. Eight pairs of photoelectric conversion signals (D1, DL1), (D2, DL2), (D3, DL3), (D4, DL4), (D5, DL5), (D6, DL6), (D7, DL7), (D8, DL8) are input into the attenuators K1, K2, K3, K4, K5, K6, K7, K8 to be adjusted at a predetermined signal intensity ratio in accordance with a command from the computer COM.

The outputs from the attenuators K1, K2, K3, K4, K5, K6, K7, K8 are input into the differential amplifiers Sa1, Sa2, Sa3, Sa4, Sa5, Sa6, Sa7, Sa8, and these differential amplifiers output differential outputs, each being a signal proportional to a difference between input signals. The differential outputs from the differential amplifiers Sa1, Sa2, Sa3, Sa4 are input into the signal selector Ss1 while the differential outputs from the differential amplifiers Sa5, Sa6, Sa7, Sa8 are input into the signal selector Ss2. Each of the two signal selectors Ss1, Ss2 outputs a minimum value. This is because the output of minimum value includes the lowest background noise and loyally reflects the intensity of the scattered light from a defect. The two signal selectors Ss1, Ss2 are updated at a rate sufficient for intensity changes of the input signals to output real-time values.

Outputs from the two signal selectors Ss1, Ss2 are input into the signal selector Ss3. An output of the maximum out of the two signals is normally sufficient for a signal output from the signal selector Ss3. This is because extreme deviation of scattering directivity occurs depending upon a configuration of a defect detected and the intensity of the scattered light from the defect is loyally reflected when a light receiving means supplying a signal of greater receiving light intensity of the scattered light is given priority to out of those including the objective lenses disposed in multiple directions. These signals are updated at a rate sufficient for intensity changes of the input signals to output real-time values as the output signal ss out.

The output signal ss out is compared with the reference level of the reference level generator Vref in the comparator C1, which outputs a binary signal indicating whether true or false as a true or false signal det.

The comparator C1 outputs a true value (high level) when the output signal ss out exceeds the reference level of the reference level generator Vref or outputs a false value (low level) otherwise.

The reference level of the reference level generator Vref can be set at an arbitrary level in accordance with a command from the computer COM (not shown), and the detection sensitivity of defect can be changed by changing this level.

On the other hand, the output signal ss out is also output to the synchronous circuit TIM.

In the present embodiment the zeroth-order spectral components of the illumination light (the regularly reflected light and the transmitted light traveling straight) travel in directions different from the direction of the rays t2, r2, which are to be photoelectrically converted, and they are thus not photoelectrically converted. It is thus needless to mention that there is no need to provide a spatial filter at the position conjugate with the pupil of objective lens.

Figure 37:
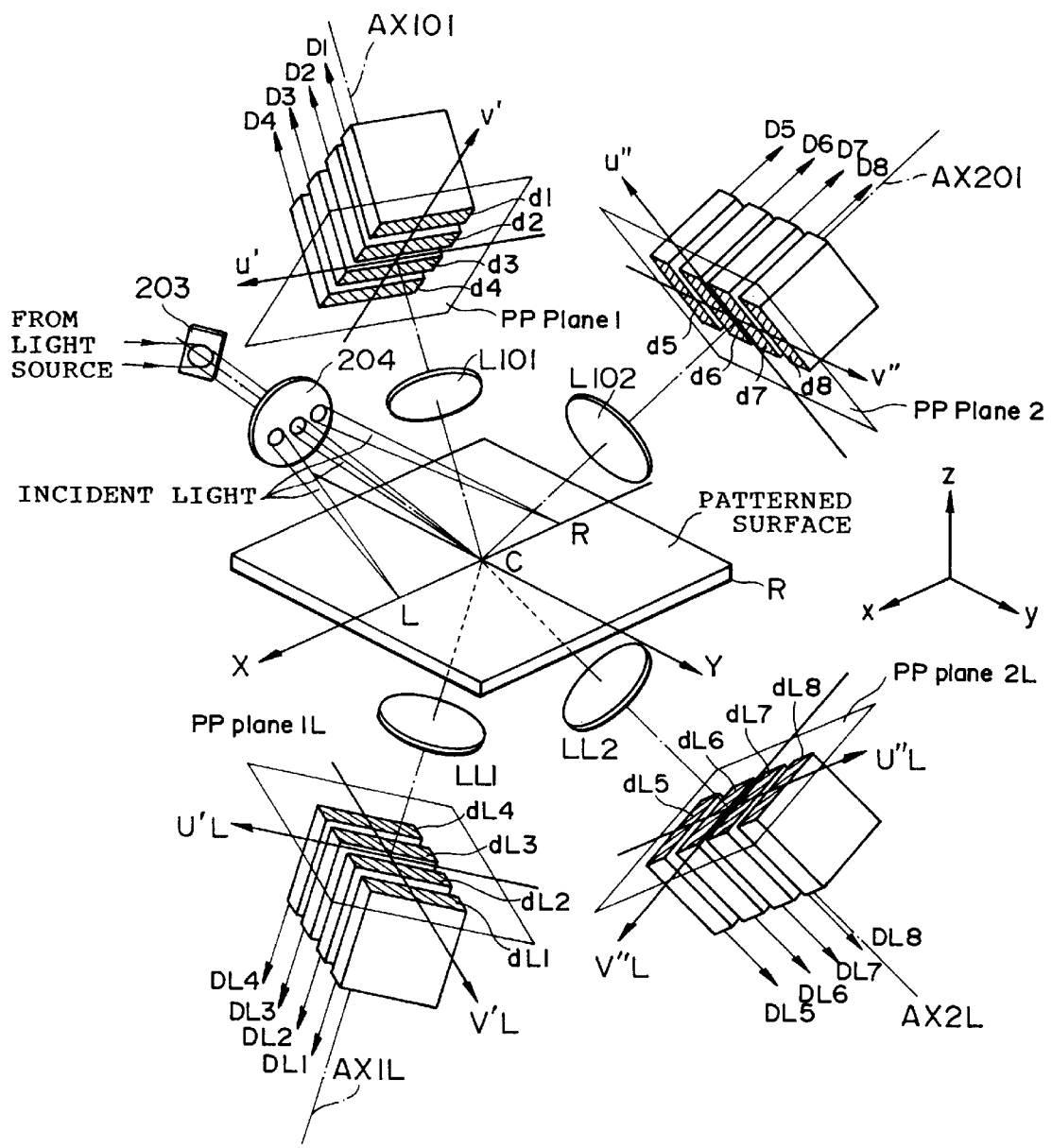
FIG. 37 is a perspective view of the apparatus of FIG. 31A.

FIG. 37 is a perspective view of the present embodiment. FIG. 37 facilitates understanding the positional relations among the light detecting surfaces of the sixteen photoelectric conversion elements disposed on the four pupil-conjugate planes in FIG. 31A.

Figure 38:
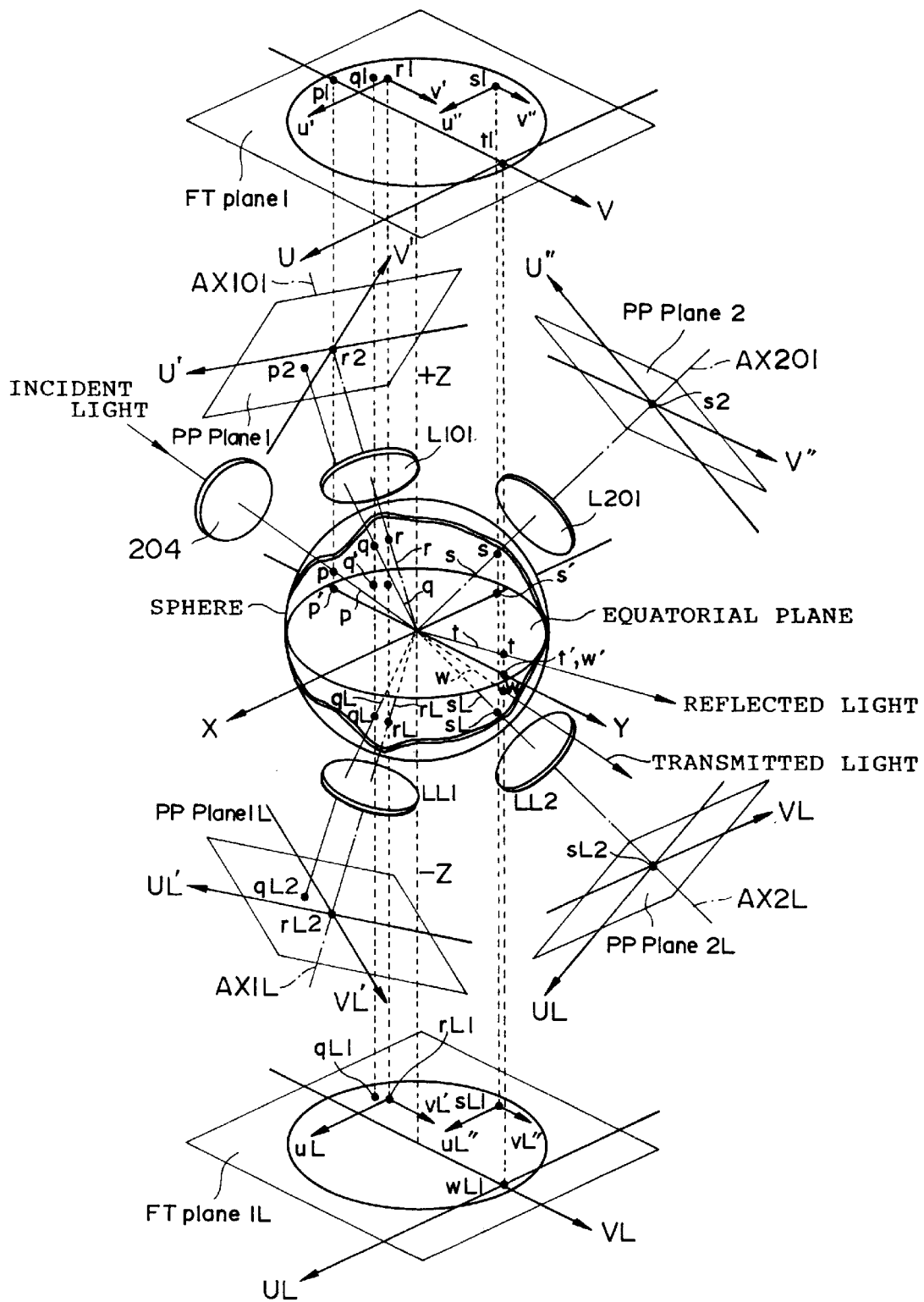
FIG. 38 is a drawing to show relations on Fourier transform planes among spectra that can be observed in the apparatus of FIG. 31A.

It also shows a state of optical scanning with the incident light on the scanning line LCR on the circuit-patterned surface. FIG. 38 is an explanatory drawing to illustrate what relation the spectra observable on the four pupil-conjugate planes have on the Fourier transform planes, which is an bird's eye view from the same viewpoint as in FIG. 37 with omitting unnecessary elements for explanation.

Let us consider a virtual sphere sufficiently larger than the laser spot formed by the illumination light, where the circuit-patterned surface of reticle is located on the XY plane. The equatorial plane of the sphere is coincident with the circuit-patterned surface. The position of the laser spot is coincident with the center of the sphere. Directions of scattered light occurring from the position of the laser spot can be expressed by vectors equal to the radius of the sphere, and intersecting points between the vectors and the sphere give a Fourier spectrum when orthogonally projected onto a plane parallel to the equatorial plane, as well known (for example in Japanese Laid-open Patent Applications No. 5-165196, No. 6-43111, and No. 6-94633). Coordinates of each point orthogonally projected are normally indicated by an orthogonal coordinate system parallel to the XY coordinate system with the zeroth-order spectrum at the origin.

Supposing the size of the sphere is 1, values obtained by subtracting direction cosines of the zeroth-order light from those of an arbitrary vector from the laser spot with respect to the X and Y axes are its coordinates on the Fourier transform plane. The unit of the Fourier transform plane this time is the spatial frequency (cycles) and a value obtained by dividing the spatial frequency by the wavelength of incident light indicates a frequency per unit length of the object (for example, cycles/micron), which is easy to understand intuitively.

Among the vectors from the position of the laser spot intersecting points on the +Z semisphere side are shown as orthogonally projected onto the first Fourier transform plane FT plane 1. Among the vectors intersecting points on the −Z semisphere side are shown as orthogonally projected onto the second Fourier transform plane FT plane 1L. Supposing the objective lenses L1, LL1 have a same NA, vectors r, rL representing directions of the optical axes AX101, AX1L, on which the objective lenses are placed, are indicated by points r, rL on the spherical surface and become points r1, rL1 on the two Fourier transform planes. The optical axes AX101, AX1L are determined so that values of these coordinates can coincide with each other between in the two orthogonal coordinate systems, i.e., the U-V coordinate system and the UL-VL coordinate system. Namely, they are arranged so that the orthogonal projections of the vectors r, rL on the equatorial plane may coincide with each other. This permits spatial spectra of the scattering light simultaneously occurring in the transmission direction and in the reflection direction to be received in a symmetrical range.

The same can be applied to the objective lenses L201, LL2. Supposing they have a same NA, vectors s, sL representing the directions of the optical axes AX201, AX2L, on which the objective lenses are disposed, are indicated by points s, sL on the spherical surface and become points s1, sL1 on the two Fourier transform planes. The optical axes AX201, AX2L are determined so that values of these coordinates may coincide with each other between in the two orthogonal coordinate systems, i.e., the U-V coordinate system and the UL-VL coordinate system. Namely, they are arranged so that the orthogonal projections of the vectors s, sL on the equatorial plane may coincide with each other. In this manner, as many optical systems can be set at positions symmetric with respect to the equatorial plane as desired.

Let us consider relations among the pupil-conjugate planes PP plane 1, PP plane 2, PP plane 1L, PP plane 2L of the objective lenses L101, L201, LL1, LL2 and the Fourier transform planes FT plane 1, FT plane 1L. A vector q is refracted by the objective lens L1 to hit a point q2 on the pupil-conjugate plane PT plane 1. This vector forms a point q1 on the Fourier transform plane FT plane 1, and it is seen that any arbitrary point on the pupil-conjugate plane PP plane 1 is in one-two-one correspondence to a point on the Fourier transform plane FT plane 1. Thus, considering an orthogonal coordinate system u'-v' being parallel to the U-V coordinate system and having the origin at the point r1 on the Fourier transform plane FT plane 1, this becomes a U'-V' coordinate system having the origin at an intersecting point r2 with the optical axis AX1 on the pupil-conjugate plane PP plane 1. Strictly speaking, the U'-V' coordinate system is not an orthogonal coordinate system and each axis is not a straight line. However, each axis may be regarded as a straight line if NA of objective lens is approximately 0.1 or less.

Similarly, considering an orthogonal coordinate system u"-v" being parallel to the U-V coordinate system and having the origin at the point s1 on the Fourier transform plane FT plane 1, it becomes a U"-V" coordinate system having the origin at an intersecting point s2 with the optical axis AX1 on the pupil-conjugate plane PP plane 2.

Similarly, considering an orthogonal coordinate system uL'-vL' being parallel to the UL-VL coordinate system and having the origin at the point rL1 on the Fourier transform plane FT plane 1L, it becomes a UL'-VL' coordinate system having the origin at an intersecting point rL2 with the optical axis AX1L on the pupil-conjugate plane PP plane 1L.

Similarly, considering an orthogonal coordinate system uL"-vL" being parallel to the UL-VL coordinate system and having the origin at the point sL1 on the Fourier transform plane FT plane IL, it becomes a UL"-VL" coordinate system having the origin at an intersecting point sL2 with the optical axis AX2L on the pupil-conjugate plane PP plane 2L.

A vector qL, being symmetric with the vector q with respect to the equatorial plane, that is, having an opposite sign of its Y component of direction cosine to that of the vector q, intersects at an intersecting point qL with the spherical surface, becoming a point qL2 on the pupil-conjugate plane PP plane 1L and a point qL1 on the Fourier transform plane FT plane 1L.

Points p', t', w' are orthogonal projections on the equatorial plane, of a vector p indicating the incident light, a vector t indicating the regularly reflected ray, and a vector w indicating the transmitted ray traveling straight, and these points become points p1, t1, wL1 on the two Fourier transform planes. The points t', w' coincide with each other, and the points t1, wL1 indicate the zeroth-order spectra and are the origins of the two orthogonal coordinate systems.

Figure 39:
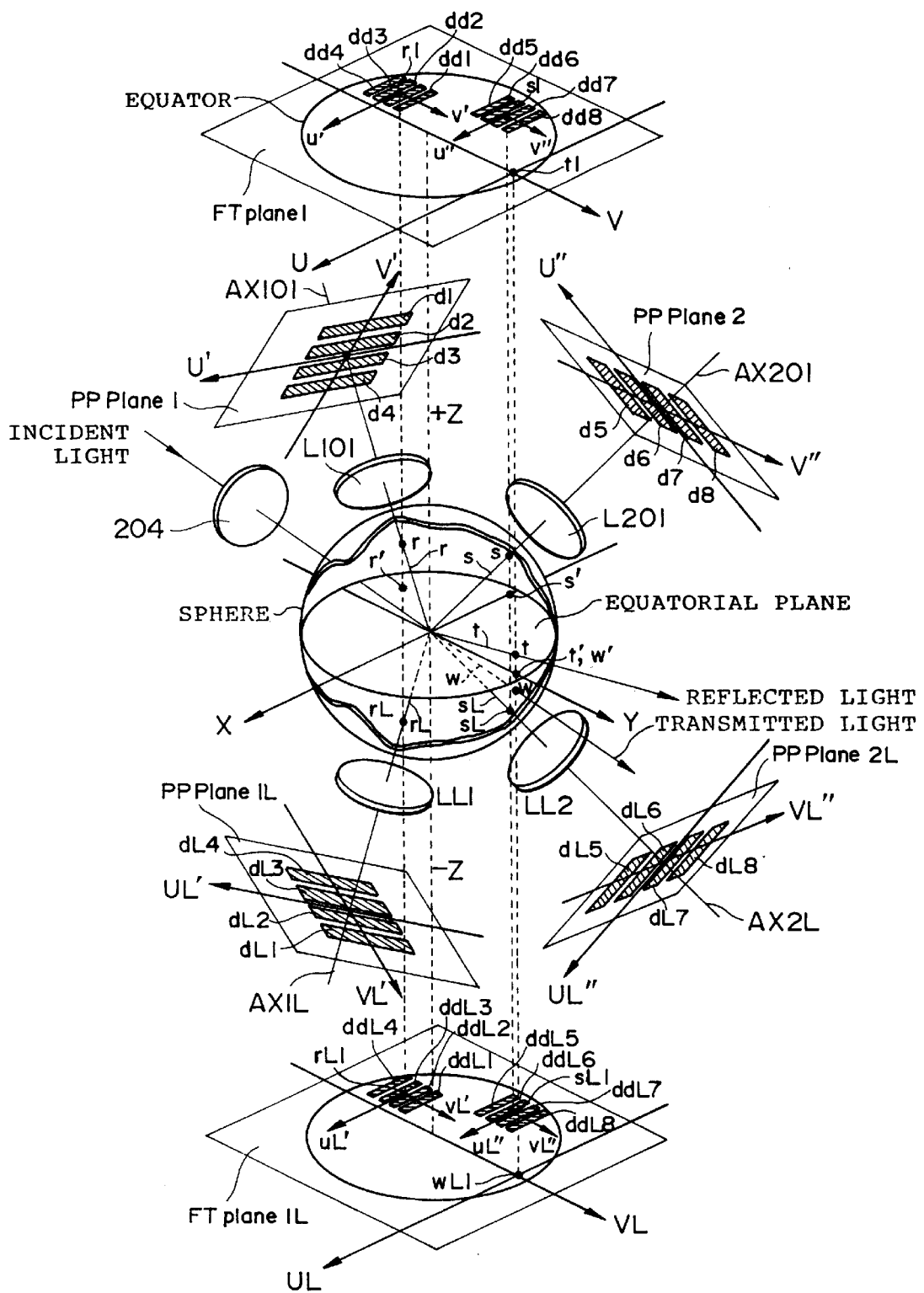
FIG. 39 is a drawing to illustrate the spatial frequencies of light received by light detection surfaces of photoelectric conversion elements in the apparatus of FIG. 31A.

FIG. 39 is a bird's eye view to show the spatial frequency regions of light received by the light detecting surfaces of photoelectric conversion elements. In the present embodiment there are two sets (L1, LL1), (L2, LL2) of objective lenses disposed in plane symmetry with respect to the XY plane in the +Z and −Z directions. Four light detecting surfaces are provided on each of the pupil-conjugate planes PP plane 1, PP plane 2, PP plane IL, PP plane 2L of these objectives. (For example, the light detecting surfaces d1, d2, d3, d4 are provided on the pupil conjugate plane PP plane 1.) These light detecting surfaces are arranged in plane symmetry with respect to the XY plane on the pupil-conjugate planes of each pair of objective lenses set in symmetry (for example, on the pupil conjugate planes PP plane 1 and PP plane 1L), and they are paired as four pairs of light detecting surfaces.

The configurations and locations on the pupil conjugate planes of each pair of two light detecting surfaces are arranged in such a manner that spatial frequency regions (Fourier spectral regions) of light received and photoelectrically converted by the light detecting surfaces may coincide with each other on the Fourier transform planes FT plane 1, FT plane 1L.

From this bird's eye view, as explained with FIG. 38, these spatial frequency regions (Fourier spectral regions) can be readily drawn by the above technique using the orthogonal projection on the Fourier transform planes FT plane 1, FT plane 1L, and the configurations and positions of the light detecting surfaces may be determined on the pupil-conjugate planes so that the positions and configurations of these spatial frequency regions may be congruent.

For example, since the light detecting surface d1 is on the +Z side, a Fourier spectrum thereof is dd1 observed on the Fourier transform plane FT plane 1. When a region congruent to it is drawn on the Fourier transform plane FT plane 1L, it is ddL1. A configuration of the light detecting surface dL1 is determined on the pupil-conjugate plane PP plane 1L of the objective lens LL1 disposed in symmetry with the objective lens L101 so as to receive the Fourier spectral region.

The all light detecting surfaces are rectangles having their longitudinal direction along the U or UL direction on each Fourier transform plane and are arranged at equal intervals, and the arrangement method of this type is optimal for filtering of Fourier spectrum of two-dimensional periodic pattern. The detailed design method thereof is disclosed, for example, in Japanese Laid-open Patent Applications No. 5-165196, No. 6-94633, and so on. The above embodiment uses a plurality of photoelectric conversion elements per objective lens. When diffracted light of circuit pattern with a relatively high intensity is incident into an element, the photoelectric conversion element is electrically saturated. In that case, a linear differential output cannot be attained, and the upper limit of the dynamic range is determined. The lower limit of the dynamic range is determined by the electrical and optical noise, of course. Thus, the upper limit needs to be expanded in order to obtain a wider dynamic range. To meet this requirement, the above embodiment employs a plurality of photoelectric conversion elements per objective lens.

The lower limit of the dynamic range can of course be lowered by a method for decreasing the beam spot size of illumination light or the like, but the beam spot size of illumination light cannot be easily decreased because it strongly relates to the inspection period of time or the like.

It is, however, noted that an inspection apparatus having practical performance can be constructed in the arrangement of a photoelectric conversion element for each of the objective lenses.

Figure 40:
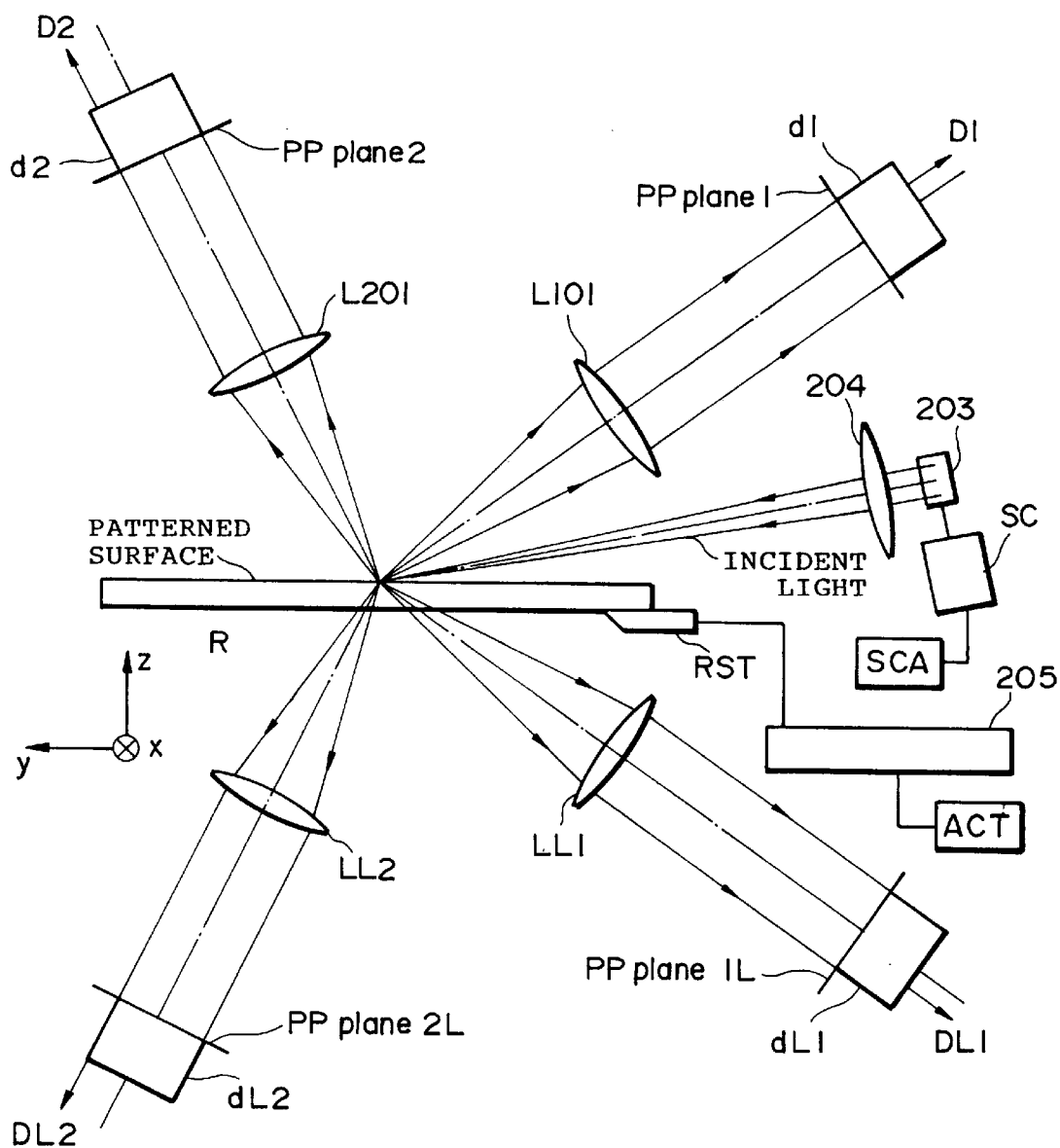
FIG. 40 is a drawing to illustrate the ninth embodiment of the present invention.

FIG. 40 shows the ninth embodiment of the present invention, which is an example in which a photoelectric conversion element is set for each objective lens by decreasing the number of photoelectric conversion elements in the eighth embodiment. Similar members to those in FIG. 31A are denoted by the same reference numerals, and the detailed description thereof is omitted herein. The objective lenses are located at positions where the direct reflected light or the direct transmitted light is not incident; for example, they are disposed at positions in plane symmetry with respect to the pattern-scribed surface of the reticle R as in the eighth embodiment.

Figure 41:
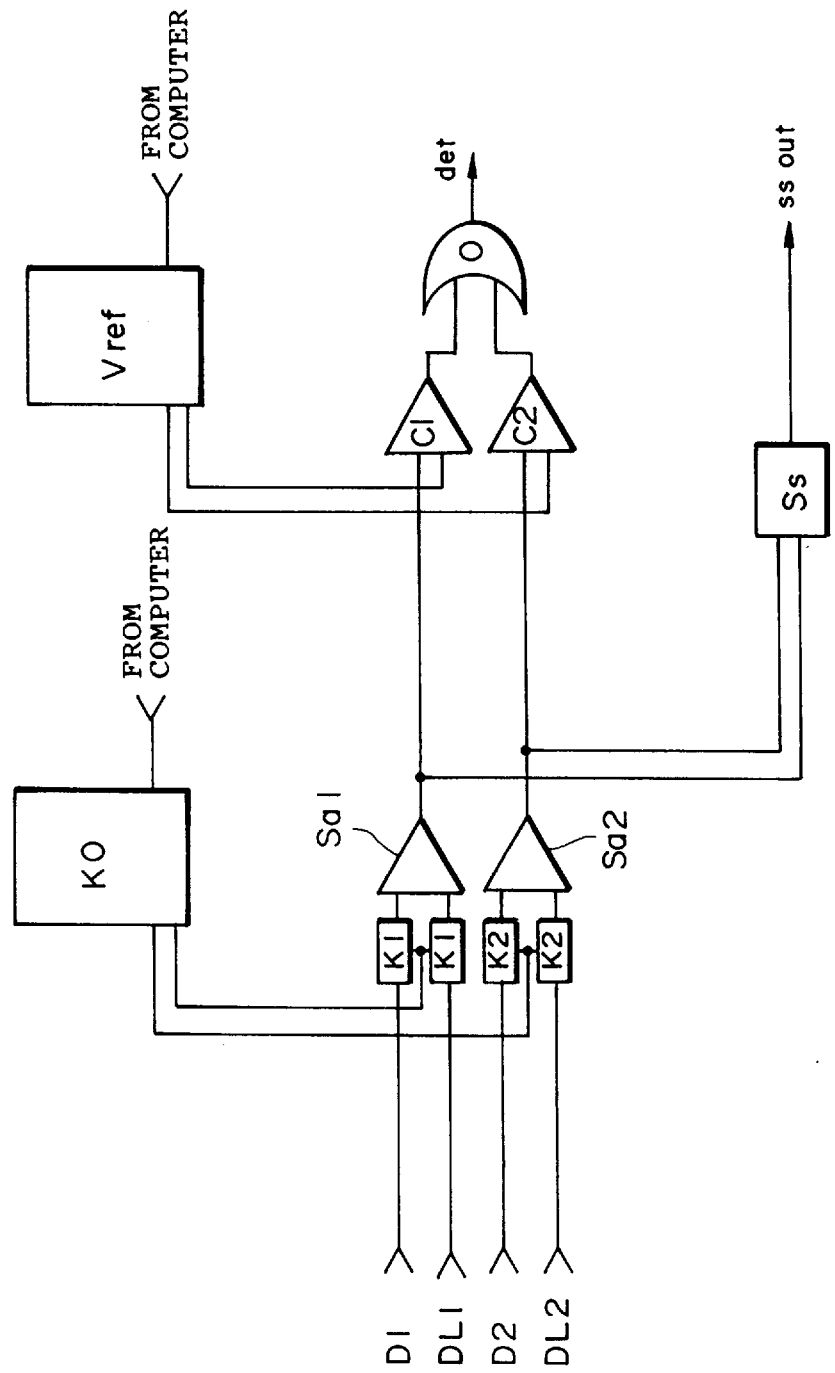
FIG. 41 is a drawing to illustrate the signal processing system of FIG. 40.

FIG. 41 shows a signal processing circuit most suitable for the present embodiment. This figure shows a modification of FIG. 35. Without necessitating an AND logic, a judgment of whether foreign matter is present or absent can be made only by an OR logic 0. Namely, presence of foreign matter is determined when either one of outputs from the differential amplifiers Sa1, Sa2 exceeds the reference level set from the computer COM (see FIG. 32). The signal selecting circuit $S_s$ is a maximum selecting circuit for always selecting a maximum signal. The reticle conveying system and control system may be those shown in FIG. 32 as in the eighth embodiment.

Figure 42:
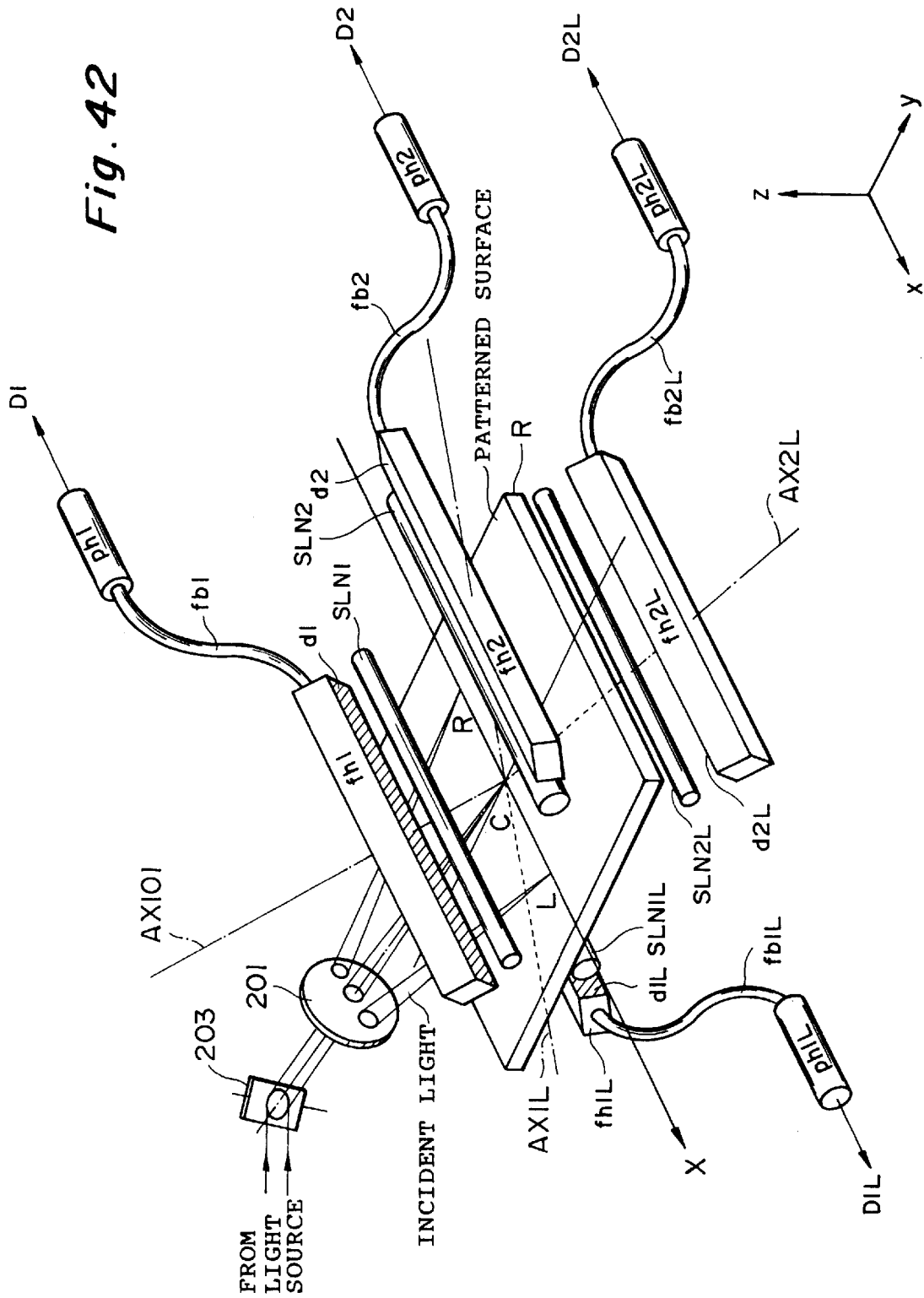
FIG. 42 is a drawing to illustrate the tenth embodiment of the present invention.
Figure 43:
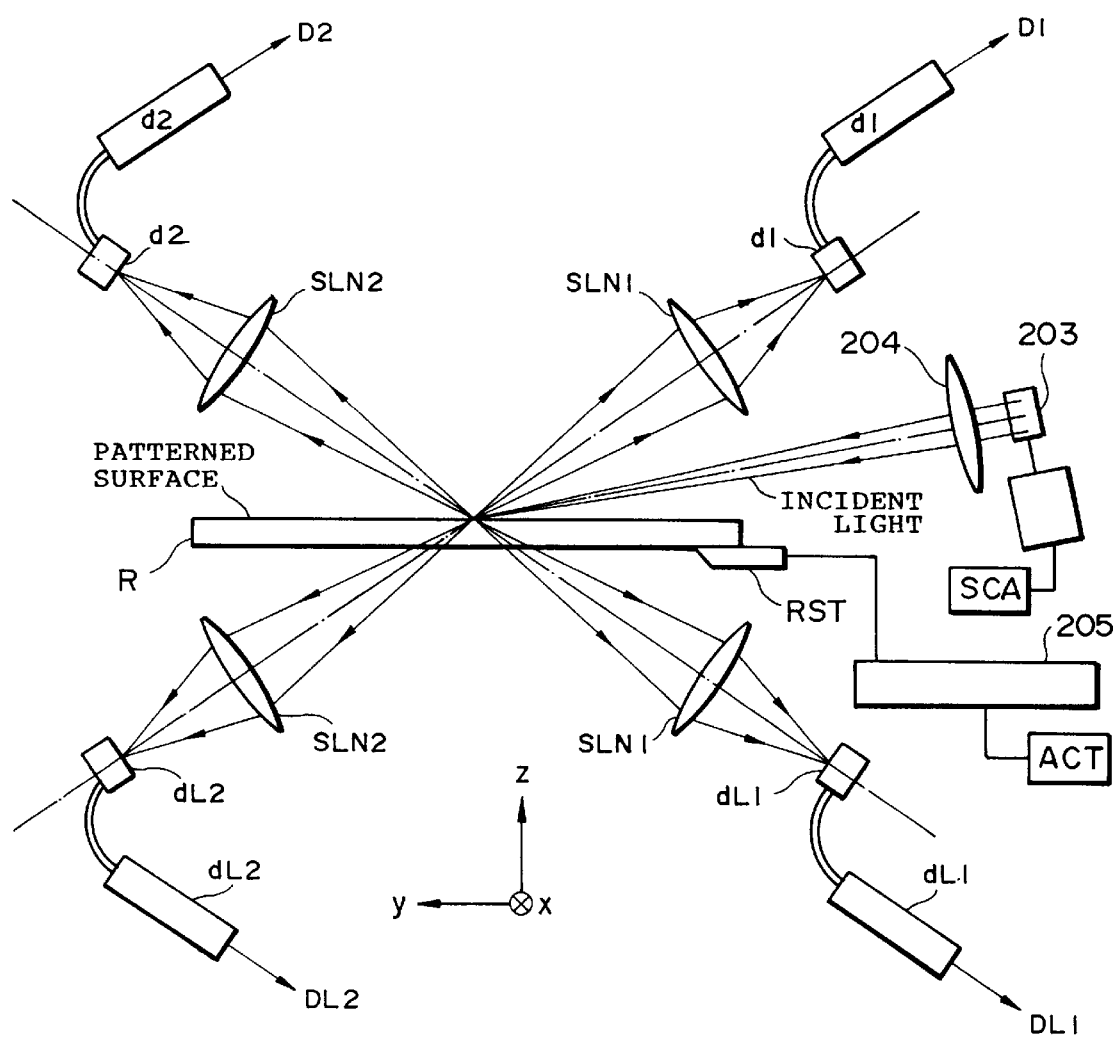
FIG. 43 is a drawing to illustrate a control system in the apparatus of FIG. 42.

FIG. 42 shows the tenth embodiment of the present invention, which is an example in which the light receiving optical systems of the ninth embodiment are constructed of cylindrical lenses. Similar members to those in FIG. 41 are denoted by the same reference numerals and the detailed description thereof is omitted herein. In FIG. 42 pairs of cylindrical lenses (SLN1, SLN1L), (SLN2, SLN2L) are located at positions where the direct reflected light (regularly reflected light) or the direct transmitted light is not incident, they are disposed at positions in plane symmetry with respect to the pattern-scribed surface of the reticle R as in the previous embodiments, and they are designed so that Fourier spectra of rays received by them are coincident with each other, as explained with FIG. 39. The rays condensed by these cylindrical lenses are incident into light entrance ends d1, d2, d1L, d2L of optical fiber assemblies fh1, fh2, fh1L, fh2L and they are guided through optical fiber portions fb1, fb2, fb1L, fb2L to photoelectric conversion elements ph1, ph2, ph1L, ph2L such as photomultipliers to be photoelectrically converted thereby. The signal processing circuit may be the same as in the ninth embodiment, and, as shown in FIG. 43, the reticle conveying system and the control system may be those shown in FIG. 32 as in the eighth embodiment.

In the previous embodiments, the arrangement to enable to inspect the entire surface of reticle by the one-dimensional scanning means of incident light (for example, the oscillating mirror and the objective lens) and the one-dimensional scanning means of reticle (for example, the driving system of the reticle stage) may be replaced by an arrangement to enable to inspect the entire surface of reticle by two-dimensional scanning of incident light.

In the above embodiments, a desired arrangement is to observe an image of a defect detected after inspection in order to specifically grasp significance or degree of a defect. Here, the optical system in the above embodiments can obtain a two-dimensional optical image of the object under the dark field illumination by cooperative operation of laser scanning and stage movement. If the laser scanning optical system is preliminarily arranged to perform the two-dimensional scanning, inspection becomes possible without moving the stage. This two-dimensional scanning can be realized by combining the system with a polygon mirror or the like conventionally known. In this case, if a defect is displayed on a display using the outputs from the differential amplifiers, i.e., the output of Ss out shown in FIG. 34 or using a luminance signal proportional thereto, the circuit pattern is not imaged and only the foreign matter detected can be observed at high contrast, which permits an observer to easily grasp the size of foreign matter or the like.

Figure 31B:
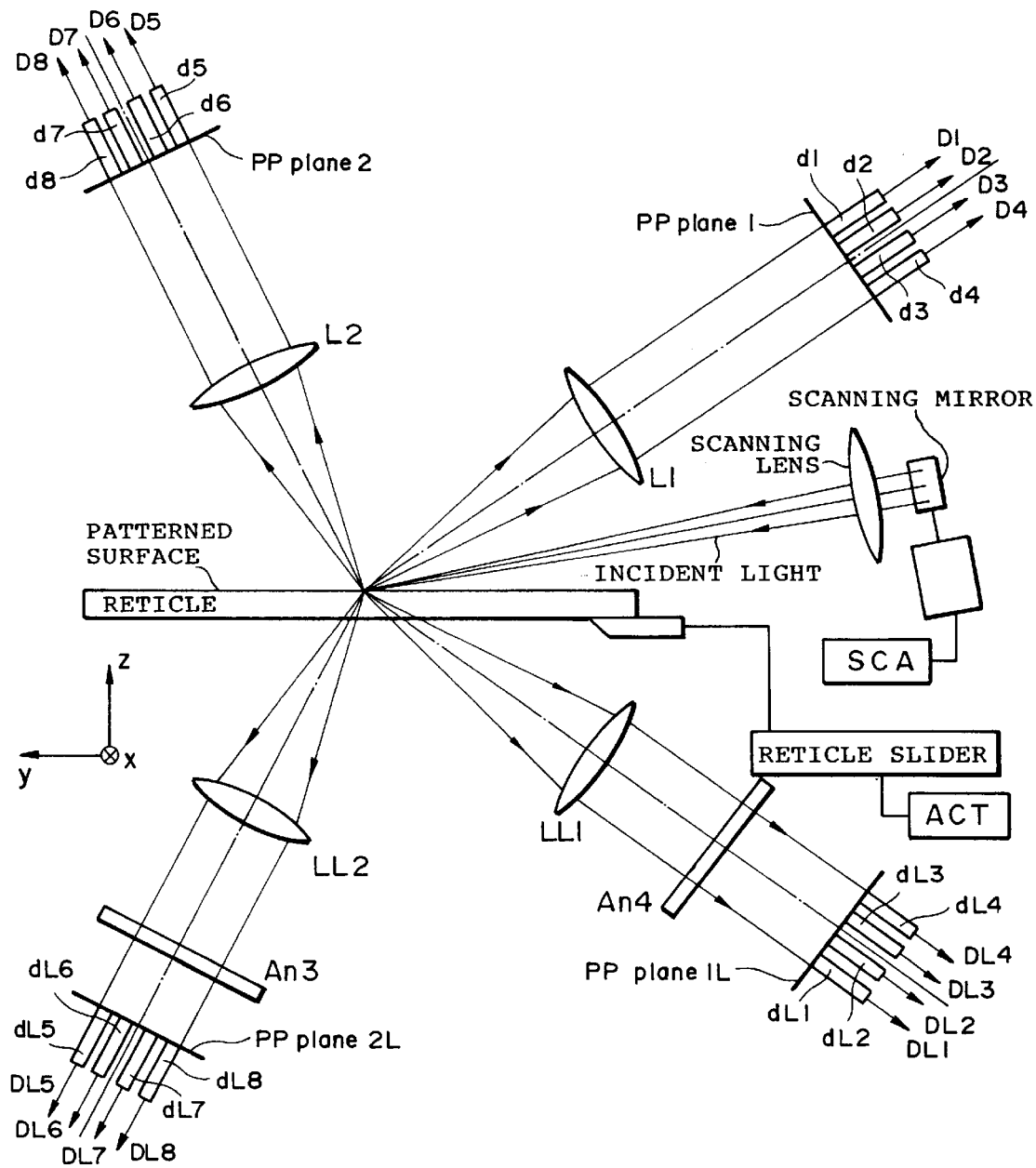
FIGS. 31B, 31C, and 31D are drawings to illustrate modifications of the eighth embodiment.
Figure 31C:
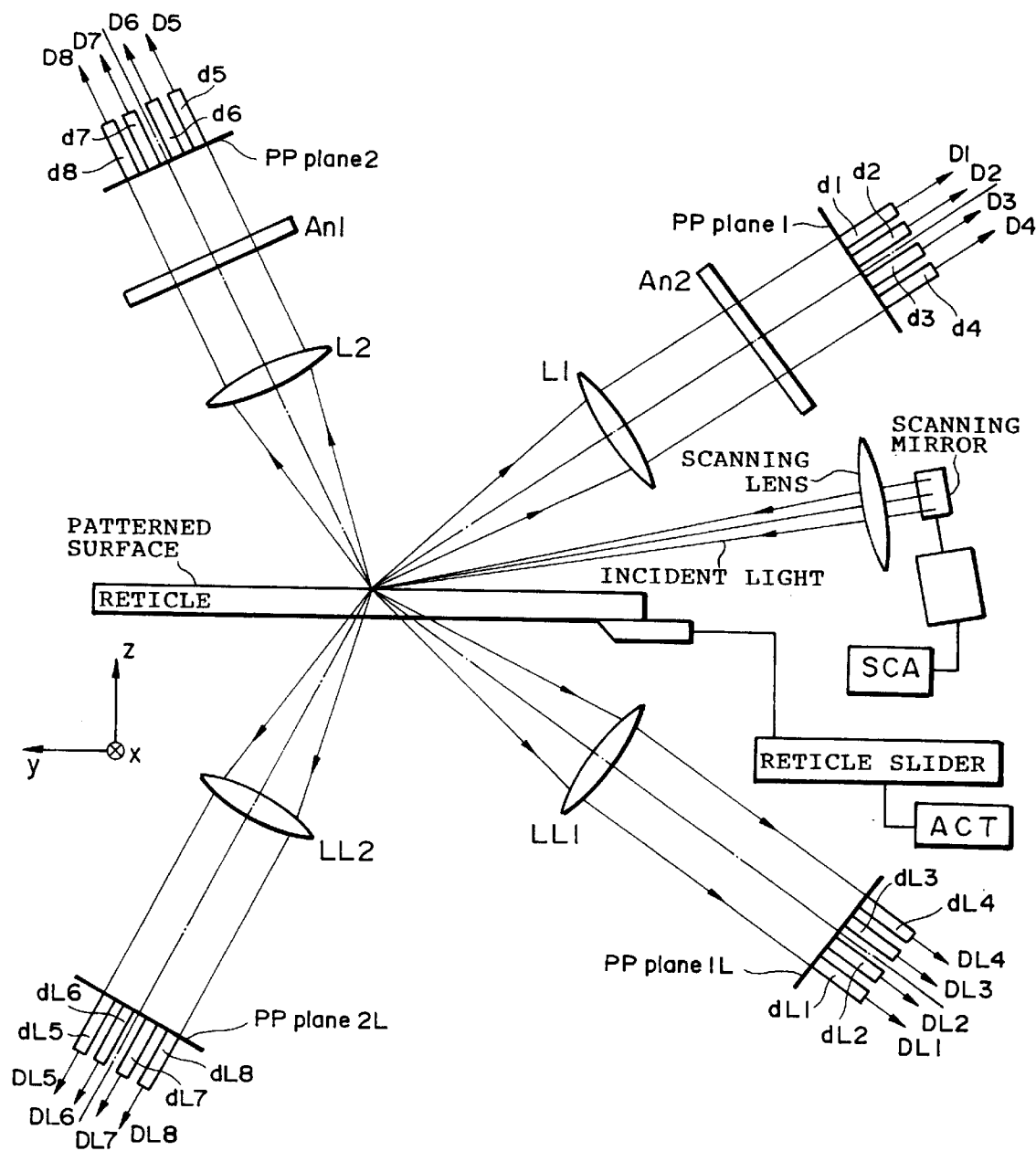
Figure 31D:
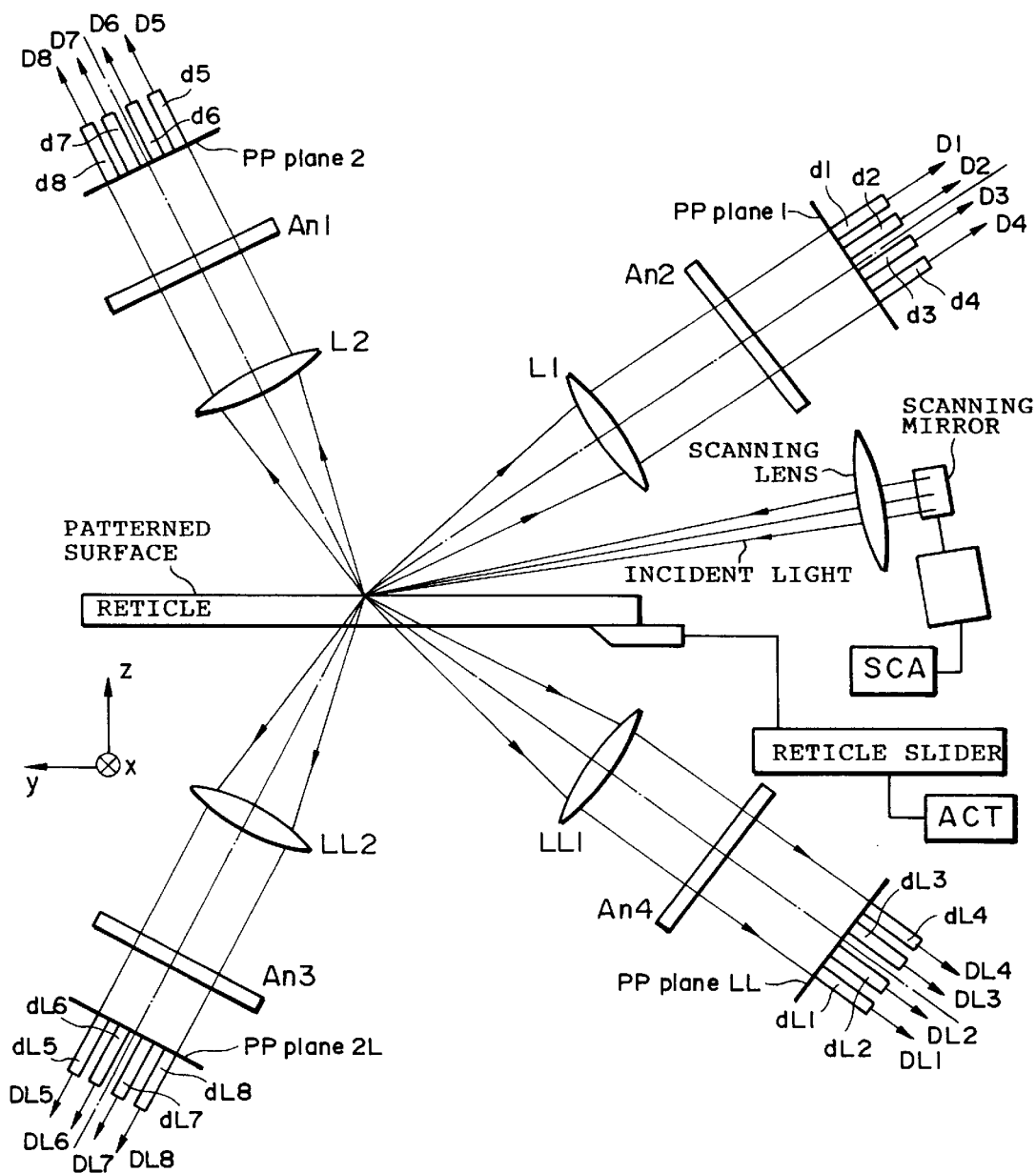

In the embodiment shown in FIG. 31A, there are some cases where the scattered light from a vertical portion of a pattern edge becomes optical noise. In order to eliminate it, it is preferred to remove the optical noise by setting analyzers An1–An4 in respective optical paths of either one or both of the transmitted light and reflected light, as shown in FIGS. 31B–31D. This is because polarization of the scattered light from the vertical portion of pattern edge is different from polarization from a flat end face portion (a surface parallel to the mask). This enables to remove the optical noise and to realize ideal erasure of the circuit pattern image on the mask. As shown in FIGS. 31B–31D, the upper and lower analyzers on either side of the mask preferably have their transmission axes symmetric with each other.

These analyzers are preferably applied to the other embodiments without having to be limited to the embodiments shown in FIG. 31D.

Figure 44A:
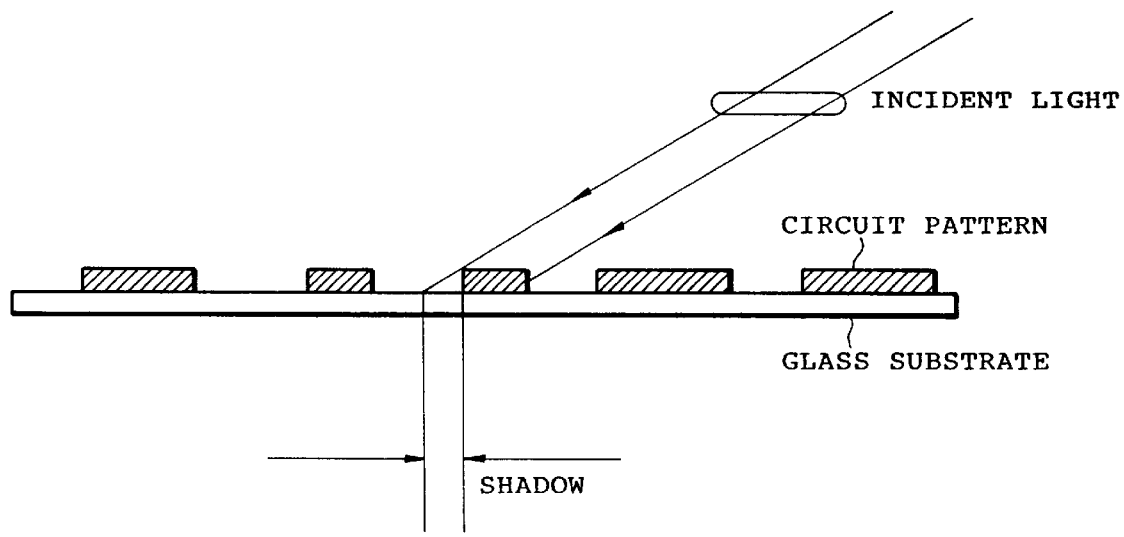
FIGS. 44A and 44B are drawings to illustrate an improved principle by changing direction of incidence of light to the mask.
Figure 44B:
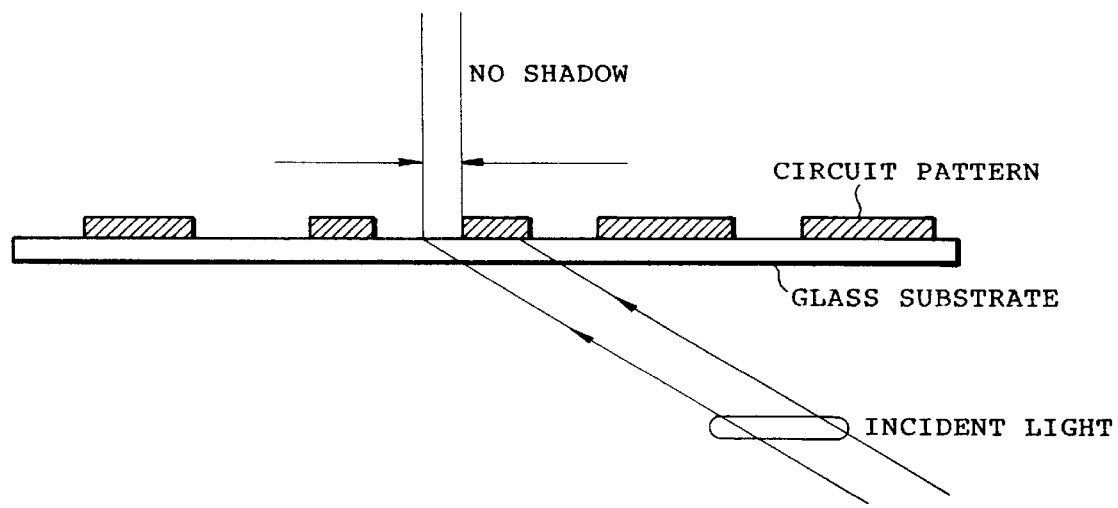

Concerning the incident direction of the illumination light, there are some cases where, as shown in FIG. 44A, when the circuit pattern is illuminated from the pattern-formed surface side, a vertical portion of a circuit pattern edge forms a shadow part of the circuit pattern in the glass portion and it changes an intensity ratio of light waves traveling in the transmission direction and light waves traveling in the reflection direction from an ideal value. In order to avoid it, the illumination light is preferably incident from the opposite side to the circuit-pattern-formed surface of mask, as shown in FIG. 44B.

As detailed above, the present invention enables to detect a low-level-difference foreign object or a semitransparent foreign object.

Further, a high-sensitivity foreign matter inspection apparatus can be constructed without relying upon the highly advanced image processing technology.

Since the present invention is suitably applicable to the cases where the circuit pattern on the mask is a distribution function of one reflectance and one transmittance, a circuit-scribing material applied without problem is not only a light shielding member such as chromium, but also an optically transparent material called as halftone. Namely, the present invention can be applied to the conventional reticles of circuit pattern of chromium shielding film, and halftone reticles in which the circuit pattern is scribed only by phase shifter using an optically transparent thin film.

The beam spot size can be expanded, so as to decrease the inspection period of time.

When compared with the method for stopping the scattered light and diffracted light from the circuit pattern only by the conventional spatial filters, degrees of freedom are increased for the arrangement of light receiving optical systems; for example, the light receiving optical systems may be set near the zeroth-order spatial frequency spectrum. Therefore, the invention can provide an inspection apparatus that can also inspect presence or absence of deposition of a foreign object generating the scattered light only near the zeroth-order spatial frequency spectrum, which was not easy to detect heretofore, for example a flat foreign object decreasing its thickness gently in a contour portion of the foreign object and having the unclear contour.

What is claimed is:

1. A mask defect inspection apparatus for optically detecting a defect on a mask having a circuit pattern, comprising:

an illumination system for illuminating said mask with inspection light;

a first light receiving optical system for receiving said inspection light reflected by said mask;

a second light receiving optical system for receiving said inspection light transmitted by said mask;

a first spatial filter for shielding at least a zeroth-order diffraction light of said inspection light in a central area, wherein said central area includes at least an optical axis of said first light receiving optical system in an optical Fourier transform plane for said circuit pattern in said first light receiving optical system;

a second spatial filter for shielding at least a zeroth-order diffraction light of said inspection light in a central area, wherein said central area includes at least an optical axis of said second light receiving optical system in an optical Fourier transform plane for said circuit pattern in said second light receiving optical system;

a first detector for photoelectrically converting said inspection light having passed through said first spatial filter;

a second detector for photoelectrically converting said inspection light having passed through said second spatial filter; and a gain adjusting circuit for adjusting a gain of a first output signal from said first detector to output a third output signal and adjusting a gain of a second output signal from said second detector to output a fourth output signal, wherein said defect is detected based on one of a relative intensity difference and intensity ratio between said third output signal and said fourth output signal gain adjusted by said gain adjusting circuit.

2. The apparatus according to claim 1, wherein at least one of said first light receiving optical system and said second light receiving optical system has a gain optical system for optically adjusting relative gains of said first output signal and said second output signal and signal processing system for detecting said defect, based on said first output signal and said second output signal after said gains thereof are adjusted, is provided.

3. The apparatus according to claim 1, wherein gain setting of said gain adjusting circuit is to adjust the gains so that the intensity difference between said third and fourth output signals becomes nearly zero or so that the intensity ratio thereof becomes substantially 1.

4. The apparatus according to claim 1, comprising a display device, which uses the same optical systems in imaging the defect detected by mask defect inspection in order to observe it as upon the defect inspection and which can display an image of a luminance signal proportional to the intensity difference or the intensity ratio between said third and fourth output signals.

5. The apparatus according to claim 1, wherein an analyzer for transmitting polarized light with a predetermined plane of polarization is located near at least one of said first and second spatial filters.

6. The apparatus according to claim 1, which is optically arranged so that said inspection light is incident from a circuit-scribed side of said mask.

7. The apparatus according to claim 1, which is optically arranged so that said inspection light is incident from an opposite side to a circuit-scribed surface of said mask.

8. A mask inspection apparatus for inspecting a defect of a mask having a circuit pattern on a first surface of an optically transparent substrate of a flat plate shape, but having no circuit pattern on a second surface opposed to the first surface, comprising:

illuminating means for illuminating an inside area of an inspection region being a region inside said first surface as an inspection object of the mask;

two light receiving means disposed separately from each other in two spaces obtained when a space including said mask is divided into two by a plane including said first surface, said two light receiving means being second light receiving means located in a second space including said second surface and first light receiving means located in a first space not including said second surface, wherein said first light receiving means includes a first spatial filter for shielding at least a zeroth-order diffraction light, and wherein said second light receiving means includes a second spatial filter for shielding at least a zeroth-order diffraction light;

first photoelectric conversion means for photoelectrically converting rays occurring from the inside area of said inspection region of said mask and entering said first light receiving means;

second photoelectric conversion means for photoelectrically converting rays occurring from the inside area of said inspection region of said mask and entering the second light receiving means; and a gain adjusting circuit for adjusting a gain of a first output signal output from said first photoelectric conversion means to output a third output signal and adjusting a gain of a second output signal output from said second photoelectric conversion means to output a fourth output signal, wherein said defect is detected based on one of a relative intensity difference and intensity ratio between said third output signal and said fourth output signal gain-adjusted by said gain adjusting circuit.

9. The apparatus according to claim 8, wherein said first light receiving means and said second light receiving means comprise respective objective lenses having a field in said inspection region.

10. The apparatus according to claim 8, wherein spatial filters are provided near said objective lenses.

11. The apparatus according to claim 8, wherein said first photoelectric conversion means and said second photoelectric conversion means comprise respective image pickup elements located in image planes conjugate with said inspection region.

12. The apparatus according to claim 8, wherein said first photoelectric conversion means and said second photoelectric conversion means are disposed near planes conjugate with pupils of said objective lenses.

13. The apparatus according to claim 8, wherein said first and second photoelectric conversion means have a plurality of photoelectric conversion surfaces for outputting a plurality of independent photoelectric conversion signals.

14. The apparatus according to claim 8, wherein said illuminating means has an optical scanning mechanism.

15. The apparatus according to claim 8, wherein gain setting of said gain adjusting circuit is to adjust the gains so that the intensity difference between said third and fourth output signals becomes nearly zero or so that the intensity ratio thereof becomes substantially 1.

16. A mask inspection apparatus for inspecting a defect of a mask having a circuit pattern on a first surface of an optically transparent substrate of a flat plate shape, but having no circuit pattern on a second surface opposed to the first surface, comprising:

illuminating means for illuminating an inside area of an inspection region being a region inside said first surface as an inspection object of the mask;

two light receiving means disposed separately from each other in two spaces obtained when a space including said mask is divided into two by a plane including said first surface, said two light receiving means being second light receiving means located in a second space including said second surface and first light receiving means located in a first space not including said second surface;

first photoelectric conversion means for photoelectrically converting rays occurring from the inside area of said inspection region of said mask and entering said first light receiving means;

second photoelectric conversion means for photoelectrically converting rays occurring from the inside area of said inspection region of said mask and entering the second light receiving means; and a gain adjusting circuit for adjusting a gain of a first output signal output from said first photoelectric conversion means to output a third output signal and adjusting a gain of a second output signal output from said second photoelectric conversion means to output a fourth output signal, wherein said defect is detected based on one of a relative intensity difference and intensity ratio between said third output signal and said fourth output signal gain-adjusted by said gain adjusting circuit;

wherein the mask inspection apparatus further comprises a display device, which uses the same optical systems in imaging the defect detected by mask defect inspection in order to observe it as upon the defect inspection and which can display an image of a luminance signal proportional to one of the intensity difference and the intensity ratio between said third and fourth output signals.

17. The apparatus according to claim 8, wherein an analyzer for transmitting polarized light with a predetermined plane of polarization is located near at least one of said first and second spatial filters.

18. The apparatus according to claim 8, which is optically arranged so that said inspection light is incident from a circuit-scribed side of said mask.

19. The apparatus according to claim 8, which is optically arranged so that said inspection light is incident from an opposite side to a circuit-scribed surface of said mask.

20. A mask defect inspection apparatus for inspecting a defect of a mask, comprising:

first illuminating means for vertically illuminating an inside area of a first region of an inspected surface of said mask;

second illuminating means for transmission-illuminating the inside area of the first region of said inspected surface from a surface of said mask different from said inspected surface;

ray selecting means for condensing only scattered light occurring from inside a second region at a first position in said first region into a first ray;

ray splitting means for splitting said first ray into a second ray and a third ray;

first photoelectric conversion means for photoelectrically converting said second ray;

second photoelectric conversion means for photoelectrically converting said third ray; and a gain adjusting circuit for adjusting a gain of a first output signal output from said first photoelectric conversion means to output a third output signal and adjusting a gain of a second output signal output from said second photoelectric conversion means to output a fourth output signal, wherein said defect is detected based on either a relative intensity difference or intensity ratio between said third output signal and said fourth output signal gain-adjusted by said gain adjusting circuit.

21. The apparatus according to claim 20, wherein a predetermined circuit pattern is scribed on said inspected surface.

22. The apparatus according to claim 20, wherein illumination light beams from said first illuminating means and from said second illuminating means are linearly polarized light beams having respective planes of polarization perpendicular to each other on said inspected surface.

23. The apparatus according to claim 20, wherein said second region is sufficiently smaller than said first region.

24. The apparatus according to claim 20, wherein said ray splitting means is a polarizing beam splitter.

25. The apparatus according to claim 20, wherein said ray selecting means is a combination of an objective lens with one-dimensional optical deflecting means.

26. The apparatus according to claim 20, wherein said ray selecting means is a combination of an objective lens with two-dimensional optical deflecting means.

27. The apparatus according to claim 20, wherein gain setting of said gain adjusting circuit is to adjust the gains so that the intensity difference between said third and fourth output signals becomes nearly zero or so that the intensity ratio thereof becomes substantially 1.

28. The apparatus according to claim 20, comprising a display device, which uses the same optical systems in imaging the defect detected by mask defect inspection in order to observe it as upon the defect inspection and which can display an image of a luminance signal proportional to the intensity difference or the intensity ratio between said third and fourth output signals.

29. A mask defect inspection apparatus for inspecting a defect of an optically transparent substrate of a plate shape having a first surface and a second surface opposed to each other, wherein a pattern is scribed on said first surface but no pattern is scribed on said second surface, comprising:

a laser light source for emitting a laser beam;

light scanning means for condensing said laser beam in a first region of the first surface of said substrate and irradiating the first region with the laser beam, said light scanning means continuously moving said first region in one-dimensional direction in the pattern-scribed surface of said substrate;

first light receiving means having a photoelectric conversion element and disposed in a first space region not including said second surface, said first space region being one of two space regions divided by a first plane including the first surface of said substrate;

second light receiving means having a photoelectric conversion element and disposed in a second space region including said second surface, said second space region being one of the two space regions divided by the first plane including the first surface of said substrate; and a gain adjusting circuit for adjusting a gain of a first output signal from said first light receiving means to output a third output signal and adjusting a gain of a second output signal from said second light receiving means to output a fourth output signal, wherein said defect is detected based on either a relative intensity difference or intensity ratio between said third output signal and said fourth output signal gain-adjusted by said gain adjusting circuit.

30. The apparatus according to claim 29, wherein a first ray photoelectrically converted by said first light receiving means and a second ray photoelectrically converted by said second light receiving means, after occurring from said first region, are in a relation of plane symmetry with respect to said first surface.

31. The apparatus according to claim 29, wherein each of said first light receiving means and said second light receiving means has a same number of photoelectric conversion elements.

32. The apparatus according to claim 29, wherein an arbitrary ray out of such plural first rays is paired in a 1:1 relation of plane symmetry with respect to said first surface with either one ray out of such plural second rays.

33. The apparatus according to claim 29, wherein gain setting of said gain adjusting circuit is to adjust the gains so that the intensity difference between said third and fourth output signals becomes nearly zero or so that the intensity ratio thereof becomes substantially 1.

34. The apparatus according to claim 29, comprising a display device, which uses the same optical systems in imaging the defect detected by mask defect inspection in order to observe it as upon the defect inspection and which can display an image of a luminance signal proportional to the intensity difference or the intensity ratio between said third and fourth output signals.

* * * * *